United States Patent [19]

Brickner

[11] Patent Number: 5,164,510
[45] Date of Patent: Nov. 17, 1992

[54] 5'INDOLINYL-5BETA-AMIDOMETHYLOX-AZOLIDIN-2-ONES

[75] Inventor: Steven J. Brickner, Portage, Mich.

[73] Assignee: The Upjohn Company, Kalamazoo, Mich.

[21] Appl. No.: 655,419

[22] Filed: Feb. 20, 1991

Related U.S. Application Data

[63] Continuation-in-part of Ser. No. 324,942, Mar. 17, 1989, abandoned, Ser. No. 253,850, Oct. 5, 1988, abandoned, and Ser. No. 244,988, Sep. 15, 1988, abandoned.

[51] Int. Cl.$^5$ .......................................... C07D 263/20
[52] U.S. Cl. ................... 548/231; 546/273; 546/196; 546/199; 548/229; 548/232; 548/257; 548/260; 548/452; 548/465; 548/483; 548/304.4; 548/361.1
[58] Field of Search ............... 548/229, 232, 231; 514/396

[56] References Cited

U.S. PATENT DOCUMENTS

| | | | |
|---|---|---|---|
| 4,705,799 | 10/1987 | Gregory | 548/232 |
| 4,801,600 | 1/1989 | Wang et al. | 548/229 |
| 4,965,268 | 10/1990 | Wang et al. | 548/229 |
| 4,977,173 | 11/1990 | Britelli | 548/229 |
| 4,985,429 | 1/1991 | Wang et al. | 548/229 |
| 5,036,092 | 7/1991 | Wang et al. | 548/229 |
| 5,039,690 | 8/1981 | Wang et al. | 548/229 |
| 5,043,443 | 8/1991 | Carlson | 544/357 |

OTHER PUBLICATIONS

Ioli et al., Chem. Abstr. vol. 103 entry 160009b(1985).
Beicsteins Handbuch vol. 145, 4 Aufl XXVII.

*Primary Examiner*—Donald G. Daus
*Attorney, Agent, or Firm*—Bruce Stein

[57] ABSTRACT

The present invention relates to 5'-indolinyloxazolidin-2-ones (XI)

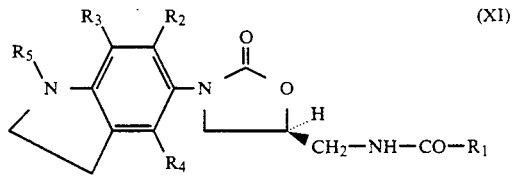

3-(fused-ring) substituted)phenyl-5β-amidomethyloxazolidin-2-ones (XXI)

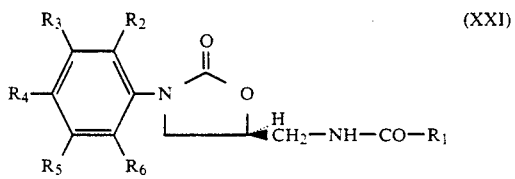

and 3-(nitrogen substituted)phenyl-5β-amidomethyloxazolidin-2-ones (LV) which are useful as antibacterial agents and the intermediates (VI), (VII) and (VIII) useful for their production.

7 Claims, No Drawings

5'INDOLINYL-5BETA-AMIDOMETHYLOXAZOLIDIN-2-ONES

This application is the national phase of international application PCT/US89/03548, filed Aug. 22, 1989, which designated the U.S.; which is a continuation-in-part of U.S. applications, Ser. No. 07/324,942 filed Mar. 17, 1989, abandoned Sep. 20, 1989; Ser. No. 07/253,850 filed Oct. 5, 1988, abandoned Sep. 14 1989, and Ser. No. 07/244,988 filed Sep. 15, 1988, abandoned Sep. 14, 1989.

BACKGROUND OF THE INVENTION

1. Field of the Invention

The present invention relates to 5'-indolinyloxazolidinones (XI), 3-(fused-ring substituted)phenyl-5$\beta$-amidomethyloxazolidinones (XXI), 3-(nitrogen substituted)phenyl-5$\beta$-amidomethyloxazolidinones (LV) which are useful as antibacterial agents.

2. Description of the Related Art

U.S. Pat. No. 4,128,654 discloses 5-halomethylphenyl-2-oxazolidin-ones which are useful in controlling fungal and bacterial diseases of plants.

U.S. Pat. No. 4,250,318 discloses 3-substituted phenyl-5-hydroxy-methyloxazolidinones having antidepressive utility.

U.S. Pat. No. Re. 29,607 discloses 3-substituted phenyl-5-hydroxymethyloxazolidinones having antidepressive, tranquilizing and sedative utility.

U.S. Pat. No. 4,340,606 discloses 3-(p-alkylsulfonyl)-phenyl-5-(hydroxymethyl or acyloxymethyl)oxazolidinones having antibacterial activity in mammals.

Belgium Pat. 892,270 discloses 3-(arylalkyl, arylalkenyl or arylacetylenic substituted)phenyl)-5-(aminomethyl)oxazolidinones which are inhibitors of monoamine oxidase.

U.S. Pat. No. 4,461,773 discloses 3-substituted phenyl-5-hydroxymethyloxazolidinones which have antibacterial activity.

European Patent Publications 127,902 and 184,170 disclose 3-substituted phenyl-5-amidomethyloxazolidinones which have antibacterial utility.

Antimicrobial Agents and Chemotherapy 1791 (1987) discusses compounds disclosed in European Patent Publications 127,902 and 184,170, discussed above, and compares these new compounds with known antibiotics.

U.S. Pat. No. 4,705,799 discloses aminomethyloxooxazolidinyl benzene derivatives including sulfides, sulfoxides, sulfones and sulfonamides which possess antibacterial activity.

U.S. Pat. No. 4,801,600 (WANG) discloses 6'-indolinyloxazolidinones (where the indolinyl nitrogen is meta to the oxazolidinone nitrogen) both generically, see formula (I) where "X" is NR$_6$ and specifically see Example 13. The indolinyloxazolidinones of the present invention are 5'-indolinyloxazolidinones (where the indolinyl nitrogen is para to the oxazolidinone nitrogen). Further, WANG discloses aminomethyloxooxazolidinyl cycloalkylbenzene derivatives including cycloalkyl-, alkanone-, hydroxycycloalkyl-, oxime-, amine- and other phenyloxazolidinones which possess antibacterial activity. More particularly, WANG discloses alkanone or indanone oxazolidinones generally, see formula (I) where R$_1$ and R$_2$ taken together are =O and specifically, see Examples 16, 26 and 30. All the indanoneoxazolidinones disclosed by WANG require the ketone (—CO—) to be attached directly to the phenyl ring in a position para to the oxazolidinone nitrogen. The indanoneoxazolidinones (XXIB) of the present invention differ from those of WANG. WANG also disclose oximinooxazolidinones, see Example 21 as well as the generic disclosure for R$_1$ and R$_2$ taken together to be =NOH.

SUMMARY OF THE INVENTION

Disclosed are 5'-indolinyloxazolidin-2-ones of formula (XI) where
(I) R$_1$ is —H,
C$_1$-C$_{12}$ alkyl optionally substituted with 1-3 Cl,
C$_3$-C$_{12}$ cycloalkyl,
C$_5$-C$_{12}$ alkenyl containing one double bond,
—$\phi$ optionally substituted with 1-3 —OH, —OCH$_3$, —OC$_2$H$_5$, —NO$_2$, —F, —Cl, —Br, —COOH and —SO$_3$H, —N(R$_{1-4}$)(R$_{1-5}$) where R$_{1-4}$ and R$_{1-5}$ are the same or different and are —H, C$_1$-C$_2$ alkyl,
furanyl,
tetrahydrofuranyl,
2-thiophene,
pyrrolidinyl,
pyridinyl,
—O—R$_{1-6}$ where R$_{1-6}$ is C$_1$-C$_4$ alkyl,
—NH$_2$,
—NHR$_{1-6}$ where R$_{1-6}$ is as defined above,
—NR$_{1-6}$R$_{1-7}$ where R$_{1-7}$ is C$_1$-C$_3$ alkyl and R$_{1-6}$ is as defined above, and where R$_{1-6}$ and R$_{1-7}$ can be taken together with the attached nitrogen atom to form a saturated mono-nitrogen C$_5$-C$_7$ heterocyclic ring including —O— (morpholine),
—CH$_2$—OH,
—CH$_2$—OR$_{1-8}$ where R$_{1-8}$ is C$_1$-C$_4$ alkyl or —CO—R$_{1-9}$ where R$_{1-9}$ is C$_1$-C$_4$ alkyl or —$\phi$;
(II) two of R$_2$, R$_3$ and R$_4$ are —H and the other of R$_2$, R$_3$ and R$_4$ is —H,
—F, —Cl, Br, —I,
C$_1$-C$_6$ alkyl,
—OH,
—CO—O—R$_{2-1}$ where R$_{2-1}$ is C$_1$-C$_4$ alkyl or —$\phi$,
—O—R$_{2-1}$ where R$_{2-1}$ is as defined above,
—COOH,
—COO$^-$,
—CHO,
—CO—NR$_{2-2}$R$_{2-3}$ where R$_{2-2}$ and R$_{2-3}$ are the same or different and are —H, C$_1$-C$_3$ alkyl, or R$_{2-2}$ and R$_{2-3}$ are taken together with the attached nitrogen atom to form a saturated mono-nitrogen C$_3$-C$_6$ heterocyclic ring optionally containing —O—,
—C≡N,
—C≡CH,
—N≡C,
—CHOH—CH$_3$,
—CO—CH$_3$,
—SH,
—SO—CH$_3$,
—SO—$\phi$,
—S—CH$_3$,
—S—$\phi$,
—SO$_2$—CH$_3$,
—SO$_2$—$\phi$,
—SO$_3$H,
—SO$_2$—NH$_2$,
—N$_3$,
—NO$_2$,
—NR$_{2-4}$R$_{2-5}$ where R$_{2-4}$ and R$_{2-5}$ are the same or different and are —H and C$_1$-C$_3$ alkyl,
—NH—CO—R$_{2-6}$ where R$_{2-6}$ is C$_1$-C$_4$ alkyl or —$\phi$,

—NH—CO—NH$_2$,
—CH=CH$_2$,
—CH$_2$—CH=CH$_2$,
—CH=N—OH,
—CH=N—OCH$_3$, $$-CH_3-\underset{|}{C}=N-OH,$$

$$-CH_3-\underset{|}{C}=N-OCH_3,$$

—C*H—CH$_2$—O* where the atoms marked with the asterisk (*) are bonded to each other resulting in the formation of a ring, where (III) R$_5$ is —H,
C$_1$-C$_{12}$ alkyl,
—CH$_2$—$\phi$,
—CH$_2$CH$_2$—$\phi$,
C$_3$-C$_7$ cycloalkyl,
C$_2$-C$_{12}$ alkenyl containing from 1 thru 3 double bonds,
C$_2$-C$_{12}$ alkynyl containing 1 triple bond,
—CHO,
—CO—R$_{5-1}$ where R$_{5-1}$ is
(A) C$_1$-C$_6$ alkyl optionally substituted with 1 —O—CH$_3$, —$\phi$, —COOH, —NH$_2$, —SO$_3$H or 1-3 —Cl,
(B) C$_3$-C$_7$ cycloalkyl,
(C) 2-pyridinyl, 2-thiophene, 2-thiophenemethyl or 2-pyrrole,
(D) —$\phi$ optionally substituted with 1-3
—F, —Cl, Br, —I,
C$_1$-C$_6$ alkyl,
—OH,
—CO—O—R$_{5-2}$ where R$_{5-2}$ is C$_1$-C$_4$ alkyl or —$\phi$,
—O—R$_{5-2}$ where R$_{5-2}$ is as defined above,
—COOH,
—CO—NR$_{5-3}$R$_{5-4}$ where R$_{5-3}$ and R$_{5-4}$ are the same or different and are —H, C$_1$-C$_3$ alkyl, or R$_{5-3}$ and R$_{5-4}$ are taken together with the attached nitrogen atom to form a saturated mononitrogen C$_3$-C$_6$ heterocyclic ring optionally containing —O—,
—C≡N,
—CHOH—CH$_3$,
—CO—CH$_3$,
—SH,
—SO—CH$_3$,
—SO—$\phi$,
—S—CH$_3$,
—S—$\phi$,
—SO$_2$—CH$_3$,
—SO$_2$—$\phi$,
—SO$_3$H,
—SO$_2$—NH$_2$,
—N$_3$,
—NO$_2$,
—NR$_{5-5}$R$_{5-6}$ where R$_{5-5}$ and R$_{5-6}$ are the same or different and are —H and C$_1$-C$_3$ alkyl,
—NH—CO—R$_{5-7}$ where R$_{5-7}$ is C$_1$-C$_4$ alkyl or —$\phi$,
—CO—O—R$_{5-8}$ where R$_{5-8}$ is C$_1$-C$_4$ alkyl or —$\phi$ either optionally substituted with 1 or 2
—F, —Cl, Br, —I,
C$_1$-C$_6$ alkyl,
—OH,
—CO—O—R$_{5-2}$ where R$_{5-2}$ is as defined above, —O—R$_{5-2}$ where R$_{5-2}$ is as defined above,
—COOH,
—CO—NR$_{5-3}$R$_{5-4}$ where R$_{5-3}$ and R$_{5-4}$ are as defined above,
—C≡N,
—CHOH—CH$_3$,
—CO—CH$_3$,
—SH,
—SO—CH$_3$,
—SO—$\phi$,
—S—CH$_3$,
—S—$\phi$,
—SO$_2$—CH$_3$,
—SO$_2$—$\phi$,
—SO$_3$H,
—SO$_2$—NH$_2$,
—N$_3$,
—NO$_2$,
—NR$_{5-5}$R$_{5-6}$ where R$_{5-5}$ and R$_{5-6}$ are as defined above,
—NH—CO—R$_{5-7}$ where R$_{5-7}$ is as defined above,
—CO—N(R$_{5-9}$)$_2$ where R$_{5-9}$ is —H or R$_{5-8}$ as defined above and where the R$_{5-9}$'s can be taken together with the attached nitrogen atom to form a saturated mononitrogen C$_3$-C$_6$ heterocyclic ring optionally containing —O— or —NH—,
—CO—CH$_2$—CN,
—CO—CH$_2$—OH,
—CO—CH$_2$—O—$\phi$ where $\phi$ is optionally substituted with 1-3 —O—CH$_3$, 1 —NO$_2$ and 1 —NH$_2$,
—CO—CH$_2$—O—R$_{5-10}$ where R$_{5-10}$ is
C$_1$-C$_6$ alkyl optionally substituted with —$\phi$,
—$\phi$ optionally substituted with 1-3 —O—CH$_3$, 1 —NO$_2$ and —NH$_2$,
—CO—R$_{5-11}$ where R$_{5-11}$ is C$_1$-C$_6$ alkyl, —$\phi$ optionally substituted with 1-4 —F, 1-3 —Cl, 1 —OCH$_3$, —OH, —NH$_2$, —NO$_2$, —CO—CH$_3$, —SO$_2$—CH$_3$ and —SO$_2$—OH,
—CO—CH(NH—CO—R$_{5-12}$)—R$_{5-13}$ where R$_{5-13}$ is —H or —CH$_3$ and R$_{5-12}$ is C$_1$-C$_6$ alkyl, —$\phi$ optionally substituted with 1 or 2 —OH, —OCH$_3$, —NO$_2$, —NH$_2$, —Cl, —F, —NH—CH$_3$ and —N(CH$_3$)$_2$,
—CO—CHNH$_2$—R$_{5-14}$ where R$_{5-15}$ is —CH(CH$_3$)$_2$, —CH$_2$—CH(CH$_3$)$_2$, —CHCH$_3$—CH$_2$—CH$_3$, —CH$_2$—OH, —CH(OH)—CH$_3$, —CH$_2$—$\phi$, —CH$_2$—$\phi$—OH, —CH$_2$—SH, —CH$_2$—CH$_2$—S—CH$_3$, and —CH$_2$—COOH,
—SO$_2$—CH$_3$,
—SO$_2$—$\phi$,
—SO$_3$H,
and R$_6$ is —H and C$_1$-C$_3$ alkyl and pharmaceutically acceptable salts thereof.

Further disclosed are compounds selected from the group consisting of a 5'-indolinyloxazolidin-2-ones of formula (XIII) where
X$_1$ is —CO—CH$_3$, —CO—O—C(CH$_3$)$_3$, —CO—O—CH$_2$—$\phi$ and —CO—O—(CH$_2$)$_2$—Si(CH$_3$)$_3$,
R$_6$ is —I, —N$_3$ and —NH$_2$ and where R$_2$, R$_3$ and R$_4$ are as defined above, and salts thereof.

Disclosed are 3-(fused-ring substituted)phenyl-5$\beta$-amidomethyloxazolidin-2-ones of formula (XXI) where
(I) R$_1$ is —H,
C$_1$-C$_{12}$ alkyl optionally substituted with 1-3 Cl,
C$_3$-C$_{12}$ cycloalkyl,
C$_5$-C$_{12}$ alkenyl containing one double bond,
—$\phi$ substituted with 1-3 —OH, —OCH$_3$, —OC$_2$H$_5$, —NO$_2$, —F, —Cl, —Br, —COOH and —SO$_3$H, —N(-

$R_{1-9})(R_{1-10})$ where $R_{1-9}$ and $R_{1-10}$ are the same or different and are —H, $C_1$-$C_2$ alkyl,
  furanyl,
  tetrahydrofuranyl,
  2-thiophene,
  pyrrolidinyl,
  pyridinyl,
  —O—$R_{1-4}$ where $R_{1-4}$ is $C_1$-$C_4$ alkyl,
  —$NH_2$,
  —$NHR_{1-4}$ where $R_{1-4}$ is as defined above,
  —$NR_{1-4}R_{1-5}$ where $R_{1-5}$ is $C_1$-$C_3$ alkyl and $R_{1-4}$ is as defined above, and where $R_{1-4}$ and $R_{1-5}$ can be taken together with the attached nitrogen atom to form a saturated mono-nitrogen $C_5$-$C_7$ heterocyclic ring including —O— (morpholine).
  —$CH_2$—OH,
  —$CH_2$—$OR_{1-6}$ where $R_{1-6}$ is $C_1$-$C_4$ alkyl or —CO—$R_{1-7}$ where $R_{1-7}$ is $C_1$-$C_4$ alkyl or —$\phi$;
(II) either $R_2$ or $R_4$ is —H and the other of $R_2$ and $R_4$ taken together with $R_3$ is $$-(CH_2)_{n3}-(CR_{10-1}R_{10-2})_{n7}-CO-(CHR_{10-3}R_{10-4})_{n8}-(CH_2)_{n4}-$$

where $n_3$ and $n_4$ are 0–3, $n_7$ and $n_8$ are 0 or 1, $R_{10-1}$ and $R_{10-2}$ are the same or different and are —H, $C_1$-$C_3$ alkyl and where $R_{10-1}$ and $R_{10-2}$ taken together with the carbon atom to which they are attached form spirocyclopropyl, $R_{10-3}$ and $R_{10-4}$ are the same or different and are —H, $C_1$-$C_3$ alkyl and where $R_{10-3}$ and $R_{10-4}$ taken together with the carbon atom to which they are attached form spirocyclopropyl, with the provisos that (1) $n_7+n_8=0$ or 1, (2) $n_3+n_4+n_7+n_8 = 2$ or 3 and (3) when $n_4$ is 0, either (a) $n_8=1$ or (b) $n_7=1$ and one of $R_{10-1}$ or $R_{10-2}$ is not —H;

$$-(CH_2)_{n5}-CH=CH-(CH_2)_{n6}-$$

where $n_5$ and $n_6$ are 0–2 with the proviso than $n_5+n_6=1$ or 2;

$$-(CH_2)_{n3}-(CR_{10-1}R_{10-2})_{n7}-C(=N-OR_7)-(CHR_{10-3}R_{10-4})_{n8}-(CH_2)_{n4}-$$

where $R_7$ is —H, $C_1$-$C_4$ alkyl, —$CH_2$—COOH or —$CH_2$—COO—$R_{7-1}$ where $R_{7-1}$ is $C_1$-$C_4$ alkyl and where $CR_{10-1}$, $R_{10-2}$, $CR_{10-3}$, $R_{10-4}$, $n_3$, $n_4$, $n_7$ and $n_8$ are as defined above including the provisos (1) that $n_7+n_8=0$ or 1, (2) $n_3+n_7+n_8=2$ or 3, and (3) when $n_3$ is 0, either (a) $n_7=1$ or (b) $n_8=1$ and one or $R_{10-1}$ or $R_{10-2}$ is not —H;

(III) one of $R_5$ and $R_6$ is —H and the other of $R_5$ and $R_6$ is —H,
  $C_1$-$C_{12}$ alkyl,
  —$CH_2$—$\phi$,
  —$CH_2CH_2$—$\phi$,
  $C_3$-$C_7$ cycloalkyl,
  $C_2$-$C_{12}$ alkenyl containing from 1 thru 3 double bonds,
  $C_2$-$C_{12}$ alkynyl containing 1 triple bond,
  —CHO,
  —CO—$R_{5-1}$ where $R_{5-1}$ is
    (A) $C_1$-$C_6$ alkyl optionally substituted with 1 —O—$CH_3$, —COOH, —$NH_2$, —$SO_3H$ or 1–3 —Cl,
    (B) $C_3$-$C_7$ cycloalkyl,
    (C) 2-pyridinyl, 2-thiophene, 2-thiophenemethyl or 2-pyrrole,
    (D) —$\phi$ optionally substituted with 1–3
      —F, —Cl, Br, —I,
      $C_1$-$C_6$ alkyl,
      —OH,
      —CO—O—$R_{5-2}$ where $R_{5-2}$ is $C_1$-$C_4$ alkyl or —$\phi$,
      —O—$R_{5-2}$ where $R_{5-2}$ is as defined above,
      —COOH,
      —CO—$NR_{5-3}R_{5-4}$ where $R_{5-3}$ and $R_{5-4}$ are the same or different and are —H, $C_1$-$C_3$ alkyl, or $R_{5-3}$ and $R_{5-4}$ are taken together with the attached nitrogen atom to form a saturated mononitrogen $C_3$-$C_6$ heterocyclic ring optionally containing —O—,
      —C≡N,
      —CHOH—$CH_3$,
      —CO—$CH_3$,
      —SH,
      —SO—$CH_3$,
      —SO—$\phi$,
      —S—$CH_3$,
      —S—$\phi$,
      —$SO_2$—$CH_3$,
      —$SO_2$—$\phi$,
      —$SO_3H$,
      —$SO_2$—$NH_2$,
      —$N_3$,
      —$NO_2$,
      —$NR_{5-5}R_{5-6}$ where $R_{5-5}$ and $R_{5-6}$ are the same or different and are —H and $C_1$-$C_3$ alkyl,
      —NH—CO—$R_{5-7}$ where $R_{5-7}$ is $C_1$-$C_4$ alkyl or —$\phi$,
      —CO—O—$R_{5-8}$ where $R_{5-8}$ is $C_1$-$C_4$ alkyl or —$\phi$
    either optionally substituted with 1 or 2
      —F, —Cl, Br, —I,
      $C_1$-$C_6$ alkyl,
      —OH,
      —CO—O—$R_{5-2}$ where $R_{5-2}$ is as defined above,
      —O—$R_{5-2}$ where $R_{5-2}$ is as defined above,
      —COOH,
      —CO—$NR_{5-3}R_{5-4}$ where $R_{5-3}$ and $R_{5-4}$ are as defined above,
      —C≡N,
      —CHOH—$CH_3$,
      —CO—$CH_3$,
      —SH,
      —SO—$CH_3$,
      —SO—$\phi$,
      —S—$CH_3$,
      —S—$\phi$,
      —$SO_2$—$CH_3$,
      —$SO_2$—$\phi$,
      —$SO_3H$,
      —$SO_2$—$NH_2$,
      —$N_3$,
      —$NO_2$,
      —$NR_{5-5}R_{5-6}$ where $R_{5-5}$ and $R_{5-6}$ are as defined above,
      —NH—CO—$R_{5-7}$ where $R_{5-7}$ is as defined above,
      —CO—$N(R_{5-9})_2$ wherein $R_{5-9}$ is or $R_{5-8}$ as defined above and where the $R_{5-9}$'s can be taken together with the attached nitrogen atom to form a saturated mononitroen $C_3$-$C_6$ heterocyclic ring optionally containing —O— or —NH—,
      —CO—$CH_2$—CN,
      —CO—$CH_2$—OH,
      —CO—$CH_2$—O—$\phi$ where $\phi$ is optionally substituted with 1–3 —O—$CH_3$, 1 —$NO_2$ and 1 —$NH_2$,
      —CO—$CH_2$—O—$R_{5-10}$ where $R_{5-10}$ is $C_1$-$C_6$ alkyl,
      —$\phi$ optionally substituted with 1–3 —O—$CH_3$, 1 —$NO_2$ and —$NH_2$,
      —CO—$R_{5-11}$ where $R_{5-11}$ is $C_1$-$C_6$ alkyl, —$\phi$ optionally substituted with 1–4 —F, 1–3 —Cl, 1 —$OCH_3$, —OH, —NH$_2$, —NO$_2$, —CO—CH$_3$, —SO$_2$—CH$_3$ and —SO$_2$—OH,
—CO—CH(NH—CO—R$_{5\text{-}12}$)—R$_{5\text{-}13}$ is —H or —CH$_3$ and R$_{5\text{-}12}$ is C$_1$-C$_6$ alkyl, —φ optionally substituted with 1 or 2 —OH, —OCH$_3$, —NO$_2$, NH$_2$, —Cl, F, —NH—CH$_3$ and —N(CH$_3$)$_2$,
—CO—CHNH$_2$—R$_{5\text{-}14}$ where R$_{5\text{-}14}$ is —CH(CH$_3$)$_2$, —CH$_2$—CH(CH$_3$)$_2$, —CHCH$_3$—CH$_2$—CH$_3$, —CH$_2$—OH, —CH(OH)—CH$_3$, —CH$_2$—φ, —CH$_2$—φ—OH, —CH$_2$—φ—OH, —CH$_2$—SH, —CH$_2$—CH$_2$—S—CH$_3$, and —CH$_2$—COOH,
—SO$_2$—CH$_3$,
—SO$_2$—φ,
—SO$_3$H,
and R$_6$ is —H and C$_1$-C$_3$ alkyl and pharmaceutically acceptable salts thereof.

Disclosed are 3-(nitrogen substituted)phenyl-5β-(amidomethyl)oxazolidin-2-ones of formula (LV) where (I) R$_1$ is —H,
C$_1$-C$_{12}$ alkyl optionally substituted with 1-3 Cl,
C$_3$-C$_{12}$ cycloalkyl,
C$_5$-C$_{12}$ alkenyl containing one double bond,
—φ optionally substituted with 1-3 —OH, —OCH$_3$, —OC$_2$H$_5$, —NO$_2$, —F, —Cl, —Br, —COOH and —SO$_3$H, —N(R$_{1\text{-}1}$)(R$_{1\text{-}2}$) where R$_{1\text{-}1}$ and R$_{1\text{-}2}$ are the same or different and are —H, C$_1$-C$_2$ alkyl,
furanyl,
tetrahydrofuranyl,
2-thiophene,
pyrrolidinyl,
pyridinyl,
—O—R$_{1\text{-}3}$ where R$_{1\text{-}3}$ is C$_1$-C$_4$ alkyl,
—NH$_2$,
—NHR$_{1\text{-}3}$ where R$_{1\text{-}3}$ is as defined above,
—NR$_{1\text{-}3}$R$_{1\text{-}4}$ where R$_{1\text{-}4}$ is C$_1$-C$_3$ alkyl and R$_{1\text{-}3}$ is as defined above, and where R$_{1\text{-}3}$ and R$_{1\text{-}4}$ can be taken together with the attached nitrogen atom to form a saturated mono-nitrogen C$_5$-C$_7$ heterocyclic ring including —O— (morpholine),
—CH$_2$—OH,
—CH$_2$—OR$_{1\text{-}5}$ where R$_{1\text{-}5}$ is C$_1$-C$_4$ alkyl or —CO—R$_{1\text{-}6}$ where R$_{1\text{-}6}$ is C$_1$-C$_4$ alkyl or —φ;

(II) two of R$_2$, R$_3$ and R$_4$ are —H and the other of R$_2$, R$_3$ and R$_4$ is —H,
—F, —Cl, Br, —I,
C$_1$-C$_6$ alkyl,
—OH,
—CO—O—R$_{2\text{-}1}$ where R$_{2\text{-}1}$ is C$_1$-C$_4$ alkyl or —φ,
—O—R$_{2\text{-}1}$ where R$_{2\text{-}1}$ is as defined above,
—COOH,
—COO$^-$,
—CHO,
—CO—NR$_{2\text{-}2}$R$_{2\text{-}3}$ where R$_{2\text{-}2}$ and R$_{2\text{-}3}$ are the same or different and are —H, C$_1$-C$_3$ alkyl, or R$_{2\text{-}2}$ and R$_{2\text{-}3}$ are taken together with the attached nitrogen atom to form a saturated mono-nitrogen C$_3$-C$_6$ heterocyclic ring optionally containing —O—.
—C≡N,
—C≡CH,
—N≡C,
—CHOH—CH$_3$,
—CO—CH$_3$,
—SH,
—SO—CH$_3$,
—SO—φ,
—S—CH$_3$,
—S—φ,
—SO$_2$—CH$_3$,
—SO$_2$—φ,
—SO$_3$H,
—SO$_2$—NH$_2$,
—N$_3$,
—NO$_2$,
—NR$_{2\text{-}4}$R$_{2\text{-}5}$ where R$_{2\text{-}4}$ and R$_{2\text{-}5}$ are the same or different and are —H and C$_1$-C$_3$ alkyl,
—NH—CO—R$_{2\text{-}6}$ where R$_{2\text{-}6}$ is C$_1$-C$_4$ alkyl or —φ,
—NH—CO—NH$_2$,
—CH=CH$_2$,
—CH$_2$—CH=CH$_2$,
—CH=N—OH,
—CH=N—OCH$_3$,

—CH$_3$—C=N—OH,
          |

—CH$_3$—C=N—OCH$_3$,
          |

—C*H—CH$_2$—O* where the atoms marked with the asterisk (*) are bonded to each other resulting in the formation of a ring,
(IIIA) where W$_1$ and W$_2$ taken together are

—NR$_5$—N=CR$_6$—   (XXXII)

where
R$_5$ is —H,
C$_1$-C$_{12}$ alkyl,
—CH$_2$—φ,
—CH$_2$CH$_2$—φ,
C$_3$-C$_7$ cycloalkyl,
C$_2$-C$_{12}$ alkenyl containing from 1 thru 3 double bonds,
C$_2$-C$_{12}$ alkynyl containing 1 triple bond,
—CHO,
—CO—R$_{5\text{-}1}$ where R$_{5\text{-}1}$ is
(A) C$_1$-C$_6$ alkyl optionally substituted with 1 —O—CH$_3$, —COOH, —NH$_2$, —SO$_3$H or 1-3 —Cl,
(B) C$_3$-C$_7$ cycloalkyl,
(C) 2-pyridinyl, 2-thiophene, 2-thiophenemethyl or 2-pyrrole,
(D) —φ optionally substituted with 1-3
—F, —Cl, Br, —I,
C$_1$-C$_6$ alkyl,
—OH,
—CO—O—R$_{5\text{-}2}$ where R$_{5\text{-}2}$ is C$_1$-C$_4$ alkyl or —φ,
—O—R$_{5\text{-}2}$ where R$_{5\text{-}2}$ is as defined above,
—COOH,
—CO—NR$_{5\text{-}3}$R$_{5\text{-}4}$ where R$_{5\text{-}3}$ and R$_{5\text{-}4}$ are the same or different and are —H, C$_1$-C$_3$ alkyl, or R$_{5\text{-}3}$ and R$_{5\text{-}4}$ are taken together with the attached nitrogen atom to form a saturated mononitrogen C$_3$-C$_6$ heterocyclic ring optionally containing —O—,
—C≡N,
—CHOH—CH$_3$,
—CO—CH$_3$,
—SH,
—SO—CH$_3$,
—SO—φ,
—S—CH$_3$,
—S—φ, $-SO_2-CH_3$,
$-SO_2-\phi$,
$-SO_3H$,
$-SO_2-NH_2$,
$-N_3$,
$-NO_2$,
$-NR_{5-5}R_{5-6}$ where $R_{5-5}$ and $R_{5-6}$ are the same or different and are $-H$ and $C_1-C_3$ alkyl,
$-NH-CO-R_{5-7}$ where $R_{5-7}$ is $C_1-C_4$ alkyl or $-\phi$,
$-CO-O-R_{5-8}$ where $R_{5-8}$ is $C_1-C_4$ alkyl or $-\phi$ either optionally substituted with 1 or 2
$-F$, $-Cl$, $Br$, $-I$,
$C_1-C_6$ alkyl,
$-OH$,
$-CO-O-R_{5-2}$ where $R_{5-2}$ is as defined above,
$-O-R_{5-2}$ where $R_{5-2}$ is as defined above,
$-COOH$,
$-CO-NR_{5-3}R_{5-4}$ where $R_{5-3}$ and $R_{5-4}$ are as defined above,
$-C\equiv N$,
$-CHOH-CH_3$,
$-CO-CH_3$,
$-SH$,
$-SO-CH_3$,
$-SO-\phi$,
$-S-CH_3$,
$-S-\phi$,
$-SO_2-CH_3$,
$-SO_2-\phi$,
$-SO_3H$,
$-SO_2-NH_2$,
$-N_3$,
$-NO_2$,
$-NR_{5-5}R_{5-6}$ where $R_{5-5}$ and $R_{5-6}$ are as defined above,
$-NH-CO-R_{5-7}$ where $R_{5-7}$ is as defined above,
$-CO-N(R_{5-9})_2$ where $R_{5-9}$ is $-H$ or $R_{5-8}$ as defined above and where the $R_{5-9}$'s can be taken together with the attached nitrogen atom to form a saturated mononitrogen $C_3-C_6$ heterocyclic ring optionally containing $-O-$ or $-NH-$,
$-CO-CH_2-CN$,
$-CO-CH_2-OH$,
$-CO-CH_2-O-\phi$ where $\phi$ is optionally substituted with 1-3 $-O-CH_3$, 1 $-NO_2$ and 1 $-NH_2$,
$-CO-CH_2-O-R_{5-10}$ where $R_{5-10}$ is $C_1-C_6$ alkyl, $-\phi$ optionally substituted with 1-3 $-O-CH_3$, 1 $-NO_2$ and $-NH_2$,
$-CO-R_{5-11}$ where $R_{5-11}$ is $C_1-C_6$ alkyl, $-\phi$ optionally substituted with 1-4 $-F$, 1-3 $-Cl$, 1 $-OCH_3$, $-OH$, $-NH_2$, $-NO_2$, $-CO-CH_3$, $-SO_2-CH_3$ and $-SO_2-OH$,
$-CO-CH(NH-CO-R_{5-12})-R_{5-13}$ where $R_{5-13}$ is $-H$ or $-CH_3$ and $R_{5-12}$ is $C_1-C_6$ alkyl, $-\phi$ optionally substituted with 1 or 2 $-OH$, $-OCH_3$, $-NO_2$, $-NH_2$, $-Cl$, $-F$, $-NH-CH_3$ and $-N(CH_3)_2$,
$-CO-CHNH_2-R_{5-14}$ where $R_{5-14}$ is $-CH(CH_3)_2$, $-CH_2-CH(CH_3)_2$, $-CHCH_3-CH_2-CH_3$, $-CH_2-OH$, $-CH(OH)-CH_3$, $-CH_2-\phi$, $-CH_2-\phi-OH$, $-CH_2-SH$, $-CH_2-CH_2-S-CH_3$, and $-CH_2-COOH$,
$-SO_2-CH_3$,
$-SO_2-\phi$,
$-SO_3H$,
and $R_6$ is $-H$ and $C_1-C_3$ alkyl;
(IIIB) where $W_1$ and $W_2$ taken together are $$-NR_5-CR_6=N- \qquad (XLIII)$$

where $R_5$ is as defined above and $R_6$ is $-H$, $C_1-C_6$ alkyl, $-SH$, $-S-CH_3$, $-S-C_2H_5$, $-S-\phi$, $-S-OCH_3$, $-S-O-\phi$, $-SO_2-CH_3$ and $-SO_2-\phi$, (IIIC) where $W_1$ and $W_2$ taken together are $$-NR_5-N=N- \qquad (LIV)$$

where $R_5$ is as defined above and pharmaceutically acceptable salts thereof.

DETAILED DESCTIPTION OF THE INVENTION

The 5′-indolinyloxazolidin-2-ones (XI) are prepared starting with the corresponding 5-nitroindolines (I). It is preferred that $R_2$, $R_3$ and $R_4$ all be $-H$. The indolinyl nitrogen of the 5-nitroindolines (I) is protected to produce the corresponding protected 5-nitroindolines (II). Suitable protecting agents, $X_1$, include t-butyloxycarbonyl (BOC), acetyl, $-CO-O-CH_2-\phi$ and $-CO-O-(CH_2)_2-Si(CH_3)_3$. It is preferred that $X_1$ be t-butyloxycarbonyl. Next, the nitro group of the protected 5-nitroindolines (II) is reduced with hydrogen and an appropriate catalyst such as palladium on carbon to the corresponding protected 5-aminoindolines (III). Acylation of the free unprotected 5-amino group of the 1-protected 5-aminoindolines (III) with a carbobenzyloxy (CBZ) group gives the urethanes (IV). The urethanes (IV) are then reacted with $Br-CH_2-CH=CH_2$ in THF and a base forming the N-allyl-N-CBZ compounds (V). Suitable bases includes sodium hydride, sodium methoxide, potassium tertiary butoxide and lithium diisopropylamide; preferred is sodium hydride. The N-allyl-N-CBZ compounds (V) are cyclized to form the oxidation nucleus by reaction with an electrophilic agent. Suitable electrophilic agents include bromine and iodine; iodine in chloroform is preferred. The oxazolidinone nucleus formed is the protected 5-iodomethyloxazolidin-2-one (VI). Following formation of the oxazolidinone ring, the desired side chain at the 5-position is formed by reacting the protected 5-iodomethyl oxazolidinones (VI) with an azide to form the protected azides (VII). The protected azides (VII) are reduced with hydrogen in the presence of a catalyst such as palladium or by $P\phi_3$ or $H_2S$ or other methods known to those skilled in the art to give racemic protected 5-aminomethyloxazolidin-2-ones (VIII). The racemic compounds can be resolved at the aminomethyloxazolidinone (VIII) stage using methods known to those skilled in the art, see for example, Optical Resolution Procedures for Chemical Compounds, Vol. 1,: Amines and Related Compounds, Paul Newman, Optical Resolution Information Center, Manhattan College, Riverdale, N.Y., 10471, 1978. For example, treatment of the d,1-aminomethyloxazolidinone (VIII) mixture with an optically active acid such as (+)-tartaric acid or alternatively with (−)-tartaric acid, would yield a mixture of diastereomeric salts, which can be separated most convientty by fractional crystallization to give a salt containing only one enantiomer of the reacemic mixture. Other suitable optically active acids include (−) dibenzoyltartaric acid, (+)-camphoric acid, (+)- and (−)-malic acid and (+)-camphor-10-sulfonic acid. By reacting the diastereomeric salt with a base one obtains the enantiomer as the free compound. These compounds are then acylated to produce the protected 5′-indolinyloxazolidin-2-ones (IX) containing the desired $R_1$ group. It is preferred that $R_1$ is H, $C_1-C_6$ alkyl, $C_3$-$C_6$ cycloalkyl, $-OCH_3$ and $-CHCl_2$; it is more preferred that $R_1$ is $-CH_3$. Acid hydrolysis of the (BOC) protected 5'-indolinyloxazolidi-2-nones (IX) produces the unprotected 5'-indolinyloxazolidin-2-ones (X) which are then N-acylated or N-alkylated, if necessary, with the desired $R_5$ group, either as the acid halide, anhydride, or through a reductive alkylation sequence to produce the desired 5'-indolinyloxazolidin-2-ones (XI). The CBZ protecting group is removed by hydrogen with palladium on carbon and the $-CO-O-(CH_2)_2-Si(CH_3)_3$ is removed by tetrabutylammonium fluoride, see J. Chem. Soc. Chem. Commun., 358 (1970). For the 5'-indolinyloxazolidin-2-ones (XI), it is preferred that $R_5$ is $-CH_3$, $-CH_2-CH=CH_2$, $-CH_2-C\equiv CH$, $-CHO$, $-CO-R_{5-1}$ where $R_{5-1}$ is $-CH_3$, $-C_2H_5$, $-CH(CH_3)_2$, $-CH_2Cl$, $-CHCl_2$, $-CH_2-OH$, $-CH_2-O-CH_3$, 2-thienyl and cyclopropyl. It is more preferred that $R_5$ is $-CH_3$, $-CH_2-CH=CH_2$, $-CHO$, $-CO-R_{5-1}$ where $R_{5-1}$ is $-CH_3$, $-C_2H_5$, $-CHCl_2$, $-CH_2-OH$ and 2-thienyl.

The 3-(fused-ring substituted)phenyl-5$\beta$-amidomethyloxazolidin-2-ones (XXI) are prepared by methods known to those skilled in the art from known starting compounds. See, for example, European Patent Publications 127,902 and 184,170; Antimicrobial Agents and Chemotherapy 1791 (1987) and Tetrahedron 43, 2505 (1987).

The 3-(fused-ring substituted)phenyl-5$\beta$-amidomethyloxazolidin-2-ones (XXI) of the present invention include the fused alkanonephenyloxazolidinones (B), the fused cycloalkenylphenyloxazolidinones (D), and the fused oximinocycloalkylphenyl-oxazolidinones (E), see CHART C. It is fused that the 3-(fused-ring substituted)phenyl-5$\beta$-amidomethyloxazolidinones (XXI) are the fused alkanonephenyloxazolidinones (B) and the fused oximinocycloalkylphenyloxazolidinones (E). It is more preferred that the 3-(fused-ring substituted)phenyl-5$\beta$-amidomethyloxazolidin-2-ones (XXI) are the fused alkanonephenyloxazolidin-2-ones (B).

The oxazolidinone nucleus is formed by starting with an appropriately substituted aniline (XV) containing the desired $R_2/R_3/R_4$ moiety (see CHART C) or one which can readily be transformed to the desired moiety. The oxazolidinone ring system is synthesized after protecting the aniline (XV) nitrogen with a carbobenzyloxy (CBZ) group. Acylation of the aniline (XV) nitrogen atom gives the urethane (XVI). The urethane (XVI) is then reacted with $Br-CH_2-CH=CH_2$ in THF and a base forming an N-allyl-N-CBZ compound (XVII). Suitable bases include sodium hydride, sodium methoxide, potassium tertiary butoxide and lithium diisopropylamide; preferred is sodium hydride. The N-allyl-N-CBZ compound (XVII) is cyclized to form the oxazolidinone nucleus by reaction with an electrophilic agent. Suitable electrophilic agents include bromine and iodine; iodine in chloroform is preferred. The oxazolidinone nucleus formed is the 5-iodomethyloxazolidin-2-one (XVIII). When the phenyl substituent contains a chiral center then the oxazolidinone ring has two different substituents at the $C_5$ position and therefore produces two diastereomers. These can be separated by crystallization or chromatography. Following formation of the oxazolidinone ring, the desired side chain at the 5-position is formed by reacting the iodomethyloxazolidin-2-one (XVIII) with an azide to form the azide (XIX). The azide is reduced with hydrogen in the presence of a catalyst such as palladium or by $P\phi_3$ or $H_2S$ or other methods known to those skilled in the art to give the 5-aminomethyl oxazolidinone as the N-appropriately substituted-3-phenyl-5-aminomethyloxazolidin-2-one (XX). This compound is then acylated to give the desired $R_1$ group. It is preferred that $R_1$ is $-H$, $C_1$-$C_6$ alkyl, $C_3$-$C_6$ cycloalkyl, $-OCH_3$, $-CHCl_2$ and $-CH_2Cl$; it is more preferred that $R_1$ is $-CH_3$.

This process is operative regardless of whether the 3-(fused-ring substituted)phenyl-5-amidomethyloxazolidin-2-one (XXI) has a five or six member ring attached to the phenyl group.

Both the 2,3- and 3,4- indanyl (5 member alkyl ring) and the 2,3- and 3,4- six member alkyl rings of the fused cycloalkylphenyloxazolidin-2-ones (XXIA), are prepared by starting with the appropriately substituted aniline (XVA). It is preferred than $n_2$ is 3 or 4.

The 2,3- and 3,4- fused alkanonephenyloxazolidin-2-ones (XXIB), are prepared following the procedure for the preparation of the fused cycloalkylphenyloxazolidin-2-ones (XXIA). The alkyl aniline intermediate (XVA) is first oxidized to the corresponding alkanone aniline (XVB) by known procedures. See for example, J. Org. Chem., 27, 70 (1962). The amino group is protected, for example as the acetamide, and then the protected aniline (XVA) is oxidized to the corresponding protected alkanone aniline (XVB) with an oxidizing agent such as chromium trioxide in acetic acid and acetone. The deprotected alkanonephenyl aniline (XVB) is then reacted just as the corresponding alkyl aniline (XVA) to produce the corresponding alkanone (XXIB). It may be necessary to protect the ketone functionality as the ketal with ethylene glycol, for example, followed by deprotection with acid treatment at a later stage. For the 3,4- substitution, with a para ketone, with either the 5 or 6 member ring, alternatively and preferably, the fused cycloalkylphenyloxazolidin-2-one (XXIA) product can be oxidized with an oxidizing agent such as chromium trioxide in acetic acid and acetic anhydride directly to the corresponding fused alkanonephenyloxazolidin-2-one (XXIB) product. When the ketone ring has a substituent on the carbon atom next to the carbonyl group (either $R_{10-1}$, $R_{10-2}$, $R_{10-3}$ or $R_{10-4}$ is not $-H$) the compounds are prepared by either starting with the appropriately substituted aniline intermediate (XVB) or by alkylation of the ketone (XXIB) or enamine (XXIH) at a later stage in the synthesis as is known to those skilled in the art. When the alkylation reaction is performed, it produces both the mono- and dialkylated products. If the alkanonephenyloxazolidin-2-one (XXIB) is alkylated; it is preferred that the alkanonephenyloxazolidin-2-one (XXIB) be monoalkylated rather than dialkylated. It is preferred that $n_3+n_4+n_7+n_8=2$ or 3. It is preferred that $R_{10-3}$ is $-CH_3$ or $-CH_2-OH$ and where $R_{10-3}$ and $R_{10-4}$ are taken together to form cyclopropyl. It is more preferred that $R_{10-1}$ is $-CH_3$.

The fused hydroxycycloalkylphenyloxazolidin-2-ones (XXIC) are prepared from the corresponding fused alkanonephenyloxazolidin-2-ones (XXIB) by reduction with a reducing agent such as sodium borohydride, sodium cyanoborohydride, lithium borohydride, lithium tri-secbutylborohydride, etc. The reduction of the ketone to the corresponding secondary alcohol produces two diastereomers which can be separated by chromatography or crystallization. Both of the diastereomers have the desired antibacterial activity, though in some cases to different degrees. It is preferred that $n_3+n_4=2$ or 3. Treatment of the alcohol with a base such as sodium hydride in the presence of an alkylating agent such as an alkyl iodide or epoxide, results in the formation of the corresponding ether, —CH(—OR)—, as is known to those skilled in the art. The fused cycloalkenylphenyloxazolidin-2-ones (XXID) are preferably produced by the procedure of CHART D starting with the desired amino indene or amino dihydronaphthalene (XVID). Alternatively, the indenes (XXID) are produced by dehydration (alcohol elimination) of the corresponding indanol (XXIC). Suitable reagents for the dehydration include $(CF_3—CO)_2O$, $CH_3—SO_2—Cl$ or $(CF_3SO_2)_2O$ and triethylamine. Dehydration of a benzylic substituted fused hydroxycycloalkylphenyloxazolidinone (C) will result in the production of just one fused cycloalkenylphenyloxazolidinone (D). However, with a non-benzylic fused hydroxycycloalkylphenyloxazolidinone (C), two dehydration products are produced. Both are within the scope of the invention. It is preferred that $n_5+n_6=1$ or 2.

The fused oximinocycloalkylphenyloxazolidin-2-ones (XXIE) are prepared from the corresponding fused alkanonephenyloxazolidin-2-ones (XXIB) by reaction with hydroxylamine ($R_7$ is —H) hydrochloride or a substituted hydroxylamine ($R_7$ is not —H) hydrochloride in the presence of a base such as pyridine or sodium bicarbonate.

Once the aminomethyloxazolidin-2-ones (XX) are obtained various analogues and/or derivatives can readily be prepared by acylation. For pharmacological activity it is necessary that the 5-amidomethyl side chain be in the β configuration; hence, the —H at $C_5$ must be in the α configuration. It is preferred that $R_1$ be —CH$_3$ and —OCH$_3$, —CHCl$_2$ and $C_3$-$C_6$ cycloalkyl; it is more preferred that $R_1$ be —CH$_3$.

The synthesis of the indazolyloxazolidin-2-ones (XXXII) starts with the appropriate nitroindazole (XXII). It is preferred that $R_2$, $R_3$ and $R_4$ be —H. It is preferred that $R_6$ is —H or —CH$_3$. The indazolyl nitrogen of the nitroindazoles (XXII) is protected, as previously discussed, to produce the corresponding protected nitroindazoles (XXIII). It is preferred that $X_1$ be t-butyloxycarbonyl. Next, the nitro group of the protected nitroindazoles (XXIII) is reduced with hydrogen, as previously discussed, to the corresponding protected aminoindazoles (XXIV). Acylation of free unprotected amino group of the protected aminoindazoles (XXIV) with a carbobenzyloxy (CBZ) group gives the urethanes (XXV). The urethanes (XXV) are then reacted with Br—CH$_2$—CH=CH$_2$ in THF and a base, as previously discussed, forming the protected allyl compounds (XXVI) and the bisallyl compounds (XXVI'). The protected allyl compounds (XXVI) and the bisallyl compounds (XXVI') can be separated at this point but it is preferable to use the mixture as the starting material for the next step. The protected allyl compounds (XXVI) and the bisallyl compounds (XXVI') are cyclized to form the oxazolidinone nucleus by reaction with an electrophilic agent, as previously discussed. The oxazolidinone nuclei formed are the protected iodomethyloxazolidin-2-ones (XXVII) and the allyliodomethyloxazolidin-2-ones (XXVII'). Following formation of the oxazolidinone ring, the desired side chain at the 5-position is formed, as previously discussed, to form the azides (XXVIII) and allylazides (XXVIII'). During the reaction of the iodomethyl compounds (XXVII/XXVII') to the corresponding azides (XXVIII/XXVIII') the protecting group, $X_1$, of the iodomethyl compounds (VI) may be lost, see CHART E. In other cases it will be retained and can be removed after the aminomethyl group is acylated. The azides (XXVIII) and allylazides (XXVIII') can be separated but it is preferred to not separate them at this stage but to reduce the mixture. The azides (XXVIII) and allylazides (XXVIII') are reduced with hydrogen, as previously discussed, to give aminomethyloxazolidin- 2-ones (XXIX) and 3-allyl-5-aminomethyloxazolidin-2-ones (XXIX').

When the oxazolidinone nucleus is formed to give compounds (XXVII and XXVII') an asymmetric center is created at $C_5$ which gives rise to a racemic mixture. It is preferable to resolve the racemic mixture, if desired, at the aminomethyloxazolidin-2-one (XXIX) and allylaminomethyloxazolidin-2-one (XXIX') stage using methods known to those skilled in the art, as previously discussed.

The aminomethyloxazolidin-2-ones (XXIX) and allylaminomethyloxazolidin-2-ones (XXIX') are then acylated to produce the protected indazolyloxazolidin-2-ones (XXX), unprotected indazolyloxazolidin-2-ones (XXXI) and allyl indazolyloxazolidin-2-ones (XXX') containing the desired $R_1$ group at $C_5$. In the case of the indazolyloxazolidin-2-ones (XXX) the acylation produces the bis acylated compound with the acyl group also at the 1-indazolyl position. In most cases this will be a desired product and therefore is in the scope of the claimed indazolyloxazolidin-2-ones (XXXII). The allyl indazolyloxazolidin-2-ones (XXXII') are useful pharmacological agents and intermediates within the scope of the indazolyloxazolidin-2-ones (XXXII). It is preferred that $R_1$ is H, $C_1$-$C_6$ alkyl, $C_3$-$C_6$ cycloalkyl, —OCH$_3$ and —CHCl$_2$; it is more preferred that $R_1$ is —CH$_3$.

In the cases where the protecting group, $X_1$, was not cleaved by azide the protecting group is then removed, for example, by trifluoroacetic acid treatment to give the unprotected indazolyloxazolidin-2-ones (XXXI).

The unprotected indazolyloxazolidin-2-ones (XXXI) are then N-acylated or N-alkylated, if necessary, with the desired $R_5$ group, either as the acid halide, anhydride, or alkyl halide to produce the desired indazolyloxazolidin-2-ones (XXXII). For the indazolyloxazolidin-2-ones (XXXII), it is preferred that $R_5$ is selected from the group consisting of —CH$_3$, —CH$_2$—CH=CH$_2$, —CH$_2$—C≡CH, —CHO, —CO—$R_{5-1}$ where $R_{5-1}$ is —CH$_3$, —C$_2$H$_5$, —CH(CH$_3$)$_2$, —CHCl$_2$, —CH$_2$—OH, —CH$_2$—O—CH$_3$, 2-thiophene and cyclopentyl. It is more preferred that $R_5$ is —CH$_3$, —CH$_2$—CH=CH$_2$, —CHO, —CO—$R_{5-1}$ where $R_{5-1}$ is —CH$_3$, —C$_2$H$_5$, —CHCl$_2$, —CH$_2$—CN, —CH$_2$—OH, —CH$_2$—O—CH$_3$, —CH$_2$—O—CO—CH$_3$, —CH$_2$—O—CH$_2$—φ or 2-thiophene.

The benzimidazolyloxazolidin-2-ones (XLIII) and the benzotriazolyloxazolidin-2-ones (LIV) are prepared in a similar manner (compare CHARTS F and G) to the indazolyloxazolidin-2-ones (XXXII) (CHART E) with the following exceptions. First, with the indazolyl compounds when transforming the urethane (XXV) to the protected allyl compound (XXVI), the allyl group replaced the protecting group ($X_1$) to some extent producing the bisallylindazolyl compounds (XXVI'); with the benzimidazolyloxazolidin-2-ones (XLIII) and the benzotriazolyloxazolidin-2-ones (LIV) the $X_1$ protecting group is not lost when transforming the urethanes (XXXVI and XLVII) to the protected compounds (XXXVII and XLVIII) respectively. Second, with the indazolyl compounds when reducing the azide (XXVIII) with hydrogen again the protecting group is lost producing the aminomethyl compounds (XXIX); with the benzimidazolyloxazolidin-2-ones (XLIII) and the benzotriazolyloxazolidin-2-ones (LIV) the protecting group $X_1$ is not lost when reducing the protected azides (XXXIX and L) respectively.

In producing the benzimidazolyloxazolidin-2-ones (XLIII), in many cases the desired $R_5$ group of the benzimidazolyloxazolidin-2-ones (XLIII) may be the same as the protecting group $X_1$ in the intermediate precursors (XXXIV-XLI). In those cases the protected benzimidazolyloxazolidin-2-ones (XLI) are identical to the benzimidazolyloxazolidin-2-ones (XLIII), and therefore one has obtained the useful end product when obtaining the protected benzimidazolyloxazolidinones (XLI).

For the benzimidazolyloxazolidin-2-ones (XLIII) it is preferred that $R_6$ is —H or $C_1$-$C_6$ alkyl.

The 5'-indolinyloxazolidin-2-ones (XI), the 3-(fused-ring substituted)phenyl-5β-amidomethyloxazolidine-2-ones (XXI), the indazolyloxazolidin-2-ones (XXXII), the benzimidazolyloxazolidin-2-ones (XLIII) and the benzotriazolyloxazolidin-2-ones (XLIV) all have an asymmetric center at the $C_5$-position of the oxazolidinone ring which produces two enantiomers. The mixture of enantiomers is resolved by means known to those skilled in the art. The enantiomer which is pharmacologically active is the β-enantiomer, see CHARTS A thru G. The racemic mixture is useful in the same way and for the same purpose as the pure β-enantiomer; the difference is that twice as much racemic material must be used to produce the same effect as the pure β-enantiomer.

For convience the indazolyloxazolidin-2-ones (XXXII), benzimidazolyloxazolidin-2-ones (XLIII) and benzotriazolyloxazolidin-2-ones (LIV) will be collectively referred to as the 3-(nitrogen substituted)phenyl-5β-amidomethyloxazolidin-2-ones (LV).

The 5'-idolinyloxazolidin-2-ones (XI), 3-(fused-ring substituted)phenyl-5β-(amidomethyl)oxazolidin-2-ones (XXI) and the 3-(nitrogen substituted)phenyl-5β-(amidomethyl)oxazolidin-2-ones (LV) of the present invention are useful as antibacterial agents in treating infections in mammals caused by gram-positive and anaerobic infections. It is preferred to treat humans and useful warm-blooded mammals such as cattle, horses, sheep, hogs, dogs, cats, etc.

The 5'-indolinyloxazolidin-2-ones (XI), 3-(fused-ring substituted)phenyl-5β-(amidomethyl)oxazolidin-2-ones (XXI) and the 3-(nitrogen substituted)phenyl-5β-(amidomethyl)oxazolidin-2-ones (LV) of the present invention are also useful in treating AIDS patients infected with *Mycobacterium avium*.

The 5'-indolinyloxazolidin-2-ones (XI), 3-(fused-ring substituted)phenyl-5β-(amidomethyl)oxazolidin-2-ones (XXI) and the 3-(nitrogen substituted)phenyl-5β-(amidomethyl)oxazolidin-2-ones (LV) can be administered either parenterally (IV, IM, SQ) or orally. The daily dose is about 5 to about 20 mg/kg. This dose can preferably be given in divided doses and administered 2-4 times daily. The preferred route of administration as well as the particular dosage form for either the parenteral or oral route depends on the particular facts of the situation including the nature of the infection and condition of the patient. The usual pharmaceutical dosage forms appropriate for parenteral (solution, suspension in oil) and oral (tablet, capsule, syrup, suspension, etc.) administration are known to those skilled in the art and there is nothing unusual about using those dosage forms with the 5'-indolinyloxazolidin-2-ones (XI), the 3-(fused-ring substituted)phenyl-5β-(amidomethyl)oxazolidin-2-ones (XXI) and the 3-(nitrogen substituted)phenyl-5β-(amidomethyl)oxazolidin-2-ones (LV). The exact dosage of the 5'-indolinyloxazolidin-2-ones (XI), the 3-(fused-ring substituted)phenyl-5β-(amidomethyl)oxazolidin-2-ones (XXI) and the 3-(nitrogen substituted)phenyl-5β-(amidomethyl)oxazolidin-2-ones (LV) to be administered, the frequency of administration, route of administration, the dosage form will vary depending on a number of factors known to those skilled in the art including the age, weight, sex, general physical condition of the patient, the nature of the infection (particular microorganism involved, its virulence, the extent of the infection) other medical problems of the patient, etc. as is well known to the physician treating infectious diseases.

The 5'-indolinyloxazolidin-2-ones (XI), the 3-(fused-ring substituted)phenyl-5β-(amidomethyl)oxazolidin-2-ones (XXI) and the 3-(nitrogen substituted)phenyl-5β-(amidomethyl)oxazolidin-2-ones (LV) can be used either alone or in conjunction with other antibacterial agents as is known to those skilled in the art. Further, the 5'-indolinyloxazolidin-2-ones (XI), the 3-(fused-ring substituted)phenyl-5β-(amidomethyl)oxazolidin-2-ones (XXI) and the 3-(nitrogen substituted)phenyl-5β-(amidomethyl)oxazolidin-2-ones (LV) can be used in conjunction with non-antibacterial agents as is known to those skilled in the art.

Suitable pharmaceutically acceptable salts include, for example, chloride, sulfate, phosphate, citrate and oxylate.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3—C(=Z_1)H$. Groups $R_i$ and $R_j$ would represent monovalent variable substituents if attached to the formula $CH_3—CH_2—C(R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom.

Chemical formulas or portions thereof drawn in a linear fashion represent atoms in a linear chain. The symbol "—" in general represents a bond between two atoms in the chain. Thus $CH_3$—O—$CH_2$—CH-($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways; —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—($CH_2$)$_2$—N($C_2H_5$)—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol "- - -" or ". . .". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents $\alpha$—$R_{i-j}$ and $\beta$—$R_{i-k}$. When a bivalent variable, $R_i$, is defined to consist of two monovalent variable substituents, the convention used to define the bivalent variable is of the formula "$\alpha$—$R_{i-j}$:$\beta$—$R_{i-k}$" or some variant thereof. In such a case both $\alpha$—$R_{i-j}$ and $\beta$—$R_{i-k}$ are attached to the carbon atom to give —C($\alpha$—$R_{i-j}$)($\beta$—$R_{i-k}$)—. For example, when the bivalent variable $R_6$, —C(=$R_6$)— is defined to consist of two monovalent variable substituents, two monovalent variable substituents are $\alpha$—$R_{6-1}$:$\beta$—$R_{6-2}$, . . . $\alpha$—$R_{6-9}$:$\beta$—$R_{6-10}$, etc., giving —C($\beta$—$R_{6-1}$)($\beta$—$R_{6-2}$)—, . . . —C($\alpha$—$R_{6-9}$)($\beta$—$R_{6-10}$)—, etc. Likewise, for the bivalent variable $R_{11}$, —C(=$R_{11}$)—, two monovalent variable substituents are $\alpha$—$R_{11-1}$:$\beta$—$R_{11-2}$. For a ring substituent for which separate $\alpha$ and $\beta$ orientations do not exist (e.g. due to the presence of a carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1$($R_i$)H—$C_2$($R_j$)H— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —$CH_2$—$CH_2$—O—CO— . . . " means a lactone in which the carbonyl is bonded to $C_2$. However, when designated ". . . $R_j$ and $R_i$ are taken together to form —$CH_2$—$CH_2$—O—CO— . . . the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$-($CH_2$)$_n$—O—CO— where n is zero, one or 2. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. DEFINITIONS

All temperatures are in degrees Centigrade.

TLC refers to thin-layer chromatography.

THF refers to tetrahydrofuran.

THP refers to tetrohydropyanyl.

DMF refers to dimethylformamide.

TEA refers to triethylamine.

Alcohol refers to ethyl alcohol.

MPLC refers to medium pressure liquid chromatography.

Saline refers to an aqueous saturated sodium chloride solution.

IR refers to infrared spectroscopy.

CMR refers to C-13 magnetic resonance spectroscopy, chemical shifts are reported in ppm ($\delta$) downfield from TMS.

NMR refers to nuclear (proton) magnetic resonance spectroscopy, chemical shifts are reported in ppm ($\delta$) downfield from tetramethylsilane.

TMS refers to trimethylsilyl.

$\phi$ refers to phenyl ($C_6H_5$).

MS refers to mass spectrometry expressed as m/e or mass/charge unit. [M+H]+ refers to the positive ion of a parent plus a hydrogen atom. EI refers to electron impact. CI refers to chemical ionization. FAB refers to fast atom bombardment.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

~ indicates that there are 2 possible orientations for the attached group, (1) α or β when attached to the ring and (2) cis or trans when attached to a carbon atom of a double bond.

BOC refers to t-butyloxycarbonyl, —CO—O—C(CH$_3$)$_3$.

CBZ refers to carbobenzyloxy, —CO—O—CH$_2$—φ.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

N-Acetyl-5-nitroindoline (II)

A mixture of 5-nitroindoline (I, 12.012 g) in pyridine (100 ml) and acetic anhydride (50 ml) is stirred for 17 hr under argon. The mixture is then concentrated under reduced pressure to give the title compound, mp 175°–177°; NMR (CDCl$_3$, 300 MHz) 8.28, 8.10, 8.01, 4.23, 3.31 and 2.28 δ; CMR (CDCl$_3$, 75.47 MHz) 23.95, 27.01, 49.11, 115.73, 119.93, 124.27, 132.4, 143.4 and 169.8 δ; IR (CHCl$_3$) 1680, 1600, 1480, 1470, 1390, 1340 and 1320 cm$^{-1}$.

EXAMPLE 2

N-Acetyl-5-aminoindoline (III)

Palladium on carbon (10%, 1.110 g) is added to a mixture of N-acetyl-5-nitro indoline (II, EXAMPLE 1, 5.00 g) in ethyl acetate (freshly opened bottle, about 500 ml). The mixture is stirred under 1 atm of hydrogen (balloon) for 39 hr then filtered and the palladium on carbon is washed with methanol/ethyl acetate (20/80). The filtrate is concentrated under reduced pressure to give the title compound, mp 183°–185°; NMR (CDCl$_3$, 300 MHz) 8.01, 6.53, 6.50, 3.98, 3.56, 3.04 and 2.17 δ; CMR (CDCl$_3$, 75.47 MHz) 23.86, 28.05, 48.71, 111.55, 113.73, 117.66, 132.8, 135.6, 149.1 and 168.1 δ; IR (CHCl$_3$) 3000, 1640, 1600, 1490, 1410, 1330 and 1300 cm$^{-1}$.

EXAMPLE 3

1-Acetyl-(N-carbobenzyloxy)-5-aminoindoline (IV)

Benzyl chloroformate (1.2 ml) is added to a solution of N-acetyl-5-aminoindoline (III, EXAMPLE 2, 1.4 g) and sodium bicarbonate (1.33 g) in acetone/water (40/60, 20 ml) at 0°. The mixture is stirred for 2.5 hr, then benzyl chloroformate (0.5 ml) is added. After stirring for 2.3 hr, the mixture is poured into chloroform (25 ml) and the organic layers are washed with aqueous sodium bisulfate (10%, 2×) and then washed with aqueous sodium carbonate (10%, 2×). Chloroform (about 200 ml) is added to the aqueous layers and then the organic layers are washed again with aqueous sodium bisulfate (10%), aqueous sodium carbonate (10%), then dried over magnesium sulfate, and concentrated under reduced pressure to give the title compound, 180°–182°; NMR (CDCl$_3$, 300 MHz) 8.03, 7.38, 7.30–7.23, 6.98, 6.90, 5.09, 3.90, 3.05 and 2.09 δ; CMR (CDCl$_3$, 75.47 MHz) 23.98, 28.07, 48.90, 66.89, 115.9, 117.05, 118.1, 128.25, 128.59, 132.22, 133.78, 136.21, 139.4, 154.2 and 168.39 δ; IR (CHCl$_3$) 3440, 1730, 1660, 1600, 1490 and 1400 cm$^{-1}$.

EXAMPLE 4

1-Acetyl-(N-allyl-N-carbobenzyloxy)-5-aminoindoline (V)

Sodium hydride/mineral oil (50% w/w, 425 mg) is added to a mixture of 1-acetyl-(N-carbobenzyloxy)-5-aminoindoline (IV, EXAMPLE 3, 2.00 g) in THF (freshly distilled 80 ml). Allyl bromide (0.725 ml) is added and the mixture is refluxed for 26.5 hr under nitrogen. At the end of this time it is poured into water and extracted with ethyl acetate (3×). The organic layers are combined and dried over magnesium sulfate and concentrated under reduced pressure to a solid which is purified on a 40–63μ silica column eluting with a gradient from 100% hexane to 100% ethyl acetate. The appropriate fractions are pooled and concentrated to give the title compound, mp 108°–110°; NMR (CDCl$_3$, 300 MHz) 8.17, 7.29, 7.03, 5.9, 5.14, 5.1, 4.24, 4.00, 3.13 and 2.17 δ; CMR (CDCl$_3$, 75.47 MHz) 23.80, 27.54, 48.69, 53.23, 66.98, 116.57, 117.01, 123.13, 126.2, 127.38, 127.60, 128.13, 131.61, 133.37, 136.35, 137.3, 141.6, 155.12 and 168.33; IR (CHCl$_3$) 1700, 1650, 1490 and 1400 cm$^{-1}$; MS (m/e) 350, 215, 173 and 91; exact mass calc'd for $C_{21}H_{22}N_2O_3 = 350.1630$, found 350.1607.

EXAMPLE 5

(γ)-3-(5'-1-Acetylindolyinyl)-5-(iodomethyl)oxazolidin-2-one (VI)

Iodine (1.94 g) is added to a mixture of 1-acetyl-(N-allyl-N-carbobenzyloxy)-5-aminoindoline (V, EXAMPLE, 4, 1.3 g) in chloroform (20 ml). After stirring for 3 hr under nitrogen the mixture is poured into additional chloroform and washed with aqueous sodium thiosulfate (10%, 2×), dried over sodium sulfate and concentrated under reduced pressure to give the title compound, mp 188°–190°; NMR (CDCl$_3$, 300 MHz) 8.17, 7.66, 7.01, 4.7, 4.15, 4.06, 3.76, 3.46, 3.36 and 2.22 δ; CMR (CDCl$_3$, 75.47 MHz) 6.13, 23.98, 28.00, 48.82, 51.30, 71.09, 115.621, 116.73, 117.00, 132.38, 133.7, 139.9, 154.4 and 168.44 δ; IR (CHCl$_3$) 1760, 1660, 1490 and 1400 cm$^{-1}$; MS (m/e) 386, 344, 299, 258, 216, 189, 173, 158, 145, 132; exact mass calcd for $C_{14}H_{15}IN_2O_3 = 386.0129$, found 386.0130.

EXAMPLE 6

(+)-3-(5'-1-Acetylindolyinyl)-5-(azidomethyl)oxazolidin-2-one (VII)

Sodium azide (1.005 g) in water (10 ml) is added to a mixture of (±)-3-(5'-acetylindolinyl)-5-(iodomethyl)oxazolidin-2-one (VI, EXAMPLE 5, 0.798 g) in acetone (150 ml). The mixture is refluxed under nitrogen for 42.5 hr then poured into water (225 ml). The aqueous layer is extracted with ethyl acetate (3×, 400 ml). The combined organic layers are washed with water 500 ml), with saline (300 ml) then dried over magnesium sulfate and concentrated under reduced pressure to give the title compound, mp 165°–166°; NMR (CDCl$_3$, 300 MHz) 8.08, 7.57, 6.9, 4.7, 4.0, 3.75, 3.62, 3.5, 3.11 and 2.14 δ; CMR (CDCl$_3$, 75.47 MHz) 23.92, 27.94, 47.69, 48.78, 52.97, 70.52, 115.48, 116.62, 116.82, 132.37, 133.48, 139.45, 153.97, and 168.43 δ; IR (CHCl$_3$) 2105, 1750, 1650, 1480 and 1390 cm$^{-1}$; MS (m/e) 301, 273, 229, 160, 146, 132 and 117; exact mass calcd for $C_{14}H_{15}N_5O_3$ = 301.1174, found 301.1194.

EXAMPLE 7

(±)-3-(5'-1-Acetylindolinyl)-5-(aminomethyl)oxazolidin-2-one (VIII)

Palladium on carbon (10%, 110 mg) is added to a mixture of (+)-3-(5'-1-acetylindolinyl)-5-(azidomethyl)oxazolidin-2-one (VII, EXAMPLE 6, 550 mg) in methanol/ethyl acetate (8/92, 130 ml). The mixture is stirred for 24 hr under 1 atm (balloon) of hydrogen. The solution is filtered and the filtrate is concentrated under reduced pressure to give the title compound, 164°–165°; NMR (CDCl$_3$, 300 MHz) 8.08, 7.61, 6.9, 4.58, 3.98, 3.75, 3.11, 3.02, 2.90, 2.14 and 1.33; CMR (CDCl$_3$, 75.47 MHz) 23.96, 28.00, 44,96, 47.93, 48.82, 73.79, 115.40, 115.67, 132.29, 133.97, 139.6, 155.2 and 168.40 δ; IR (CHCl$_3$) 1750, 1650, 1490, 1400 and 900 cm$^{-1}$; MS (m/e) 275, 233, 189, 160, 147 and 117.

EXAMPLE 8

(±)-3-(5'-1-Acetylindolinyl)-5-(acetamidomethyl)oxazolidin-2-one (IX)

A mixture of (±)-3-(5'-1-acetylindolinyl)-5-(aminomethyl)oxazolidin-2-one (VIII, EXAMPLE 7, 200 mg) in pyridine (5 ml) and acetic anhydride (2.5 ml) is stirred overnight. The mixture then is concentrated under reduced pressure to give a solid. The solid is recrystallized by dissolving in as little chloroform and methanol as possible then added to an equal volume of ethyl acetate and concentrated by evaporation under a nitrogen stream to give the title compound, mp 234°–235°; NMR (CDCl$_3$, 300 MHz) 8.16, 7.58, 7.03, 6.37, 4.76, 4.04, 3.76, 3.65, 3.20, 2.23 and 2.03 δ; CMR (CDCl$_3$, 75.47 MHz) 23.00, 23.95, 27.99, 30.81, 41.90, 47.88, 48.81, 71.70, 115.44, 116.82, 117.13, 132.27, 133.55, 139.53, 154.45, 168.46 and 170.92 δ; IR (CHCl$_3$) 1755, 1670, 1490 and 1400 cm$^{-1}$; MS (m/e) 317, 273, 189, 172, 159, 147 and 117.

EXAMPLE 9

1-Carbo-t-butyloxy-5-nitroindoline (II)

Di-tert-butylcarbonate (13.4 g) is added all at once to a solution of 5-nitroindoline (I, 5.00 g) in freshly distilled THF (85 ml). The mixture is refluxed for three days then di-tert-butyldicarbonate carbonate (9.90 g) is added and the mixture refluxed overnight. The mixture is poured into water (2.25 ml), this is extracted with ethyl acetate (4x, total 450 ml). The combined organic layers are washed with aqueous sodium bicarbonate (5%, 500 ml), saline, dried over magnesium sulfate and concentrated under reduced pressure. The mixture of solid and oil is triturated in hexane and filtered to give the title compound, NMR (CDCl$_3$, 300 MHz) 8.10, 7.99, 7.85, 4.09, 3.17 and 1.58 δ; CMR (CDCl$_3$, 75.47 MHz) 26.38, 28.11, 48.32, 81.8, 113.58, 120.28, 124.53, 142.38 and 151.82; IR (CHCl$_3$) 1710, 1605, 1490, 1395 and 1320 cm$^{-1}$; MS (m/e) 264, 208, 164 and 57; exact mass calcd for $C_{13}H_{16}N_2O_4$ = 264.1110, found 264.1117.

EXAMPLE 10

1-Carbo-t-butyloxy-5-aminoindoline (III)

Palladium on carbon (10%, 1.0 g) is added to a mixture of 1-carbo-t-butyloxy-5-nitroindoline (II, EXAMPLE 9, 4.554 g) in ethyl acetate (freshly opened bottle, 500 ml) at 0°. The mixture is stirred under 1 atm of hydrogen (balloon) at 20°–25° for 3.5 hr. The mixture is then filtered and concentrated under reduced pressure. The concentrated filtrate is taken up in ethyl acetate and washed with saline (3×). The combined aqueous layers are extracted with ethyl acetate (3×). All organic phases are combined and washed with saline, dried over magnesium sulfate and concentrated under reduced pressure to give the title compound, NMR (CDCl$_3$, 300 MHz) 7.64 7.26, 6.50, 3.93, 3.48, 3.00 and 1.54 δ; CMR (CDCl$_3$, 75.47 MHz) 27.47, 28.42, 47.41, 77.39, 79.6, 80.6, 112.14, 113.67, 115.15, 132.4, 113.0, 134.5, 135.2, 141.71 and 152.36; IR (CHCl$_3$) 3360, 3440, 1680, 1485 and 1390 cm$^{-1}$; MS (m/e) 234, 178, 134 and 57.

EXAMPLE 11

1-Carbo-t-butyloxy-(N-carbobenzyloxy)-5-aminoindoline (IV)

Benzyl chloroformate (2.1 ml) is added to a mixture of 1-carbo-t-butyloxy-5-aminoindoline (III, EXAMPLE 10, 3.147 g) and sodium bicarbonate (2.40 g) in acetone/water (55/45, 40 ml) at 0°. After stirring for one hour, chloroform (50 ml) is added to the mixture. The mixture is then poured into ethyl acetate (50 ml) and washed with saline. The aqueous layer is then extracted with ethyl acetate (2× for total of 200 ml). The organic layers are combined and washed with aqueous sodium bisulfate (10%, 2×100 ml), aqueous sodium carbonate (10%, 2×100 ml), saline (100 ml), dried over magnesium sulfate then concentrated under reduced pressure to give the title compound, NMR (CDCl$_3$, 300 MHz) 7.74, 7.33, 7.00, 5.14, 3.92, 2.98, and 1.54 δ; CMR (CDCl$_3$, 300 MHz) 27.0, 28.303, 46.1, 47.52, 66.66, 73.3, 80.1, 81.0, 114.51, 118.00, 128.05, 128.38, 132.2, 132.36, 136.09, 138.3, 138.9, 152.37 and 153.60 δ; IR (CHCl$_3$) 3430, 1730, 1685, 1485, 1385 cm$^{-1}$.

EXAMPLE 12

1-Carbo-t-butyloxy-(N-allyl-N-carbobenzyloxy)-5-amioindoline (V)

Sodium hydride/mineral oil (50% w/w, 800 mg) is added to a mixture of 1-carbo-t-butyloxy-(N-carbobenzyloxy)-5-aminolidoline (IV, EXAMPLE 11, 4.480 g) in freshly distilled THF (180 ml). Allyl bromide (1.32 ml) is added and the mixture is refluxed for 5.5 hr under nitrogen, then it is poured into water and extracted with ethyl acetate (3×). The combined organic layers are washed with saline and dried over magnesium sulfate and then concentrated under reduced pressure to an oil which is passed over a silica column (40-63μ) eluting with a hexane-ethyl acetate gradient (100% to 100%). The appropriate fractions are pooled to give the title compound, NMR (CDCl$_3$, 300 MHz) 7.80, 7.29, 6.98, 5.87, 5.14, 4.23, 3.96, 3.04 and 1.55 δ; CMR (CDCl$_3$, 75.47 MHz) 27.11, 28.41, 47.80, 53.54, 67.16, 77.35, 80.5, 114.55, 117.23, 126.5, 127.60, 127.80, 128.35, 132.0, 133.69, 136.4, 136.72, 141.6, 152.43 and 155.47 δ; IR (CHCl$_3$) 1690, 1490, 1395 and 1160 cm$^{-1}$.

EXAMPLE 13

(±)-3-(5'-1-Carbo-t-butyloxyindolinyl)-5-(iodomethyl)oxazolidin-2-one (VI)

Iodine (5.512 g) is added to a mixture of 1-carbo-t-butyloxy-(N-allyl-N-carbobenzyloxy)-5-aminoindoline (V, EXAMPLE 12, 4.190 g) in chloroform (65 ml). After stirring for 3 hr the mixture is poured into chloroform (40 ml), washed with aqueous sodium thiosulfate (10%, 3×100 ml), dried over magnesium sulfate and concentrated under reduced pressure to a residue. The residue is passed over a silica column (40-63μ) eluting with ethyl acetate/hexane (10/90) then eluted with chloroform. The appropriate fractions are pooled and concentrated to a solid which is recrystallized from acetone/water to give the title compound, mp 174°-175°; NMR (CDCl$_3$, 300 MHz) 7.80, 7.53, 7.07, 4.69, 4.13, 3.98, 3.45, 3.35, 3.09 and 1.56 δ; CMR (CDCl$_3$, 75.47 MHz) 6.18, 27.0, 28.26, 47.54, 51.34, 70.94, 80.6, 114.35, 115.96, 117.36, 132.17, 139.8, 152.24 and 154.01 δ; IR (CHCl$_3$) 1760, 1690, 1490, 1370, 1145, cm$^{-1}$.

EXAMPLE 14

(±)-3-(5'-1-Carbo-t-butyloxyindolinyl)-5-(azidomethyl)oxazolidin-2-one (VII)

Following the general procedure of EXAMPLE 6 and making non-critical variations but starting with (±)-3-(5'-1-carbo-t-butyloxyindolinyl)-5-(iodomethyl)oxazolidin-2-one (VI, EXAMPLE 13), the title compound is obtained, mp 168°-170°.

EXAMPLE 15

(±)-3-(5'-1-Carbo-t-butyloxyindolinyl)-5-(aminomethyl)oxazolidin-2-one (VIII)

Following the general procedure of EXAMPLE 7 and making non-critical variations but starting with (±)-3-(5'-1-carbo-t-butyloxyindolinyl)-5-(azidomethyl)oxazolidin-2-one (VII, EXAMPLE 14), the title compound is obtained, mp 166-168.

EXAMPLE 16

(±)-3-(5'-1-Carbo-t-butyloxyindolinyl)-5-(acetamidomethyl)oxazolidin-2-one (IX)

Following the general procedure of EXAMPLE 8 and making non-critical variations but starting with (±)-3-(5'-1-carbo-t-butyloxyindolinyl)-5-(aminomethyl)oxazolidin-2-one (VIII, EXAMPLE 17), the title compound is obtained, mp 139°-140°.

EXAMPLE 17

(±)-3-(5'-Indolinyl)-5-(acetamidomethyl)oxazolidin-2-one (X)

Trifluoroacetic acid (0.250 ml) is added slowly over one minute to a mixture of (±)-3-(5'-1-carbo-t-butyloxyindolinyl)-5-(acetamidomethyl)oxazolidin-2-one (IX, EXAMPLE 16, 0.038 mg) in methylene chloride (3 ml). The mixture is stirred for 1.5 hr under nitrogen then poured into saturated aqueous sodium bicarbonate (30 ml). The aqueous mixture is extracted with methylene chloride (3× for a total of 40 ml). The combined organic extracts are washed with saturated aqueous sodium bicarbonate (10 ml) and the aqueous extracts combined. The combined aqueous extracts are extracted again with methylene chloride (5× for a total of 50 ml). The combined organic extracts are dried over magnesium sulfate and concentrated under reduced pressure to give the title compound, MS (m/e) 275, 231, 172, 159 and 147; exact mass calcd for C$_{14}$H$_{17}$N$_3$O$_3$=275.1270, found 275.1282.

EXAMPLE 18

(±)-3-(5'-1-Isobutyrlindolinyl)-5-(aceamidomethyl)oxazolidin-2-one (XI)

(±)-3-(5'-Indolinyl)-5-(acettamidomethyl)oxazolidin-2-one (X, EXAMPLE 17, 53 mg) is dissolved in methylene chloride (1.0 ml). Triethylamine (80 μl) is added. Isobutyl chloride (25 μl) is added slowly over 30 seconds at 0°. After stirring for two hr, the mixture is added to saline (10 ml) and extracted with methylene chloride (6× for 20 ml total). The combined organic extracts are dried over magnesium sulfate and concentrated to provide a solid. The solid is purified by passing thru a silica cartridge, eluting with chloroform (1 ml) ethyl acetate (4 ml), methanol/ethyl acetate (10/90, 27 ml). The appropriate fractions are pooled and concentrated to give the title compound, mp 200°-202°.

EXAMPLES 19-24

Following the general procedure of EXAMPLE 18 and making non-critical variations but using the appropriate R$_5$ group the compounds of EXAMPLES 19-24 are obtained:

| EXAMPLE | Compound Obtained |
| --- | --- |
| 19 | (±)-3-(5'-1-Propanoylindolinyl)-5-(acetamidomethyl)oxazolidin-2-one (XI), |
| 20 | (±)-3-(5'-1-Cyclopentylcarbonylindolinyl)-5-acetamidomethyl)oxazolidin-2-one (XI), |
| 21 | (±)-3-(5'-1-Formylindolinyl)-5-(acetamidomethyl)-oxazolidin-2-one (XI), |
| 22 | (±)-3-(5'-1-Chloroacetylindolinyl)-5-(acetamidomethyl)oxazolidin-2-one (XI), |
| 23 | (±)-3-(5'-1-Dichloroacetylindolinyl)-5-(acetamidomethyl)oxazolidin-2-one (XI) and |
| 24 | (±)-3-(5'-1-Phenylacetylindolinyl)-5-(acetamidomethyl)oxazolidin-2-one (XI) |

EXAMPLE 25

1-Carbo-t-butyloxy-6-nitroindoline (II)

Di-tert-butyldicarbonate (11.500 g) is added to a mixture of 6-nitroindoline (I, 4.300) in freshly distilled THF (40 ml). The mixture is refluxed for 3 days then poured into water (125 ml) and extracted with ethyl acetate (3×, 220 ml total). The combined organic layers are washed with aqueous sodium bicarbonate (5%), saline, dried over magnesium sulfate and concentrated under reduced pressure to obtain a mixture of a solid in an oil. This mixture is recrystallized with acetone/water to give the title compound, mp 104°-105°; NMR (CDCl$_3$, 300 MHz) 8.5-8.1, 7.71, 7.14, 4.00, 3.10 and 1.51 δ; CMR (CDCl$_3$, 75.47 MHz) 27.12, 28.16, 47.94, 77.2, 81.3, 109.28, 117.51, 124.45, 138.4, 143.6, 147.84 and 151.92 δ;

IR (CHCl$_3$) 1695, 1480, 1385, 1340 and 1140 cm$^{-1}$; MS (m/e) 264, 208, 191, 164, 118 and 57.

EXAMPLE 26

1-Carbo-t-butyloxy-6-aminoindoline (III)

Palladium on carbon (10%, 1.198 g) is added to a mixture of 1-carbo-t-butyloxy-6-nitroindoline (II, EXAMPLE 25, 5.311 g) in ethyl acetate (freshly open bottle, 500 ml) at 0°. The mixture is stirred under 1 atm hydrogen (balloon) at 20°–25° for 7 hr. The mixture is then filtered and concentrated under reduced pressure to give the title compound, mp 151°–152°; NMR (CDCl$_3$, 300 MHz) 7.29, 6.80, 6.25, 3.93, 3.61 and 2.95 δ; CMR (CDCl$_3$, 75.47 MHz) 26.58, 28.47, 48.29, 3380, 3460, 1690, 1620, 1490, 1450 and 1390 cm$^{-1}$.

EXAMPLE 27

1-Carbo-t-butyloxy-(N-carbobenzyloxy)-6-aminoindoline (IV)

Following the general procedure of EXAMPLES 3 and 11 and making non-critical variations but starting with 1-carbo-t-butyloxy-6-aminoindoline (III, EXAMPLE 26), the title compound is obtained, MS (m/e) 368, 312, 268, 91 and 57; exact mass calcd for C$_{21}$H$_{24}$N$_2$O$_4$=368.1736, found 368.1737.

EXAMPLE 28

1-Carbo-t-butyloxy-(N-allyl)-N-carbobenzyloxy)-6-aminoindoline (V)

EXAMPLE 29

(±)-3-(6'-1-Carbo-t-butyloxyindolinyl)-5-(iodomethyl)oxazolidin-2-one (VI)

Following the general procedure of EXAMPLES 5 and 13 and making non-critical variations but starting with 1-carbo-t-butyloxy-(N-allyl-N-carbobenzyloxy)-6-aminoindoline (V, EXAMPLE 28), the title compound is obtained, MS (m/e) 444, 388, 217, 173, 57 and 41; exact mass calcd for C$_{17}$H$_{21}$N$_2$O$_4$=444.0548, found 444.0560.

Following the general procedure of EXAMPLES 4 and 12 and making non-critical variations but starting with 1-carbo-t-butyloxy-(N-carbobenzyloxy)-6-aminoindoline (IV, EXAMPLE 27), the title compound is obtained, MS (m/e) 408, 352, 308, 217, 91 and 57; exact mass calcd for C$_{24}$H$_{28}$N$_2$O$_4$=408.2049, found 408.2073.

EXAMPLE 30

(±)-3-(6'-1-Carbo-t-butyloxyindolinyl)-5-(azidomethyl)oxazolidin-2-one (VII)

Following the general procedure of EXAMPLES 6 and 14 and making non-critical variations but starting with (±)-3-(6'-1-carbo-t-butyloxyindolinyl)-5-(iodomethyl)oxazolidin-2-one (VI, EXAMPLE 29), the title compound is obtained, MS (m/e) 359, 303, 259, 186, 160 and 57; exact mass calcd for C$_{17}$H$_{21}$O$_4$=359.1593, found 359.1605.

EXAMPLE 31

(±)-3-(6'-1-Carbo-t-butyloxyindolinyl)-5-(aminomethyl)oxazolidin-2-one (VIII)

Following the general procedures of EXAMPLES 7 and 15 and making non-critical variations but starting with (±)-3-(6'-1-carbo-t-butyloxyindolinyl)-5-(azidomethyl)oxazolidin-2-one (VII, EXAMPLE 30), the title compound is obtained, MS (m/e) 333, 277, 233, 147 and 57; exact mass calcd for C$_{17}$H$_{23}$N$_3$O$_4$=333.1688, found 333.1692.

EXAMPLE 32

(±)-3-(6'-1-Carbo-t-butyloxyindolinyl)-5-(acetamidomethyl)oxazolidin-2-one (IX)

Following the general procedure of EXAMPLES 8 and 16 and making non-critical variations but starting with (±)-3-(6'-1-carbo-t-butyloxyindolinyl)-5-(aminomethyl)-oxazolidin-2-one (VIII, EXAMPLE 31), the title compound is obtained, MS (m/e) 375, 275, 148, 134 and 57; exact mass calcd for C$_{19}$H$_{25}$N$_3$O$_5$=375.1794, found 375.1803.

EXAMPLE 33

(±)-3-(6'-Indolinyl)-5-(acetamidomethyl)oxazolidin-2-one (X)

Following the general procedure of EXAMPLE 17 and making non-critical variations but starting with (±)-3-(6'-1-carbo-t-butyloxy-indolinyl)-5-(acetamidomethyl)-oxazolidin-2-one (IX, EXAMPLE 32), the title compound is obtained, mp 60°–62°.

EXAMPLES 34–38

Following the general procedure of EXAMPLE 18 and making non-critical variations but starting with (±)-3-(6'-indolinyl)-5-acetamidomethyl)oxazolidin-2-one (X, EXAMPLE 33) and using an acylating agent to provide the appropriate R$_5$ group the compounds of EXAMPLES 34–38 are obtained:

| EXAMPLE | Compound Obtained |
|---|---|
| 34 | (±)-3-(6'-1-Acetylindolinyl)-5-(acetamidomethyl)-oxazolidin-2-one (XII), |
| 35 | (±)-3-(6'-1-Isobutyrlindolinyl)-5-(acetamidomethyl)oxazolidin-2-one (XII), |
| 36 | (±)-3-(6'-1-Propanoylindolinyl)-5-(acetamidomethyl)oxazolidin-2-one (XII), |
| 37 | (±)-3-(6'-1-Cyclopentanecarbonylindolinyl)-5-acetamidomethyl)oxazolidin-2-one (XII) and |
| 38 | (±)-3-(6'-1-Formylindolinyl)-5-(acetamidomethyl)-oxazolidin-2-one (XII) |

EXAMPLE 39

(±)-3-(5'-1-Allylindolinyl)-5-(N-acetamidomethyl)oxazolidin-2-one (XI)

Following the general procedure of EXAMPLE 18 and making non-critical variations but using allyl bromide the title compound is obtained.

EXAMPLE 40

(±)-3-(6'-1-Allylindolinyl)-5-(acetamidomethyl)oxazolidin-2-one (XI)

Following the general procedure of EXAMPLE 18 and making non-critical variations but starting with (±)-3-(6'-indolinyl)-5-(acetamidomethyl)oxazolidin-2-one (X, EXAMPLE 33) and using allyl bromide the title compound is obtained.

EXAMPLE 41

N-(Carbobenzyloxy)-5-aminoindan (XVIA)

Sodium bicarbonate (7.20 g) is added to a solution of 5-aminoindan (XVA, 5.71 g) in acetone (60 ml) and water (30 ml) 0°, followed by the dropwise addition of benzylchloroformate (6.8 ml, 8.07 g) over 5 min. The mixture is stirred at 0° for about 1 hr, then at 20-°25° overnight. The mixture is poured into aqueous sodium hydrogen sulfate (10%, 200 ml), and ethyl acetate (300 ml). The organic extract is washed with saturated aqueous sodium bicarbonate, dried over magnesium sulfate, and concentrated under reduced pressure is give an oil. The oil is purified by column chromatography on 60–200μ silica gel, eluting with ethyl acetate/hexane (10/90). The appropriate fractions are pooled and concentrated to give the title compound, mp 56°–59°; NMR (CDCl$_3$, 300 MHz) 7.40–7.03, 7.11 7.05, 6.65, 5.18, 2.85 and 2.05 δ; IR (mineral oil mull) 3275, 2925, 1693.5, 1544 and 1236 cm$^{-1}$; MS (m/e) 267, 223, 222 and 91.

EXAMPLE 42

N-(Carbobenzyloxy)-N-(allyl)-5-aminoindan (XVIIA)

A sodium hydride/mineral dispersion (50%, 2.00 g) is carefully added to a solution of N-(carbobenzyloxy)-5-aminoindan (XVIA, EXAMPLE 41, 8.856 g) in freshly distilled tetrahydrofuran (about 350 ml) at 20° under argon. The reaction is mildly exothermic with evolution of hydrogen gas. Allyl bromide (3.4 ml, 4.8 g) is then added over 1 min. The mixture is stirred at 20°–25° for 1 hr forming a solid. The mixture is then heated at reflux for 3.5 hr then stirred at 20°–25° overnight. An aliquot is taken, poured into water and ethyl acetate, and the organic layer evaporated. NMR analysis indicates complete reaction. The mixture is poured into ethyl acetate (300 ml), and washed with water (2×250 ml). The combined aqueous layers are extracted with ethyl acetate (100 ml). The combined organic layers are washed with saline, dried over magnesium sulfate and concetrated under reduced pressure to give an oil. The residue is purified by gravity filtration thru a silica gel column (2.5 cm×10 cm, 60–200μ), eluting with hexane. The appropriate fractions are pooled and concentrated to give the title compound as an oil. An analytical sample is obtained by MPLC using ethyl acetate/hexane (10/90). NMR (CDCl$_3$, 300 MHz) 7.30, 7.16, 7.06, 6.96, 5.91, 5.16, 5.13, 4.24, 2.88 and 2.07 δ; IR (CHCl$_3$) 2944, 1694, 1400 and 1153 cm$^{-1}$; MS (m/e) 307, 263, 248, 172, 144 and 91, exact mass calculated for $C_{20}H_{21}NO_2 = 307.1572$, found 307.1565.

EXAMPLE 43

(±)-3-(5′-Indanyl)-5-(iodomethyl)oxazolidin-2-one (XVIIIA)

Iodine (16.84 g) is added to a solution of 3-(carbobenzyloxy)-N-(allyl)-5-aminoindan (XVIIA, EXAMPLE 42, 10.39 g) in chloroform (400 ml) at 20°. The mixture is stirred at 20° for 3.3 hr, then poured into aqueous sodium thiosulfate (10%, 550 ml). The layers are separated and the chloroform layer is dried over magnesium sulfate and concentrated under reduced pressure to give a solid. The solid is retained at 0.1 Torr for 18 hr to give crystals which are recrystallized from acetone (300 ml) and water (240 ml) to give after drying under reduced pressure at 70° a solid. Analysis by NMR shows this material to contain a trace of mineral oil. From the mother liquors additional product is obtained. For analysis, a small sample is chromatographed on silica gel eluting with ethyl acetate/hexane (10/90), concentrated and then recrystallized as above to give the title compound, mp 104°–105°; NMR (CDCl$_3$, 300 MHz) 7.44, 7.21, 4.69, 4.15, 3.76, 3.45, 3.34, 2.90 and 2.08 δ; CMR (75.47 MHz, CDCl$_3$) 6.07, 25.39, 32.05, 32.86, 51.29, 70.93, 115.04, 116.56, 124.40, 135.76, 140.38 and 145.22 δ; IR (mineral oil mull) 2922, 1728, 1485 and 1420 cm$^{-1}$; MS (m/e) 343, 215, 172, 144, 117 and 91, exact mass calculated for $C_{13}H_{14}INO_2 = 343.0071$, found 343.0066.

EXAMPLE 44

(±)-3-(5′-Indanyl)-5-(azidomethyl)oxazolidin-2-one (XIXA)

Sodium oxide (5.30 g) in water (50 ml) is added to a solution of (±)-3-(5′-indanyl)-5-(iodomethyl)oxazolidin-2-one (XVIIIA, EXAMPLE 43, 3.726 g, 10.86 mmol) in acetone (250 ml). The mixture is heated at reflux behind a safety shield for 27 hr, stirred at 20°–25° overnight, then poured into water (350 ml) and extracted with ethyl acetate (3×175 ml). The combined extracts are washed with water (50 ml), followed by saline (50 ml), dried over magnesium sulfate and concentrated under reduced pressure (safety shield) to give an oil, which on standing at 0° crystallized. NMR analysis indicates the title compound with only a small amount of residual mineral oil; this material is used without attempted upgrading. NMR (CDCl$_3$, 300 MHz) 7.46, 7.22, 4.76, 4.09, 3.86, 3.58, 2.90 and 2.09 δ; IR (CHCl$_3$) 2120, 1760, 1489 and 1410 cm$^{-1}$; MS (m/e) 258, 230, 201, 185, 170, 158, 144, 130 and 117, exact mass calculated for $C_{13}H_{14}N_4O_2 = 258.1117$, found 258.1132.

EXAMPLE 45

(±)-3-(5′-Indanyl)-5-(aminoethyl)oxazolidin-2-one (XXA)

A solution of (±)-3-(5′-indanyl)-5-(azidomethyl)oxazolidin-2-one (XIXA, EXAMPLE 44, 305 g, slightly impure) in ethyl acetate (600 ml, freshly opened, Fisher HPLC grade), is evacuated (20 Torr) and filled with argon (4×). Then palladium/carbon (10%, 1.276 g) is added, and the system evacuated and filled with hydrogen from a balloon (4×). The mixture was stirred at 20°–25° for 19 hr. TLC analysis shows a trace of starting material, so more hydrogen is added via a fresh balloon. After starting an additional 2.25 hr, the mixture is filtered thru diatomaceous earth, washing the pad first with ethyl acetate, then methanol/ethyl acetate (10/90). The filtrate is concentrated under reduced pressure to give a solid. This is deemed of sufficient quality for further use.

For an analytical sample, approximately 50 mg is dissolved in chloroform and loaded onto a 2 inch silica gel plug in a pipette. This is eluted with ethyl acetate to remove less polar impurities, then methanol/ethyl acetate (1/1). The eluate is concentrated to give the title compound, mp 101°–103°; NMR (CDCl$_3$, 300 MHz) 7.45, 7.21, 4.65, 4.03, 3.81, 3.07, 2.99, 2.89, 2.07 and 1.58 δ; CMR (CDCl$_3$, 75.47 MHz) 25.55, 32.19, 33.02, 45.06, 48.15, 73.73, 115.00, 116.52, 124.47, 136.36, 140.16 and 145.27 δ; IR (CHCl$_3$) 3688, 3390, 1745, 1614, 1484 and 1404 cm$^{-1}$; MS (m/e) 232, 203, 187, 171, 159 and 146, exact mass calculated for $C_{13}H_{16}O_2N_2 = 232.1212$, found 232.1214.

EXAMPLE 46

(±)-3-(5′-Indanyl)-5-(acetamidomethyl)oxazolidin-2-one (XXIA)

Acetic anhydride (1.5 ml) is added to a solution of (±)-3-(5′-indanyl)-5-(aminomethyl)oxazolidin-2-one (XXA, EXAMPLE 45, 0.472 g) in pyridine (3.0 ml) over a period of 2 min with a slight exotherm. The mixture is stirred at 20°–25° for 21 hr, then concentrated under reduced pressure to give an oil. The oil is transferred to a Erlenmeyer flask (50 ml) containing chloroform (10 ml) and ethyl acetate (20 ml) is added. The mixture is concentrated under a gentle nitrogen flow to give the title compound, mp 133°–134°; NMR (CDCl$_3$, 300 MHz) 7.37, 7.19, 7.06, 4.74, 4.02, 3.78, 3.60, 2.87, 2.06 and 2.00 δ; CMR (CDCl$_3$, 75.47 MHz) 22.94, 25.60, 32.25, 33.04, 41.86, 48.12, 72.00, 115.28, 116.91, 124.58, 136.09, 140.54, 145.54, 145.34, 154.98, 171.44 δ; IR (mineral oil mull) 3344, 2925, 1739, 1663, 1551 and 1419 cm$^{-1}$; MS (m/e) 274, 230, 215, 202, 187, 171, 170, 158, 146, 133 and 117, exact mass calculated for C$_{15}$H$_{18}$N$_2$O$_3$=274.1317, found 274.1322.

EXAMPLE 47

(±)-3-(5′-Indanyl)-5-(butyramidomethyl)oxazolidin-2-one (XXIA)

Following the general procedure of EXAMPLE 46 and making non-critical variations but starting with butyric anhydride, the title compound is obtained, NMR (CDCl$_3$, 300 MHz) 7.39, 7.20, 6.5, 4.75, 4.03, 3.78, 3.64, 2.88, 2.19, 2.08 and 1.63 δ; CMR (CDCl$_3$, 75.47 MHz) 15.53, 18.91, 25.44, 32.11, 32.90, 38.22, 41.68, 47.96, 71.76, 115.04, 116.64, 124.43, 136.1, 140.6, 145.5, 155.0 and 174.0 δ; IR (mineral oil mull) 3349, 2959, 2927, 2855, 1736, 1656, 1544, 1495, 1468 and 1420 cm$^{-1}$; MS (m/e) 302, 274, 258, 215, 202, 187, 171, 146 and 133, exact mass calculated for C$_{17}$H$_{22}$N$_2$O$_3$=302.1630, found 302.1633.

EXAMPLE 48

(±)-3-(5′-Indanyl)-5-(cyclopropylcarboxamido)methyl oxazolidin-2-one (XXIA)

Triethylamine (0.139 g, 0.19 ml) is added to a mixture of (±)-3-(5′-indanyl)-5-(aminomethyl)oxazolidin-2-one (XXA, EXAMPLE 45, 0.236 g) in methylene chloride (5.0 ml). The mixture is cooled to 0° under argon, and then cyclopropane carbonyl chloride (0.143 g, 0.125 ml) is added dropwise over about 7 min. The mixture is stirred at 0° for 30 min, then allowed to warm to 20°–25°. TLC analysis indicates complete conversion, and the mixture is concentrated under reduced pressure. The solid residue is purified by column chromatography on silica gel (60–200μ, 11 cm×2.5 cm, 25 ml fractions), loading as a solution in chloroform, then eluting with ethyl acetate. The appropriate fractions are pooled to give the title compounds, mp 145°–147°; NMR (CDCl$_3$, 300 MHz) 7.195, 7.20, 6.55, 4.75, 4.02, 3.79, 3.67, 2.88, 2.075, 1.42, 0.92 and 0.74 δ; CMR (CDCl$_3$, 75.47 MHz) 7.52, 7.62, 14.54, 23.61, 32.26, 33.06, 42.01, 48.13, 72.03, 115.32, 116.92, 124.58, 136.16, 140.60, 145.48, 154.91 and 174.89 δ; IR (mineral oil mull) 3305, 2954, 2924, 2854, 1746, 1666, 1554, 1496 and 1422 cm$^{-1}$; MS (m/e) 300, 256, 215, 202, 185, 171, 158, 146 and 133, exact mass calculated for C$_{17}$H$_{20}$N$_2$O$_3$=300.1474, found 300.1480.

EXAMPLE 49

(±)-3-(5′-Indanyl)-5-(formylamidomethyl)oxazolidin-2-one (XXIA)

A mixture of (±)-3-(5′-indanyl)-5-(aminomethyl)oxazolidin-2-one (XXA, EXAMPLE 45, 0.139 g) in formic acid (1.0 ml) and acetic anhydride (0.2 ml) is stirred at 20° for 2 days, then concentrated under reduced pressure to give a brown oil, NMR analysis indicates clean conversion. The residue is taken up in chloroform and ethyl acetate and the mixture is concentrated under a stream of nitrogen to give the title compound; NMR (CDCl$_3$, 300 MHz) 8.23, 7.36, 7.19, 7.04, 4.76, 4.03, 3.80, 3.77–3.58, 2.87 and 2.05 δ; CMR (CDCl$_3$) 25.60, 32.26, 33.05, 40.28, 48.12, 71.68, 115.40, 117.03, 124.64, 135.90, 140.77, 145.44, 154.6 and 162.3 δ; IR (CHCl$_3$) 3430, 3315, 1750, 1689 and 1482 cm$^{-1}$; MS (m/e) 260, 216, 202, 170, 158, 146, 133 and 117; exact mass calculated for C$_{14}$H$_{16}$N$_2$O$_3$=260.1161, found 260.1174.

EXAMPLE 50

(±)-3-(5′-Indanyl)-5-(benzamidomethyl)oxazolidin-2-one (XXIA)

Benzoyl chloride (0.31 g, 0.26 ml) is added to a solution of (±)-3-(5′-indanyl)-5-(aminomethyl)oxazolidin-2-one (XXA, EXAMPLE 45, 0.518 g) in pyridine (4.0 ml) at 0° under argon over a period of 1 min. The mixture is stirred at 0° for about 1 hr., then allowed to warm to 20°–25° for a total of 23 hr. TLC analysis showes residual starting material, so benzoyl chloride (0.1 ml) is added after again cooling to 0°, and after 5 hr the reaction is completer. The mixture is concentrated under reduced pressure to give an oil with crystals. This material is chromatographed using MPLC (2.5 cm×22 cm silica gel, 40–63μ, with a gradient elution with 25%, 50%, 75%, and 100% ethyl acetate/hexane). The appropriate fractions are pooled and concentrated to give the title compound, mp 159.8°–161°. For analysis, a portion is dissolved in chloroform and ethyl acetate and concentrated under a stream of nitrogen to provide crystalline material, NMR (CDCl$_3$, 300 MHz) 7.81, 7.78, 7.47, 7.37, 7.26, 7.18, 7.15, 4.84, 4.06, 3.92–3.72, 2.85 and 2.04 δ; CMR (CDCl$_3$, 75.47 MHz) 25.50, 32.16, 32.95, 42.52, 48.26, 71.93, 115.24, 116.84, 124.49, 127.09, 128.47, 131.72, 133.56, 135.97, 140.47, 145.26, 154.80 and 168.29 δ; IR (mineral oil mull) 3367, 2949, 2915, 1757, 1654, 1551, 1491 and 1408 cm$^{-1}$; MS (m/e) 336, 292, 215, 202, 187, 171, 158, 146, 133 and 105, exact mass calculated for C$_{20}$H$_{20}$N$_2$O$_3$−336.1474, found 336.1472.

EXAMPLE 51

(±)-3-(5′-Indanyl)-5-(methoxycarboxamidomethyl)oxazolidin-2-one (XXIA)

Triethylamine (56 μl) followed by methyl chloroformate (36 μl) is added to a mixture (±)-3-(5′-indanyl)-5-(aminomethyl)oxazolidin-2-one (XXA, EXAMPLE 45, 0.085 g) in methylene chloride (3.0 ml) under argon at 0°. The mixture is stirred at 0° for 45 min, then allowed to warm to 20°–25°. After a total of 19 hr, the mixture is concentrated under reduced pressure to give a residue. The residue is purified by gravity chromatography through a short silica gel column in a pipette (2″), loading with chloroform, and then eluting with ethyl acetate/hexane (1/1). The eluate is concentrated to give the title compound, NMR (CDCl$_3$, 300 MHz), 7.42, 7.20, 5.31, 4.74, 4.04, 3.79, 3.68, 3.61–3.46, 2.90 and 2.08 δ; CMR (CDCl$_3$, 75.47 MHz) 25.63, 32.37, 33.08, 43.75, 47.97, 52.54, 71.71, 115.19, 116.74, 124.59, 136.15, 140.50, 145.41, 154.9 and 157.7 δ.

EXAMPLE 52

(±)-3-(1′-Oxo-5′-indanyl)-5-(acetamidomethyl)oxazolidin-2-one (XXIB)

A solution of chromium trioxide (1.09 g) dissolved in glacial acetic acid (14 ml) and water (4 ml) is added to a solution of (±)-3-(5′-indanyl)-5-(acetamidomethyl)oxazolidin-2-one (XXIA, EXAMPLE 46, 1.198 g) in glacial acetic acid (25 ml) and acetic anhydride (4 ml) at 20°-25°. A mild exotherm is observed. The mixture is stirred at 20°-25° for 2 hr., then poured into ice (250 g) and allowed to stand for 20 min. The pH is then adjusted by the careful addition of saturated aqueous sodium bicarbonate to 7-7.5. The mixture is extracted with ethyl acetate (5×200 ml), then with methylene chloride (3×200 ml). The extracts are washed with saline, dried over magnesium sulfate, and concentrated under reduced pressure to give an oil. The oil is taken up in chloroform and concentrated under reduced pressure to give a solid. A portion of the solid is purified by silica gel flash chromatography (0.5×5 cm column, eluting with chloroform, then ethyl acetate, followed by a gradient of methanol-ethyl acetate. The appropriate factions are pooled in give the title compound, NMR (CDCl$_3$, 300 MHz) 7.71, 7.65, 7.51, 6.77, 4.84, 4.13, 3.90, 3.12, 2.69, and 2.04 δ; CMR (CDCl$_3$, 75.47 MHz) 23.06, 36.41, 41.80, 47.63, 72.20, 115.03, 117.08, 124.67, 132.74, 143.56, 154.25, 156.74, 171.45 and 205.74 δ; IR (CHCl$_3$) 3440, 1757, 1694, 1605, 1480, 1400, 1280, and 1130 cm$^{-1}$; MS (m/e) 288, 244, 229, 216, 201, 185, 160 and 147; exact mass calcd for $C_{15}H_{16}O_4N_2 = 288.1110$, found 288.1101.

EXAMPLE 53

(±)-3-(1-Oximino-5'-indanyl)-5-(acetamidomethyl)oxazolidin-2-one (XXIE)

A mixture of (±)-3-(1'-oxo-5'-indanyl)-5-(acetamidomethyl)oxazolidin-2-one (XXIB, EXAMPLE 52, 0.172 g) and hydroxylamine hydrochloride (0.448 g) in methanol (10 ml) and water (5 ml) is stirred at 20°-25°. Then saturated aqueous sodium bicarbonate (12.5 ml) is slowly added over about 10 min. The mixture is stirred for 19 hr., then poured into water (50 ml) and extracted with ethyl acetate (2×40 ml, then 2×25 ml) and then methylene chloride (6×25 ml). The organic extracts are washed with saline, dried over magnesium sulfate and concentrated under reduced pressure to give a solid as a mixture of syn and anti isomers; mp 144°-160°; Major isomer: NMR (CDCl$_3$+CD$_3$OD, 300 MHz) 7.65, 7.54, 7.44, 4.8, 4.16, 3.85, 3.59, 3.06, 2.94, and 2.00 δ; minor isomer (unobscured peaks; relative ratio to major isomer=1:5.6) 8.42, 7.73, 4.23, 3.92, 3.19, 2.84, and 2.72; IR (mineral oil mull) 3293, 1746, 1657, 1408, and 1225 cm$^{-1}$.

EXAMPLE 54

(±)-3-(1'-Hydroxy-5'-indanyl)-5-(acetamidomethyl)oxazolidin-2-one (XXIC)

Sodium borohydride (0.023 g) is added to a solution of (±)-3-(1'-oxo-5'-indanyl)-5-(acetamidomethyl)oxazolidin-2-one (XXIB, EXAMPLE 52, 0.044 g) in absolute ethanol (5 ml) at 20°-25°. The mixture is stirred for 2.5 hr, then analyzed by TLC. Additional sodium borohydride (0.026 g) is added. After a total of 22 hr, acetone is added, and the mixture concentrated to ½ volume, then poured into dilute aqueous hydrochloric acid (0.25N, 6 ml in 20 ml water), and the mixture extracted with ethyl acetate (5×10 ml). The combined organic extracts are washed with saturated aqueous sodium bicarbonate, dried over magnesium sulfate and concentrated under reduced pressure to givre an oil. Additional material is recovered by continued extraction of the aqueous layer with ethyl acetate. A 10 mg sample is chromatographed on silica gel (4 cm×0.5 cm, 40-63μ), eluting with a gradient of ethyl acetate-methanol. The appropriate fractions are pooled and concentrated to give the title componds as a mixture of diastereomers A and B, and of the more polar diastereomer B, as oils. Diastereomeric mixture NMR (CDCl$_3$, 300 MHz) 7.5-7.3, 6.60, 5.21, 4.73, 4.03, 3.76, 3.62, 3.02, 2.80, 2.46, 2.00, and 1.95 δ; IR (CHCl$_3$) 3680, 3600, 3440, 1750, 1674, and 1405 cm$^{-1}$; MS exact mass calcd for $C_{15}H_{18}O_4N_2 = 290.1226$, found 290.1277.

EXAMPLE 55

(±)-3-(6'-Tetralinyl)-5-(acetamidomethyl)oxazolidine-2-one (XXIA)

Following the general procedure of EXAMPLES 41-46 and making non-critical varations but starting with 6-aminotetralin, the title compound is obtained.

EXAMPLE 56

(+)-3-(1'-Oxo-6'-tetralinyl)-5-(acetamidomethyl)oxazolidin-2-one (XXIB)

Following the general procedure of EXAMPLE 52 and making non-critical variations but starting with (±)-3-(6'-tetralinyl)-5-(acetamidomethyl)oxazolidin-2-one (XXIA, EXAMPLE 55), the title compound is obtained.

EXAMPLE 57

1-Carbo-t-butyloxy-5-nitroindazole (XXIII)

A mixture of 5-nitroindazole (XXII, 5.685) and di-t-butyl dicarbonate (15.325 g) is stirred for four days in refluxing THF (freshly distilled, 220 ml) under nitrogen. The mixture is then concentrated to 70 ml, by distillation, and then poured over crushed ice (600 ml). After the ice melts, the mixture is filtered using reduce pressure. The precipitate is dried in a vacuum over to give a solid. A small amount (536 mg) of this product is purified by passing it through a silica gel column (23.5×2.5 cm, 40-63μ) eluting with ethyl acetate/hexane (⅓, 700 m and then 1/1 200 ml). The appropriate fractions are pooled and concentrated to a solid. The solid is recrystallized from acetone to give the title compound, NMR (CDCl$_3$, 300 MHz) 8.71, 8.43-8.32 and 1.76 δ; CMR (CDCl$_3$, 75.47 MHz) 27.91, 86.19, 114.956, 117.82, 123.54, 125.27, 140.06, 141.79, 144.08 and 148.30 δ; IR (mineral oil mull) 1765, 1532, 1383, 1347, 1291, 1155 and 1151 cm$^{-1}$; MS (m/e) 263, 204, 163, 57 and 40.

EXAMPLE 58

1-Carbo-t-butyloxy-5-aminoindazole (XXIV)

To a solution of 1-carbo-t-butyloxy-5-nitroindazole (XXIII, EXAMPLE 57, 6.165 g) in ethyl acetate (125 ml) is added palladium on carbon (10%, 734 mg). The mixture is stirred under hydrogen (1 atm. balloon) at 20°-25°. After stirring for 27 hours, more palladium on carbon (10%, 294 mg) is added. Then, after stirring for an additional two days under hydrogen, the mixture is filtered over dicalite and the filtrate is concentrated to an oil. The oil is taken up in ethyl acetate (125 ml), dried over magnesium sulfate and concentrated to an oil. The oil is passed over a silica column (27×4.5 cm, 40-63μ) eluting with ethyl acetate/hexane (⅓, 500 ml followed by 1/1 1000 ml), ethyl acetate (1000 ml) and methanol/ethyl acetate (1/9, 1000 ml). The appropriate fractions are pooled and concentrated to give the title compound, NMR (CDCl$_3$, 300 MHz) 7.99-7.94, 6.97-6.91, 3.77 and 1.71 δ; CMR (CDCl$_3$, 75.47 MHz) 28.06, 84.335, 103.82, 115.05, 119.35, 126.84, 134.07, 138.68, 142.64 and 149.13 δ; IR (mineral oil mull) 1736, 1518, 1462, 1375, 1301, 1232 and 1145 cm$^{-1}$; MS (m/e) 233, 133, 105, 57 and 40.

EXAMPLE 59

1-Carbo-t-butyloxy-5-(N-carbovenzyloxy)aminoindazole (XXV)

Benzyl chloroformate (2.45 ml) is added to a mixture of 1-carbo-t-butyloxy-5-aminoindazole (XXIV, EXAMPLE 58, 3.760 g) and sodium bicarbonate (2.721 g) in acetone/water (1/1, 50 ml) at 0° over one minute. The mixture is stirred under nitrogen for 1.5 hr then poured into water (50 ml). The aqueous mixture is then extracted with ethyl acetate (3×, 250 ml total). The combined organic layers are washed with aqueous sodium bisulfate (10%, 125 ml), aqueous sodium bicarbonate (10%, 125 ml), saline (125 ml), dried over magnesium sulfate, and concentrated to a give the title compounds as a solid, NMR (CDCl$_3$, 300 MHz) 8.08–7.98, 7.48–7.27, 5.20 and 1.70 δ; CMR (CDCl$_3$, 75.47 MHz) 28.03, 66.99, 84.82, 109.7, 114.77, 121.1, 126.19, 128.19, 128.26, 128.50, 133.93, 135.84, 136.20, 139.32, 149.00 and 153.59 δ; IR (mineral oil mull) 1746, 1726, 1521, 1395, 1355, 1290, 1218 and 1044 cm$^{-1}$; MS (m/e) 367, 267, 223, 132, 91, 57 and 40.

EXAMPLE 60

1-Carbo-t-butyloxy-5-(N-allyl-N-carbobenzyloxy)aminoindazole (XXVI)

1-Allyl-5-(N-allyl-N-carbobenzyloxy)aminoindazole (XXVI')

Allyl bromide (1.70 ml) is added to a mixture of 1-carbo-t-butyloxy-5-(N-carbobenzyloxy)aminoindazole (XXV, EXAMPLE 59, 5.805 g) and sodium hydride/mineral oil (50% by weight, 1.000 g, 15.8 mmol sodium hydride) in freshly distilled THF (80 ml). The mixture is refluxed for 20 hr under nitrogen, then poured into water (100 ml). The aqueous mixture is extracted with ethyl acetate (3×100 ml). The combined organic layers are washed with saline, dried over magnesium sulfate, and concentrated to an oil. The oil is passed over a silica gel column (26×4.5 cm, 40–63μ), eluting with ethyl acetate/hexane (1/4 2 1, 1/1 1 1) and ethyl acetate (300 ml) collecting 47 ml fractions. The appropriate fractions are pooled and concentrated give 1-carbo-t-butyloxy-5-(N-allyl-N-carbobenzyloxy)aminoindazole (XXVI) NMR (CDCl$_3$, 300 MHz) 8.14, 7.59, 7.34, 5.93, 5.16, 5.11, 4.32, and 1.71 δ; CMR (CDCl$_3$, 75.47 MHz) 27.99, 53.53, 67.32, 84.91, 114.51, 114.75, 126.00, 127.56, 127.85, 128.30, 132.67, 133.294, 137.93, 139.24, 148.87 and 155.24 δ; MS (m/e) 407, 307, 172, 91, 57 and 40. Later eluting fractions are pooled and concentrated give 1-allyl-5-(N-allyl-N-carbobenzyloxy)aminoindazole (XXVI') NMR (CDCl$_3$, 300 MHz) 7.91, 7.68, 7.47, 7.28, 7.14, 6.18–6.05, 6.00–5.87, 5.37–5.29, 5.16–5.11, 5.04–5.01 and 4.29 δ; CMR (CDCl$_3$, 74.47 MHz, major peaks) 53.39, 55.91, 67.08, 117.20, 117.56, 117.93, 119.28, 121.48, 123.12, 126.72, 127.43, 127.70, 128.25, 132.07, 133.65, 135.55, 147.39 and 155.46 δ.

EXAMPLE 61

(±)-3-[5'-(1-Carbo-t-butyloxyindazolyl)]-5-(iodomethyl)oxazolidin-2-one (XXVII)

(±)-3-[5'-(1-Allylindazolyl)]-5-(iodomethyl)oxazolidin-2-one (XXVII')

Iodine (4.699 g) is added to 4.580 g of a mixture of 1-carbo-t-butyloxy-5-(N-allyl-N-carbobenzyloxy)aminoindazole (XXVI, EXAMPLE 60) and 1-allyl-5-(N-allyl-N-carbobenzyloxy)aminoindazole (XXVI', EXAMPLE 60) in chloroform (95 ml). The mixture is stirred under nitrogen for 1.5 hr then poured into aqueous sodium thiosulfate (10%, 100 ml). The layers are separated, and the organic layer is washed with additional aqueous sodium thiosulfate (10%, 2×50 ml). The aqueous layers are combined and extracted with ethyl acetate (3×, 200 ml total). The organic layers are combined, dried over magnesium sulfate and concentrated to give an oil. The oil is adsorbed onto silica gel (40–63μ) then placed on a silica gel column (35×5.5 cm, 40–63μ) eluting with ethyl acetate/hexane (⅓, 500 ml; 1/1, 2 1) and methanol/ethyl acetate (1/9, 2 1) collecting 41 ml fractions. The appropriate fractions are pooled and concentrated give (±)-3-[5'-(1-allylindazolyl)]-5-(iodoomethyl)oxazolidin-2-one (XXVII'), NMR (CDCl$_3$, 300 MHz) 7.98, 7.72, 7.68, 7.4, 6.01, 5.22, 5.14, 5.08, 5.02, 5.00, 4.73, 4.23, 3.84, 3.47 and 3.39 δ; CMR (CDCl$_3$, 75.47 MHz) 6.29, 51.76, 51.87, 71.09, 109.86, 110.86, 117.76, 119.68, 123.97, 131.30, 132.45, 132.98, 136.90 and 154.4; IR (Neat) 1746, 1510, 1417, 1226 and 1112 cm$^{-1}$; MS (m/e) 383, 255, 212, 184, 170, 157 and 40.

Later eluting fractions are pooled and concentrated give (±)-3-[5'-(1-carbo-t-butyloxyindazolyl)]-5-(iodomethyl)oxazolidin-2-one (XXVII) which is recrystallized from acetone, NMR (CDCl$_3$, 300 MHz) 8.18, 7.87, 7.78, 4.78, 4.27, 3.88, 3.51, 3.41 and 1.73 δ; CMR (CDCl$_3$, 75.47 MHz) 5.95, 28.04, 51.42, 71.14, 85.04, 110.16, 115.01, 120.51, 125.98, 133.85, 136.8, 139.22, 149.1 and 154.5 δ; IR (mineral oil mull) 1745, 1390 and 1155 cm$^{-1}$; MS (m/e) 443, 343, 172, 144, 117, 57 and 40.

EXAMPLE 62

(±)-3-(5'-Indazolyl)-5-(azidomethyl)oxazolidin-2-one (XXVIII)

(±)-3-[5'-(1-Allylindazolyl)]-5-(azidomethyl)oxazolidin-2-one (XXVIII')

A mixture (2.515 g) of (±)-3-[5'-(1-carbo-t-butloxyindazolyl)]-5-(iodomethyl)oxazolidin-2-one (XXVII, EXAMPLE 61) and (±)-3-[5'-(1-allylindazolyl)]-5-(iodomethyl)oxazolidin-2-one (XXVII', EXAMPLE 61) is stirred with sodium azide (2.575 g) in refluxing water/acetone (½, 150 ml) under nitrogen for 25 hr. The mixture is then poured into ethyl acetate (100 ml). The layers are separated. The aqueous phase is extracted with ethyl acetate (3×25 ml). The combined organic layers are dried over magnesium sulfate and concentrated to an oil. A sample of the oil is purified by preparative TLC. From the purification (±)-3-(5'-indazolyl)-5-(azidomethyl)oxazolidin-2-one (XXVIII), NMR (CDCl$_3$ ca. 0.5% DMF-d$_7$, 300 MHz) 9.5–8.5, 8.02, 7.69, 7.55, 4.84, 4.20, 3.92, 3.74 and 3.62 δ; CMR (CDCl$_3$, ca. 0.5% DMF. d$_7$, 75.47 Mhz, 300 MHz) 48.24, 52.96, 70.66, 110.38, 110.75, 122.8, 131.5, 133.9, 137.8 and 154.9 δ; IR (neat) 2108, 1741, 1511, 1420 and 1277 and (±)-3-[5'-(1-allylindazolyl)]-5-(azidomethyl)oxazolidin-2-one (XXVIII′) NMR (CDCl₃, 300 MHz) 7.99, 7.74, 7.68, 7.42, 6.02, 5.23, 5.12, 5.02, 4.82, 4.16, 3.94, 3.73 and 3.62 $\delta$; CMR (CDCl₃, 75.47 MHz) 48.33, 51.78, 52.98, 70.54, 109.88, 110.79, 117.76, 119.65, 124.1, 131.7, 132.42, 132.98, 137.3 and 154.6 $\delta$; IR (neat) 2105, 1746, 1510, 1418 and 1224 cm⁻¹.

EXAMPLE 63

(±)-3-(5′-Indazolyl)-5-(aminomethyl)oxazolidin-2-one (XXIX)

(±)-3-[5′-(1-n-Propylindazolyl)]-5-(aminomethyl)oxazolidin-2-one (XXIX′)

Palladium on carbon (10%, 540 mg) is added to a combined mixture (2.000 g) of (±)-3-(5′-indazolyl)-5-(azidomethyl)oxazolidin-2-one (XXVIII, EXAMPLE 62) and (±)-3-[5′-(1-allylindazolyl)]-5-(azidomethyl)oxazolidin-2-one (XXVIII′, EXAMPLE 62) in methanol-/ethyl acetate (105, 110 ml). The mixture is stirred under 1 atm of hydrogen (balloon) overnight. The mixture is then filtered over diatomaceous earth and the filtrate concentrated to a tar. The crude material is dissolved and is passed over a silica gel column (23×3 cm, 40—63μ) eluting with methanol/chloroform (1/9, 600 ml, ¼, 1.5 l) collecting 46 ml fractions. The appropriate fractions are pooled and concentrated give (±)-3-[5′-(1-n-propylindazolyl)]-5-(aminomethyl)oxazolidin-2-one (XXIX′), NMR (MeOD, 300 MHz) 7.96, 7.73, 7.52, 4.71, 4.31, 4.14, 3.87, 2.98, 1.87 and 0.84 $\delta$; CMR (MeOD, 75.47 MHz) 11.64, 24.35, 45.61, 50.12, 51.37, 75.62, 110.96, 112.42, 121.60, 124.95, 133.32, 133.81, 138.50 and 157.50 $\delta$; IR (neat) 1741, 1510, 1418, 1225 and 1113 cm⁻¹. Later eluting fractions are pooled and concentrated give (±)-3-(5′-indazolyl)-5-(aminomethyl)oxazolidin-2-ones (XXIX), NMR (MeOD, 300 MHz) 8.02, 7.77, 7.70, 7.55, 4.78, 4.17, 3.89 and 3.05 $\delta$; CMR (MeOD, 75.47 MHz) 45.43, 50.35, 75.35, 111.76, 112.52, 122.02, 124.19, 133.16, 134.99, 139.20 and 157.60 $\delta$; IR (neat) 3800–3000 very broad, 1735, 1511 and 1423 cm⁻¹.

EXAMPLE 64

(±)-3-[5′-(1-Acetylindazolyl)]-5-(acetamidomethyl)oxazolidin-2-one (XXX)

(±)-3-(5′-Indazolyl)-5-(acetamidomethyl)oxazolidin-2-one (XXXI)

Acetic anhydride (0.5 ml) is added to (±)-3-(5′-indazolyl)-5-(aminomethyl)oxazolidin-2-one (XXIX, EXAMPLE 63, 152 mg) in pyridine (1.5 ml) at 0°. The mixture is stirred for two hr. while allowing it to warm to 20°-25°. The mixture is then concentrated under reduced pressure to a solid. The solid is purified on a silica preparative plate (1000μ) developing with methanol/chloroform (1/10) to give (±)-3-(5′-(1-acetylindazolyl))-5-acetamidomethyl-2-oxazolidin-2-one (XXX), NMR (CH₃OD, 300 MHz) 8.03, 7.76, 7.70, 7.54, 4.79, 4.20, 3.89, 3.58 and 1.98 $\delta$; CMR (CH₃OD, 75.47 MHz) 22.49, 43.23, 50.28, 73.58, 111.70, 112.43, 124.3, 133.5, 135.2, 139.6, 157.9 and 174.5 $\delta$ and (±)-3-(5′-indazolyl)-5-acetamidomethyl-2-oxazolidin-2-one (XXXI), NMR (CDCl₃, 300 MHz) 8.37, 8.08, 7.85, 7.69, 6.61, 4.83, 4.14, 3.91, 3.70, 2.78 and 2.04 $\delta$; CMR (CDCl₃, 75.47 MHz) 22.73, 22.93, 41.77, 47.94, 71.95, 109.92, 115.82, 120.64, 126.51, 134.55, 135.6, 139.37, 154.5, 170.75 and 171.16 $\delta$.

EXAMPLE 65

(±)-3-[5′-(1-Ethylindazolyl)]-5-(acetamidomethyl)oxazolidin-2-one (XXXII)

Starting with (±)-3-(5′-indazolyl)-5-(acetamidomethyl)oxazolidin-2-one (XXXI, EXAMPLE 64) in methanol and acetaldehyde (2 equivalents), the mixture is treated with glacial acetic acid to bring the ph to 5. After stirring the mixture for 1-2 hr, 1 equivalent of sodium cyanoborohydride is added and the mixture is stirred for 24 hr at 20°-25°. The mixture is then concentrated under reduced pressue. Water is added, and the pH is adjusted to 7.8 with 1N aqueous potassium hydroxide, then extracted with chloroform (3×). The organic extracts are combined, dried over magnesium sulfate and concentrated under reduced pressure to give the title compound. It can be purified by recrystallization or column chromatography on silica gel if desired.

EXAMPLE 66

(±)-3-[5′-(1-n-Propylindazolyl)]-5-(acetamidomethyl)oxazolidin-2-one (XXX′)

Acetic anhydride (0.5 ml) is added to (±)-3-[5′-(1-n-propylindazolyl)]-5-(aminomethyl)oxazolidin-2-one (XXIX′, EXAMPLE 63, 126 mg) in pyridine (1.5 ml) at 0°. The mixture is stirred for two hr while allowing it to warm to 20°-25°. The mixture is then concentrated under reduced pressure to a solid. The solid is purified on a silica preparative plate (1000μ) developing with with methanol/chloroform (1/10) to give the title compound, NMR (CDCl₃, 300 MHz) 7.95, 7.66, 7.39, 6.91, 4.80, 4.33, 4.10, 3.89, 3.66, 2.02, 1.93 and 0.90 $\delta$; CMR (CDCl₃, 75.47 MHz): $\delta$ 11.22, 22.84, 23.09, 41.81, 48.53, 50.53, 71.98, 109.51, 110.98, 119.53, 123.62, 1312.11, 132.47, 136.92, 155.19 and 171.27 $\delta$.

EXAMPLE 67

1-Ethyl-2-methyl-(N-carbobenzyloxy)-5-aminobenzimidazole (XXXVI)

A aqueous sodium bicarbonate solution (0.137 g/ml) is very slowly added to a solution of 1-ethyl-2-methyl-5-aminobenzimidazole hydrochloride (XXXV, 9.715 g) in water (50 ml). A precipitate formes from the effervescent mixture. The precipitate is dissolved by adding acetone (50 ml), and remained in solution after adding another 70 ml of the sodium bicarbonate solution (13.667 g sodium bicarbonate total). After the mixture is cooled to 0° under nitrogen, benzylchloroformate (5.7 ml) is added slowly over two min. The mixture is then slowly warmed to 20°-25°. More acetone is added (100 ml) to dissolve a precipitate than is formed. After 22 hrs benzylchloroformate (150 μl) is added. Then after 2.5 hrs the mixture is poured into ethylacetate. The layers are separated, and the aqueous phase is extracted with ethyl acetate, 4×. The combined organic layers are washed with aqueous sodium bisulfate (10%, 2×), which removed the color. The desired product is in the aqueous sodium bisulfate washings. These aqueous layers are made alkaline (pH ~14) with sodium hydroxide (5N). A solid is obtained after filtering the alkaline mixture. The solid is then triturated in boiling acetone, 4 ×, filtering after each trituration. The filtrates are combined and concentrated to give the title compound, mp 145-150; NMR (CDCl₃, 300 MHz) 7.58, 7.4-7.26, 7.18, 5.20, 4.08, 2.54, 1.35 $\delta$; CMR (CDCl₃, 75.47 MHz) 13.56, 14.78, 33.42, 66.67, 108.84, 109.6, 115.2, 128.06, 128.11, 128.41, 131.7, 132.8, 135.24, 142.66, 151.68 and 154.1 δ; IR (mineral oil mull) 1723, 1569, 1496, 1240 and 1060 cm$^{-1}$; MS (m/e) 309, 174 and 91; exact mass calcd for $C_{18}H_{19}N_5O_2$ = 309.1477, found 309,1495.

EXAMPLE 68

1-Ethyl-2-methyl-(N-allyl-N-carbobenzyloxy)-5-aminobenzimidazole (XXXVII)

Allyl bromide (2.5 ml) is added to a mixture of 1-ethyl-2-methyl-(N-carbobenzyloxy)-5-aminobenzimidazole (XXXVI, EXAMPLE 67, 6.780 g) and sodium hydride/mineral oil (50% by weight, 1.374 g, 28.6 mmol NaH) in freshly distilled THF (150 ml). The mixture is refluxed under nitrogen. After 21 hrs, the mixture is poured into water (100 ml) and extracted with ethyl acetate (3×200 ml). The organic layers are combined, dried over magnesium sulfate and concentrated under reduced pressure to give an oil. A portion of this oil (509 mg) is passed over a silica column (34×2.5 cm, 40–63μ) eluting with ethyl acetate/hexane (70/30, 700 ml) and 1500 ml ethyl acetate. The appropriate fractions are pooled and concentrated to give the title compound as an oil, NMR (CDCl$_3$, 300 MHz) 7.53, 7.23–7.09, 5.91, 5.10, 4.30, 3.97, 2.49, and 1.28 δ; CMR (CDCl$_3$, 74.47 MHz) 13.50, 14.67, 38.30, 53.91, 66.90, 108.71, 117.14, 117.46, 121.30, 127.30, 127.54, 128.15, 133.25, 133.58, 136.5, 136.65, 142.65, 141.95 and 155.50 δ; IR (Mineral oil mull) 1698, 1402, 1409 and 1245 cm$^{-1}$; MS (m/e) 349, 214, 186, 184, 159, 92 and 91; exact mass calcd for $C_{21}H_{23}N_3O_2$ = 349.1790, found 349.1786.

EXAMPLE 69

(±)-3-(5'-1-Ethyl-2-methylbenzimidazolyl)-5-(iodomethyl)oxazolidin-2-one (XXXVIII)

Iodine (25.372 g) is added to a mixture of 1-ethyl-2-methyl-(N-allyl-N-carbobenzyloxy)-5-aminobenzimidazole (XXXVII, EXAMPLE 68, 7.790 g) in chloroform (200 ml). After 25 min the mixture is poured into aqueous sodium thiosulfate (10%, 100 ml) and the layers are separated. The organic layer is washed again with sodium thiosulfate (10%, 3×, 250 ml total). The organic phases are combined and dried over magnesium sulfate and concentrated to give a solid. The solid is dissolved in methylene chloride and passed over a silica column (36×5.5 cm, 40–63μ). The column is eluted with methylene chloride and methanol/methylene chloride (50/50) gradient. The appropriate fractions are pooled and concentrated to provide crude product. The crude desired product is dissolved in chloroform (3 ml) and passed over a silica gel column (27×4.5 cm, 40–63μ). The column is eluted with ethyl acetate (2 l), methanol/ethyl acetate (10/90, 1 l) and methanol/ethyl acetate (20%, 1). The appropriate fractions are pooled and concentrated to give the title compound, mp=143°–144°; NMR (CDCl$_3$, 300 MHz) 7.65, 7.55, 7.28, 4.72, 4.23, 4.15, 3.83, 3.50–3.37, 2.60 and 1.40 δ; CMR (CDCl$_3$, 75.47 MHz) 6.37, 13.64, 14.81, 38.60, 51.99, 71.04, 109.24, 109.55, 115.06, 131.89, 132.54, 142.41, 152.11, and 154.44 δ; IR (mineral oil mull) 1737, 1499 and 1411 cm$^{-1}$; MS (m/e) 385, 257, 214, 186 and 159; exact mass calcd for $C_{14}H_{16}IN_3O_2$ = 385.0289; found 385.0300.

EXAMPLE 70

(±)-3-(5'-1-Ethyl-2-methylbenzimidazolyl)-5-(azidomethyl)oxazolidin-2-one (XXXIX)

A mixture of (±)-3-(5'-1-ethyl-2-methylbenzimidazolyl)-5-(iodomethyl) oxazolidin-2-one (XXXVIII, EXAMPLE 69, 0.531 g) and sodium azide (0.618 g) are stirred in acetone/water (2/1, 30 ml) at reflux under a nitrogen overnight. After this time the mixture is poured into ethyl acetate and the layers are separated. The aqueous layer is then extracted with ethyl acetate (2×). All organic layers are combined, dried over magnesium sulfate and concentrated under reduced pressure to give an oil. A small amount of the crude product (oil) is purified on a silica preparative plate (20 cm×20 cm, 1000μ). The plate is eluted in methanol/ethyl acetate (10/90, 5×) to give the title compound as an oil; NMR (CDCl$_3$, 300 MHz) 7.70, 7.53, 7.30, 4.80, 4.15, 3.89, 3.70, 3.60, 2.61 and 3.40 δ; CMR (CDCl$_3$, 75.47 MHz) 13.62, 14.78, 38.62, 48.42, 53.05, 70.60, 109.29, 114.99, 132.1, 132.72, 142.3, 152.8, and 154.9 δ; MS (m/e) 300, 272, 227, 212, 200, 186, 172, 160, 159, 145, 131, 117, 104, 90 and 77; exact mass calcd for $C_{14}H_{16}N_6O_2$–300.1335, found: 300.1333.

EXAMPLE 71

(±)-3-(5'-1-Ethyl-2-methylbenzimidazolyl)-5-(aminomethyl)oxazolidin-2-one (XL)

A mixture of (±)-3-(5'-1-ethyl-2-methylbenzimidazolyl)-5-(azidomethyl)oxazolidin-2one (XXXIX, EXAMPLE 70, 0.190 g) and palladium on carbon (10%, 0.065 g) is stirred in ethyl acetate (70 ml) for 15.5 hrs under 1 atm (balloon) hydrogen. The mixture is then filtered and the filtrate concentrated to give the crude product as a solid in an oil. The crude sample is placed on a silica gel column (5 cm×0.5 cm, 40.63 μ) and eluted with ethyl acetate followed by methanol/ethyl acetate mixtures (1/9 10 ml, ⅓ 20 ml, 1/1 20 ml. The ⅓ and 1/1 methanol/ethyl acetate fractions are combined and concentrated to give the title compound as a foamy solid. NMR (CDCl$_3$, 300 MHz) 7.64, 7.55, 7.24, 4.70, 4.10, 3.87, 3.12, 3.01, 2.57 and 1.36 δ; CMR (CDCl$_3$, 75.47 MHz) 13.60, 14.77, 38.46, 44.80, 48.61, 73.57, 109.06, 109.17, 114.63, 131.64, 132.86, 142.52, 152.05 and 155.09 δ.

EXAMPLE 72

(±)-3-(5'-1-Ethyl-2-methylbenzimidazolyl)-5-(acetamidomethyl)oxazolidin-2-one (XLI/XLIII)

A mixture of (±)-3-(5'-1-Ethyl-2-methylbenzimidazolyl)-5-(aminomethyl)oxazolidin-2-one (XL, EXAMPLE 71, 0.100 g) in pyridine (2 ml) and acetic anhydride (1 ml) is stirred under nitrogen for 2 hrs. The mixture is then concentrated under reduced pressure to give the title compound, no further purification is necessary by analysis, mp 217°–218°, NMR (CDCl$_3$/DMF-d$_7$, 300 MHz) 7.74, 7.52, 4.80, 4.27, 3.93, 3.58, 2.61 and 1.38 δ; CMR (DMF-d$_7$, 75.47 MHz) 13.06, 14.67, 22.2, 38.65, 42.2, 72.01, 101.7, 109.34, 109.96, 114.57, 132.5, 134.2, 143.3, 153.5, 155.7 and 171.7 δ.

EXAMPLE 73

(±)-3-(5'-1-Propylbenzimidazolyl)-5-(aminomethyl)oxazolidin-2-one (XL)

Following the general procedure of EXAMPLES 67–71 and making non-critical variations but starting with 1-propyl-5-aminobenzimidazole hydrochloride (XXXV), the title compound is obtained.

EXAMPLE 74

(±) -3-(5'-1-Carbo-t-butyloxy-2-methylbenzimidazolyl)-5-(aminomethyl)oxazolidin-2-one (XL)

Following the general procedure of EXAMPLES 57, 58 and 67-71 and making non-critical variations but starting with 2-methyl-5-nitrobenzimidazole (XXXIII), the title compound is obtained.

EXAMPLE 75

(±) -3-(5'-1-Carbo-t--butyloxybenzimidazolyl)-5-(aminomethyl)oxazolidin-2-one (XL)

Following the general procedure of EXAMPLE 74 and making non-critical variations but starting with 5-nitrobenzimidazole (XXXIII), the title compound is obtained.

EXAMPLE 76

3-(5'-Indazolyl)-5β-(aminomethyl)oxazolidin-2-one (XXIX)

(±)-3-(5'-Indazolyl)-5-(aminomethyl)oxazolidin-2-one (XXIX, EXAMPLE 63) is stirred with (+) or (−) tartaric acid in methylene chloride and then permitted to stand while the product crystallizes out. The crystalline product is obtained by filtration and treated with triethylamine or sodium bicarbonate to obtain the free amine which is obtained by extraction with methylene chloride. The methylene chloride extract is concentrated to give the title compound.

EXAMPLES 77-81

Following the general procedure of EXAMPLE 76 and making non-critical variations but starting with the racemic mixtures of EXAMPLES 63, 71, 73, 74 and 75, the compounds of EXAMPLES 77-81 are obtained:
77   3-[5'-(1-n-Propylindazolyl)]-5β-(aminomethyl)oxazolidin-2-one (XXIX'),
78   3-(5'-1-Ethyl-2-methylbenzimidazolyl)-5β-(aminomethyl)oxazolidin-2-one (XL),
79   3-(5'-1-Propylbenzimidazolyl)-5β-(aminomethyl)oxazolidin-2-one (XL),
80   3-(5'-1-Carbo-t-butyloxy-2-methylbenzimidazolyl)-5β-(aminomethyl)oxazolidin-2-one (XL) and
81   3-(5'-1-Carbo-t-butyloxybenzimidazolyl)-5β-(aminomethyl)oxazolidin-2-one (XL).

EXAMPLE 82

3-[5'-(1-Acetylindazolyl)]-5β-(acetamidomethyl)oxazolidin-2-one (XXX)

3-(5'-Indazolyl)-5β-(acetamidonmethyl)oxazolidin-2-one (XXXI)

Following the general procedure of EXAMPLE 64 and making non-critical variations but starting with the optically active 3-(5'-indazolyl)-5β-(aminomethyl)oxazolidin-2-one (XXIX, EXAMPLE 76) the title compounds are obtained.

EXAMPLE 83

3-[5'-(1-Ethylindazolyl)]-5β-(acetamidomethyl)oxazolidin-2-one (XXXIII)

Following the general procedure of EXAMPLE 65 and making non-critical variations but starting with the optically active 3-(5'-indazolyl)-5β-(acetamidomethyl)oxazolidin-2-one (XXXI, EXAMPLE 82) the title compound is obtained.

EXAMPLE 84

3-[5'-(1-n-Propylidazolyl)]-5β-(acetamidomethyl)oxazolidin-2-one (XXX')

Following the general procedure of EXAMPLE 66 and making non-critical variations but starting with the optically active 3-[5'-(1-n-propylindazolyl)]-5β-(aminomethyl)oxazolidin-2-one (XXIX', EXAMPLE 77) the title compound is obtained.

EXAMPLE 85

3-(5'-1-Ethyl-2-methylbenzimidazolyl)-5β-(acetamidomethyl)oxazolidin-2-one (XLI/XLIII)

Following the general procedure of EXAMPLE 72 and making non-critical variations but starting with the optically active 3-(5'-1-ethyl-2-methylbenzimidazolyl)-5β-(aminomethyl)oxazolidin-2-one (XL, EXAMPLE 78) the title compound is obtained.

EXAMPLE 86

3-(5'-1-Propylbenzimidazol)-5β-(acetamidomethyl)oxazolidin-2-one (XLI/XLIII)

Following the general procedure of EXAMPLE 72 and making non-critical variations but starting with the optically active 3-(5'-1-propylbenzimidazolyl)-5β-(aminomethyl)oxazolidin-2-one (XL, EXAMPLE 79) the title compound is obtained.

EXAMPLE 87

3-(5'-1-Carbo-t-butyloxy-2-methylbenzimidazolyl)-5β-(acetamidomethyl)oxazolidin-2-one (XLI)

Following the general procedure of EXAMPLE 72 and making non-critical variations but starting with the optically active 3-(5'-1-carbo-t-butyloxy-2-methylbenzimidazolyl)-5β-(aminomethyl)oxazolidin-2-one (XL, EXAMPLE 80), the title compound is obtained.

EXAMPLE 88

3-(5'-2-Methylbenzimidazolyl)-5β-(acetamidomethyl)oxazolidin-2-one (XLII)

3-(5'-1-Carbo-t-butyloxy-2-methylbenzimidazolyl)-5β-(acetamidomethyl)oxazolidin-2-one (XLI, EXAMPLE 87) is contacted with trifluoroacetic acid as is known to those skilled in the art to remove the carbo-t-butyloxy protecting group. Upon workup the title compound is obtained.

EXAMPLE 89

3-(5'-1-Acetyl-2-methylbenzimidazolyl)-5β-(acetamidomethyl)oxazolidin-2-one (XLIII)

Following the general procedure of EXAMPLE 64 and making non-critical variations but starting with 3-(5'-2-methylbenzimidazolyl)-5β-(acetamidomethyl)oxazolidin-2-one (XLII,EXAMPLE 88) the title compound is obtained.

EXAMPLE 90

3-(5'-1-Formylbenzimidazolyl)-5β-(acetamidomethyl)oxazolidin-2-one (XLIII)

Following the general procedure of EXAMPLES 87, 88 and 89 but starting with 3-(4'-1-carbo-t-butyloxybenzimidazolyl)-5β-(aminomethyl)oxazolidin-2-one (XL, EXAMPLE 81) and using formic acid and acetic anhydride as the acylating agent, the title compound is obtained.

EXAMPLES 91–94

Following the general procedure of EXAMPLE 76 and making non-critical variations but starting with the racemic mixtures of EXAMPLES 7, 15, 31 and 45 the compounds of EXAMPLES 91–94 are obtained:
91  3-(5'-1-Acetylindolinyl)-5β-(aminomethyl)oxazolidin-2-one (VIII),
92  3-(5'-1-Carbo-t-butyloxyindolinyl)-5β-(aminomethyl)oxazolidin-2-one (VIII),
93  3-(6'-1-Carbo-t-butyloxyindolinyl)-5β-(aminomethyl)oxazolidin-2-one(VIII),
94  3-(b 5'-indanyl)-5β-(aminomethyl)oxazolidin-2-one (XXA).

EXAMPLE 95

3-(5'-1-Acetylindolinyl)-5β-(acetamidomethyl)oxazolidin-2-one (IX)

Following the general procedure of Example 8 and making non-critical variations but starting with 3-(5'-1-acetylindolinyl)-5β-(aminomethyl)oxazolidin-2-one (VIII, EXAMPLE 91), the title compound is obtained.

EXAMPLE 96

3-(5'-1-Carbo-t-butyloxyindolinyl)-5β-(acetamidomethyl)oxazolidin-2-one (IX)

Following the general procedure of EXAMPLE 16 and making non-critical variations but starting with 3-(5'-1-carbo-t-butyloxyindolinyl)-5β-(aminomethyl)oxazolidin-2-one (VIII, EXAMPLE 92), the title compound is obtained.

EXAMPLE 97

3-(5'-Indolinyl)-5β-(acetamidomethyl)oxazolidin-2-one (X)

Following the general procedure of EXAMPLE 17 and making non-critical variations but starting with 3-(5'-1-carbo-t-butyloxyindolinyl)-5β-(acetamidomethyl-oxazolidin-2-one (IX, EXAMPLE 96), the title compound is obtained.

EXAMPLE 98

3-(5'-1-Isobutyrlindolinyl)-5β-(acetamidomethyl)oxazolidin-2-one (XI)

Following the general procedure of EXAMPLE 18 and making non-critical variations but starting with 3-(5'-indolinyl)-5β-(acetamidomethyl)oxazolidin-2-one (X, EXAMPLE 97), the title compound is obtained.

EXAMPLE 99

3-(6'-1-Carbo-t-butyloxyindolinyl)-5β-(acetamidomethyl)oxazolidin-2-one (IX)

Following the general procedure of EXAMPLE 32 and making non-critical variations but starting with 3-(6'-1-Carbo-t-butyloxyindolinyl)-5β-(aminomethyl)oxazolidin-2-one (VIII, EXAMPLE 93), the title compound is obtained.

EXAMPLE 100

3-(6'-Indolinyl)-5β-(acetamidomethyl)oxazolidin-2-one (X)

Following the general procedure of EXAMPLE 33 and making non-critical variations but starting with 3-(6'-1-Carbo-t-butyloxyindolinyl)-5β-(acetamidomethyl)oxazolidin-2-one (IX, EXAMPLE 99), the title compound is obtained.

EXAMPLE 101

3-(5'-1-Allylindolinyl)-5β-(acetamidomethyl)oxazolidin-2-one (XI)

Following the general procedure of EXAMPLE 18 and making non-critical variations but starting with 3-(5'-indolinyl)-5β-(acetamidomethyl)oxazolidin-2-one (X, EXAMPLE 97) and using allyl bromide, the title compound is obtained.

EXAMPLE 102

(±)-3-(6'-1-Allylindolinyl)-5β-(acetamidomethyl)oxazolidin-2-one (XI)

Following the general procedure of EXAMPLE 18 and making non-critical variations but starting with 3-(6'-indolinyl)-5β-(acetamidomethyl)oxazolidin-2-one (X, EXAMPLE 100) and using allyl bromide, the title compound is obtained.

EXAMPLES 103–107

Following the general procedure of EXAMPLES 46, 47, 48, 49 and 51 and making non-critical variations but starting with 3-(5'-indanyl)-5β-(aminomethyl)oxazolidin-2-one (XXA, EXAMPLE 94), the compounds of EXAMPLES 103–107 are obtained:
103  3-(5'-Indanyl)-5β-(acetamidomethyl)oxazolidin-2-one (XXIA),
104  3-(5'-Indanyl)-5β-(butyramidomethyl)oxazolidin-2-one (XXIA),
105  3-(5'-Indanyl)-5β-(cyclopropylcarboxamidomethyl)oxazolidin-2-one (XXIA),
106  3-(5'-Indanyl)-5β-(formylamidomethyl)oxazolidin-2-one (XXIA),
107  3-(5'-Indanyl)-5β-(methoxycarboxamidomethyl)oxazolidin-2-one (XXIA).

EXAMPLE 108

3-(1'-Oxo-5'-indanyl)-5β-(acetamidomethyl)oxazolidin-2-one (XXIB)

Following the general procedure of EXAMPLE 52 and making non-critical variations but starting with 3-(5'-indanyl)-5β-(acetamidomethyl)oxazolidin-2-one (XXIA, EXAMPLE 103), the title compound is obtained.

EXAMPLE 109

3-(1-Oximino-5'-indanyl)-5β-(acetamidomethyl)oxazolidinone (XXIE)

Following the general procedure of EXAMPLE 53 and making non-critical variations but starting with 3-(1'-oxo-5'-indanyl)-5β-(acetamidomethyl)oxazolidin-2-one (XXIB, EXAMPLE 108), the title compound is obtained.

EXAMPLE 110

3-(1'-Hydroxy-5'-indanyl)-5β-(acetamidomethyl)oxazolidin-2-one (XXIC)

Following the general procedure of EXAMPLE 54 and making non-critical variations but starting with 3-(1'-oxo-5'-indanyl)-5β-(acetamidomethyl)oxazolidin-2-one (XXIB, EXAMPLE 108), the title compound is obtained.

EXAMPLE 111

3-(6'-Tetralinyl)-5β-(acetamidomethyl)oxazolidin-2-one (XXIA)

Following the general procedure of EXAMPLES 41–44 and 94, and making non-critical variations but starting with 6-aminotetralin, the title compound is obtained.

EXAMPLE 112

3-(1'-Oxo-6'-tetralinyl)-5β-(acetamidomethyl)oxazolidin-2-one (XXIB)

Following the general procedure of EXAMPLE 52 and making non-critical variations, but starting with 3-(6'-tetralinyl)-5β-(acetamidomethyl)oxazolidin-2-one (XXIA, EXAMPLE 111), the title compound is obtained.

EXAMPLES 113–118

Following the general procedure of EXAMPLES 19–24 and making non-critical variations but starting with 3-(5'-indolinyl)-5β-(acetamidomethyl)oxazolidin-2-one (X, EXAMPLE 97), the compounds of EXAMPLES 113–118 are obtained:

113  3-(5'-1-Propanoylindolinyl)-5β-(acetamidomethyl)oxazolidin-2-one (XI),
114  3-(5'-1-Cyclopentylcarbonylidolinyl)-5β-(acetamidomethyl)oxazolidin-2-one (XI),
115  3-(5'-1-Formylindolinyl)-5β-(acetamidomethyl)oxazolidin-2-one (XI),
116  3-(5'-1-Chloroacetylindolinyl)-5β-(acetamidomethyl)oxazolidin-2-one (XI),
117  3-(5'-1-Dichloroacetylindolinyl)-5β-(acetamidomethyl)oxazolidin-2-one (XI) and
118  3-(5'-1-Phenylacetylindolinyl)-5β-(acetamidomethyl)oxazolidin-2-one (XI)

EXAMPLE 119–128

Following the general procedure of
1. . EXAMPLES 1–7 for production of the protected aminomethyl (VIII),
2. EXAMPLES 16–18 for production of the optically active (XI),
3. For the cases with hydroxyacetyl and propyl, in addition, follow the procedure of EXAMPLES 2 or 10 (reduction of nitro to amino is the same conditions as for reduction of allyl to propyl or cleavage of a benzyl group) and making non-critical variations but starting with appropriately substituted nitroindoline (I), the compounds of EXAMPLES 119–128 are obtained:

119 (±)-3-(5'-1-Benzoylindolinyl)-5β-(acetamidomethyl)oxazolidin-2-one (XI), mp 215°–216°;
120 (±)-3-(5'-1-Methylsulfonylindolinyl)-5β-(acetamidomethyl)oxazolidin-2-one (XI), mp 177°–178°;
121 (±)-3-(5'-1-Methylindolinyl)-5β-(acetamidomethyl)-oxazolidin-2-one (XI), NMR (methanol-$d_4$) 7.36, 7.08, 6.49, 4.70, 4.02, 3.71, 3.51, 3.25, 2.89, 2.71 and 1.96 δ;
(±)-3-(5'-1-Hydroxyacetylindolinyl)-5β-(acetamidomethyl)oxazolidin-2-one (XI), mp 207°–209°;
123 (±)-3-(5'-1-Benzyloxyacetylindolinyl)-5β-(acetamdiomethyl)oxaziolidin-2-one (XI), mp 181°–183°;
124 (±)-3-(5'-1-p-Chlorobenzoylindolinyl)-5β-(acetamidomethyl)oxazolidin-2-one (XI), mp 225°–227°;
125 (±)-3-(5'-1-Allylindolinyl)-5β-(acetamidomethyl)oxazolidin-2-one (XI), mp 152°–153°;
126 (±)-3-(5'-1-Propylindolinyl)-5β-(acetamidomethyl)oxazolidin-2-one (XI), NMR (CDCl$_3$, 300 MHz) 7.21, 7.17, 7.00, 6.37, 4.70, 3.99, 3.71, 3.56, 3.33, 2.95, 1.99, 1.60, and 0.97 δ; CMR (CDCl$_3$, 75.47 MHz): 11.56, 20.37, 22.83, 28.41, 41.86, 48.80, 51.07, 53.02, 71.80, 106.29, 117.48, 119.47, 127.80, 130.85, 150.34, 155.33, and 171.259 δ; IR (mineral oil mull) 3418, 1732, 1661, 1550, 1504, 1473, 1228, and 1084 cm$^{-1}$; MS (m/e): 317, 288, 244, 185, 173, 159, and 130; exact mass calculated for $C_{17}H_{23}N_3O_3 = 317.1739$, found 317.1736.
127 (±)-3-(5'-1-Methoxyacetylindolinyl)-5β-(acetamidomethyl)oxazolidin-2-one (XI), mp 209°–210°;
128 (±)-3-(5'-1-Hexanoylindolinyl)-5β-(acetamidomethyl)oxazolidin-2-one (XI), mp 194°–195°.

EXAMPLE 129

(±)-3-(1'-Oxo-2'-α-methyl-5'-indanyl)-5β-(acetamidomethyl)oxazolidin-2-one (XXIB),
(±)-3-(1'-oxo-2'β-methyl-5'-indanyl)-5β-(acetamidomethyl)oxazolidin-2-one (XXIB) and
(±)-3-(1'-Oxo-2', 2'-dimethyl-5'-indanyl)-5β-(acetamidomethyl)oxazolidin-2-one (XXIB)

n-Butyl lithium (1.6M, 0.92 ml) is added to a solution of diisopropylamine (20 ml) in dry tetrahydrofuran (15 ml) at −78° under nitrogen, and the mixture stirred for 30 min. Solid (±)-3-(1'-oxo-5'-indanyl)-5β-(acetamidomethyl)oxazolidin-2-one (XXIB, EXAMPLE 52, 200 mg) is added at once, and the mixture is stirred for 30 min at −78°, then iodomethane (48 μl) of iodomethane is added and the mixture then allowed to stir at 0° for an additional 21 hr. The mixture is quenched with saturated aqueous ammonium chloride (10 ml), and then poured into water (30 ml), and the pH adjusted to 7. The aqueous layer is extracted with ethyl acetate (4×), and the combined organic layers are washed with saline, then dried over magnesium sulfate, and concentrated under reduced pressure to give an residual oil. The oil is purified by preparative TLC [2000 μ, 20 cm×20 cm, methanol/ethyl acetate (4/96, 4 elutions)] to give the α/β-methyl compounds, NMR (CDCl$_3$) 7.72, 7.64, 7.52, 6.59, 4.84, 4.13, 3.89, 3.69, 3.38, 2.72, 2.04 and 1.30 δ; CMR (CDCl$_3$) 16.18, 22.85, 34.85, 41.61, 41.97, 47.43, 71.95, 114.75, 116.98, 124.77, 131.82, 143.39, 153.99, 154.81, 171.14 and 207.89; δ; IR (CHCl$_3$) 3440, 1753, 1696, 1672 and 1603 cm$^{-1}$; MS (m/e) 302, 258, 243, 230, 215 and 199; exact mass calcd for $C_{16}H_{18}N_2O_4 = 302.1267$, found 302.1274 and the dimethyl compound, MS (m/e) 316, 272, 257, 244, 299, 213 and 43; exact mass calcd for $C_{17}H_{20}N_2O_4 = 316.1423$, found 316.1420.

EXAMPLE 130

(±)-3-(1'-Oxo-2'α-ethyl-5'-indanyl)-5β-(acetamidomethyl)oxazolidin-2-one (XXIB),
(±)-3-(1'-oxo-2'β-ethyl-5'-indanyl)-5β-(acetamidomethyl)oxazolidin-2-one (XXIB) and (±)-3-(1'-Oxo-2', 2'-diethyl-5'-indanyl)-5β-(acetamidomethyl)oxazolidin-b 2-one (XXIB)

Following the general procedure of EXAMPLE 129 and making noncritical variations but using ethyl iodide (72 μl), permitting the mixture to warm to 20°–25° for 18 hr, and the eluting with methanol/ethyl acetate (7/93)], the title compounds are obtained, NMR (CDCl$_3$) 7.74, 7.68, 7.51, 6.26, 4.83, 4.13, 3.87, 3.70, 3.30, 2.82, 2.64, 2.04, 1.96, 1.55 and 1.00 δ; CMR (CDCl$_3$) 75.47 MHz) 11.35, 22.98, 24.41, 32.28, 41.76, 47.51, 48.77, 71.89, 114.89, 116.98, 124.77, 132.6, 143.5, 154.1, 155.2, 171.1 and 207.5 δ; IR (CHCl$_3$) 3680, 3440, 1750, 1680 and 1600 cm$^{-1}$; MS (m/e) 316, 288, 272, 244, 229, 42, exact mass calcd for $C_{17}H_{20}N_2O_4 = 316.2423$, found 316.1412.

EXAMPLE 131

(±)-3-(1'-Oxo-2'-spirocyclopropyl-5'-indanyl)-5β-(acetamidomethyl)oxazolidin-2-one (XXIB)

Sodium hydride/mineral oil suspension is added (50%, 33 mg) to dry, distilled t-butanol (5 ml) followed by (±)-3-(1'-oxo-5'-indanyl)-5β-(acetamidomethyl)oxazolidin-2-one (XXIB, EXAMPLE 52, 100 mg). The mixture stirred at 20°–25° for 15 min. Then sodium iodide (10 mg) is added, followed by 2-chloroethyldimethylsulfonium iodide (88 mg) in small portions over a period of 1 hr, and the resulting mixture is stirred for an additional 21 hr. Then water (25 ml) is added to the mixture, and the pH adjusted to 7, and the mixture extracted with ethyl acetate (4×). The combined organic layers are washed with saline, dried over magnesium sulfate and concentrated under reduced pressure to give an oily residue. The oil is purified by preparative TLC [1000 micron, 20 cm×20 cm, methanol/ethyl acetate (5/95), 3 elutions] to give the title compound, NMR (CDCl$_3$) 7.78, 7.77, 7.51, 6.11, 4.84, 4.14, 3.89, 3.68, 3.21, 2.03, 1.45 and 1.15 δ.

EXAMPLE 132

(±)-3-(1'-Oxo-2'α-methyl-6'-tetralinyl)-5β-(acetamidomethyl)oxazolidin-2-one (XXIB),
(±)-3-(1'-oxo-2'β-methyl-6'-tetralinyl)-5-(acetamidomethyl)oxazolidin-2-one (XXIB) and
(±)-3-(1'-Oxo-2',2'-dimethyl-6'-tetralinyl)-5β-(acetamidomethyl)oxazolidin-2-one (XXIB)

Following the general procedure of EXAMPLE 129 and making non-critical variations but starting with (±)-3-(1'-Oxo-6'-tetralinyl)-5β-(acetamidomethyl)oxazolidin-2-one (XXIB, EXAMPLE 56) the α/β-methyl compounds are obtained, NMR (CDCl$_3$) 8.03, 7.44, 7.40, 6.38, 4.81, 4.08, 3.84, 3.67, 2.98, 2.57, 2.18, 2.03, 1.90 and 1.26 δ; the dimethyl compound, MS (m/e) 330, 286, 274, 258, 202 and 42; exact mass calcd for $C_{18}H_{22}N_2O_4 = 330.1580$, found 330.1577.

EXAMPLE 133

(±)-3-(1'-Oxo-2'-spirocyclopropyl-6'-tetralinyl)-5β-(acetamidomethyl)oxazolidin-2-one (XXIB)

Following the general procedure of EXAMPLE 131 and making non-critical variations but starting with (±)-3-(1'-oxo-6'-tetralinyl)-5β-(acetamidomethyl)oxazolidin-2-one (XXIB, EXAMPLE 56) the title compound is obtained, TLC (methanol/ethyl acetate; 5/95) R$_f$=0.32.

EXAMPLE 134

(±)-3-(1'-Oxo-2'α-hydroxymethyl-5'-indanyl)-5β-(acetamidomethyl)oxazolidin-2-one (XXIB) and
(±)-3-(1'-oxo-2'β-hydroxymethyl-5'-indanyl)-5β-(acetamidomethyl)oxazolidin-2-one (XXIB)

As sodium hydride/mineral oil dispersion (50%, 66 mg) is added all at once to a solution of (±)-3-(1'-oxo-5'-indanyl)-5β-(acetamidomethyl)oxaziolidin-2-one (XXIB, EXAMPLE 52, 200 mg) in dry tetrahydrofuran (5 ml) at 0° and the mixture stirred for 30 min at 0°. Then excess gaseous formaldehyde is bubbled into the solution via a needle attached to a flask where solid paraformaldehyde is heated. The reaction mixture is then allowed to warm to 20°–25° for 1 hr and then poured into water and extracted with ethyl acetate 3 times. The combined organic extracts are combined, dried over magnesium sulfate and concentrated under reduced pressure to give a solid. The solid is chromatographed on silica gel (1000μ) preparative TLC using a 20×20 cm plate, and eluting with methanol/ethyl acetate (5/95) to give the title compounds.

EXAMPLE 135

(±)-3-(1'-Oxo-2'α-hydroxymethyl-6'-tetralinyl)-5β-(acetamidomethyl)oxazolidin-2-one (XXIB) and
(±)-3-(1'-oxo-2'β-hydroxymethyl-6'-tetralinyl)-5β-(acetamidomethyl)oxazolidin-2-one (XXIB)

Following the general procedure of EXAMPLE 134 and making non-critical variations but starting with (±)-3-(1'-oxo-6'-tetralinyl)-5β-(acetamidomethyl)oxazolidin-2-one (XXIB, EXAMPLE 56) the title compounds are obtained.

EXAMPLE 136

3-(1'-Oxo-2'α-methyl-5'-indanyl)-5β-(acetamidomethyl)oxazolidin-2-one (XXIB),
3-(1'-oxo-2'β-methyl-5'-indanyl)-5β-(acetamidomethyl)oxazolidin-2-one (XXIB) and 3-(1'-Oxo-2', 2'-dimethyl-5'-indanyl)-5β-(acetamidomethyl)oxazolidin-2-one (XXIB)

Following the general procedure of EXAMPLE 129 and making non-critical variations but starting with 3-(1'-oxo-5'-indanyl)-5β-(acetamidomethyl)oxazolidin-2-one (XXIB, EXAMPLE 108) the title compounds are obtained.

EXAMPLE 137

3-(1'-Oxo-2'α-ethyl-5'-indanyl)-5β-(acetamidomethyl)oxazolidin-2-one (XXIB) and
3-(1'-oxo-2'β-ethyl-5'-indanyl)-5β-(acetamidomethyl)oxazolidin-2-one (XXIB)

Following the general procedure of EXAMPLE 130 and making non-critical variations but starting with 3-(1'-oxo-5'-indanyl)-5β-(acetamidomethyl)oxazolidin-2-one (XXIB, EXAMPLE 108) the title compounds are obtained.

EXAMPLE 138

3-(1'-Oxo-2'-spirocyclopropyl-5'-indanyl)-5β-(acetamidomethyl)oxazolidin-2-one (XXIB)

Following the general procedure of EXAMPLE 131 and making non-critical variations but starting with 3-(1'-oxo-5'-indanyl)-5β-(acetamidomethyl)oxazolidin-2-one (XXIB, EXAMPLE 108), the title compound is obtained.

EXAMPLE 139

3-(1'-Oxo-2'-α-methyl-6'-tetralinyl)-5β-(acetamidomethyl)oxazolidin-2-one (XXIB), 3-(1'-oxo-2'β-methyl-6'-tetalinyl)-5β-(acetamidomethyl)oxazolidin-2-one (XXIB) and 3-(1'-Oxo-2', 2'-dimethyl-6'-tetralinyl)-5β-(acetamidomethyl)oxazolidin-2-one (XXIB)

Following the general procedure of EXAMPLE 132 and making noncritical variations but starting with 3-(1'-oxo-6'-tetralinyl)-5β-(acetamidomethyl)oxazolidin-2-one (XXIB, EXAMPLE 122), the title compounds are obtained.

EXAMPLE 140

3-(1'-Oxo-2'-spirocyclopropyl-6'-tetralinyl)-5β-(acetamidomethyl)oxazolidin-2-one (XXIB)

Following the general procedure of EXAMPLE 133 and making noncritical variations buts starting with 3-(1'-oxo-6'-tetralinyl)-5β-(acetamidomethyl)oxazolidin-2-one (XXIB, EXAMPLE 112), the title compound is obtained.

EXAMPLE 141

3-(1'-Oxo-2'α-hydroxymethyl-5'-indanyl)-5β-(acetamidomethyl)oxazolidin-2-one (XXIB) and 3-(1'-oxo-2'β-hydroxymethyl-5'-indanyl)-5β-(acetamidomethyl)oxazolidin-2-one (XXIB)

Following the general procedure of EXAMPLE 134 and making non-critical variations but starting with 3-(1'-oxo-5'-indanyl)-5β-(acetamidomethyl)oxazolidin-2-one (XXIB, EXAMPLE 108), the title compounds are obtained.

EXAMPLE 142

3-(1'-Oxo-2'α-hydroxymethyl-6'-tetalinyl)-5β-(acetamidomethyl)oxazolidin-2-one (XXIB) and 3-(1'-oxo-2'β-hydroxymethyl-6'-tetalinyl)-5β-(acetamidomethyl)-oxazolidin-2-one (XXIB)

Following the general procedure of EXAMPLE 135 and making non-critical variations buts starting with 3-(1'-oxo-6'-tetalinyl)-5β-(acetamidomethyl)oxazolidin-2-one (XXIB, EXAMPLE 112), the title compounds are obtained.

EXAMPLE 143

(±)-3-(5'-1-(O-Acetyl(hydroxyacetyl)indolinyl))-5-(acetamidomethyl)-oxazolidin-2-one (XI)

The free hydroxy group of (±)-3-(5'-1-hydroxyacetylindolinyl)-5-(acetamidomethyl)oxazolidin-2-one (XI, EXAMPLE 122) is acylated as is known to those skilled in the art, NMR (CDCl₃, 300 MHz) 8.10, 7.58, 7.01, 6.49, 4.77, 4.01, 3.76, 3.65, 3.23, 2.23 and 2.04 δ.

EXAMPLE 144

3-(5'-1-(O-Acetyl(hydroxyacetyl)indolinyl))-5β-(acetamidomethyl)oxazolidin-2-one (XI)

Following the general procedure of EXAMPLE 143 and making noncritical variations but starting with 3-(5', 1-hydroxyacetylindolinyl)-5β-(acetamidomethyl)oxazolidin-2-one (XI, EXAMPLE 150) the title compound is obtained.

EXAMPLE 145

(±)-3-[5'-1-(2-thienylcarbonyl)indolinyl]-5-(acetamidomethyl)oxazolidin-2-one (XI)

Following the general procedure of EXAMPLE 18 and making noncritical variations but using 2-thienylcarbonyl chloride, the title compound is obtained, mp 201°–203°.

EXAMPLE 146

3-[5'-1-(2-Thienylcarbonyl)indolinyl]-5β-(acetamidomethyl)oxazolidin-2-one (XI)

Following the general procedure of EXAMPLE 18 and making noncritical variations but using 3-(5'-indolinyl)-5β-(acetamidomethyl)-oxazolidin-2-one (X, EXAMPLE 97) and 2-thienylcarbonyl chloride, the title compound is obtained.

EXAMPLES 147–156

Following the general procedure of EXAMPLES 119–128 and making non-critical variations but using the process of EXAMPLE 76 for the resolution of the optically impure mixture of (VIII) and thereafter using the optically active (VIII), the title compounds are obtained:

147 3-(5'-1-Benzoylindoliyl)-5β-(acetamidomethyl)oxazolidin-2-one (XI),
148 3-(5'-1-Methylsulfonylindolinyl)-5β-(acetamidomethyl)-oxazolidin-2-one (XI),
149 3-(5'-1-Methylindolinyl)-5β-(acetamidomethyl)oxazolidin-2-one (XI),
150 3-(5'-1-Hydroxyacetylindolinyl)-5β-(acetamidomethyl)-oxazolidin-2-one (XI),
151 3-(5'-1-Benzyloxyacetylindolinyl)-5β-(acetamidomethyl)-oxazolidin-2-one (XI),
152 3-(5'-1-p-Chlorobenzoylindolinyl)-5β-(acetamidomethyl)-oxazolidin-2-one (XI),
153 3-(5'-1-Allylindolinyl)-5β-(acetamidomethyl)oxazolidin-2-one (XI),
154 3-(5'-1-Propylindolinyl)-5β-(acetamidomethyl)oxazolidin-2-one (XI),
155 3-(5'-1-Methoxyacetylindolinyl)-5β-(acetamidomethyl)-oxazolidin-2-one (XI),
156 3-(5'-1-Hexanoylindolinyl)-5β-(acetamidomethyl)oxazolidin-2-one (XI).

CHART A

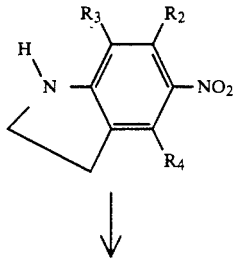

(I)

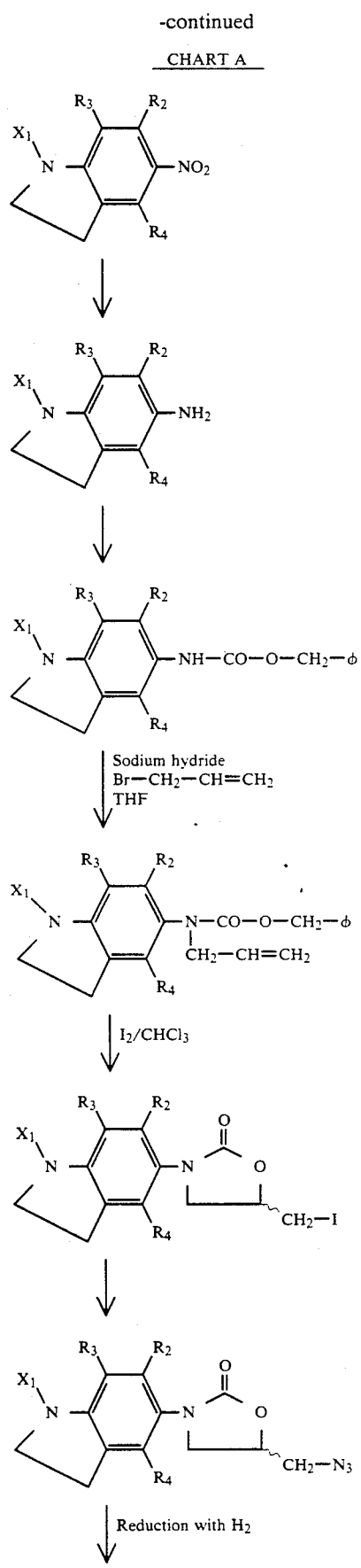
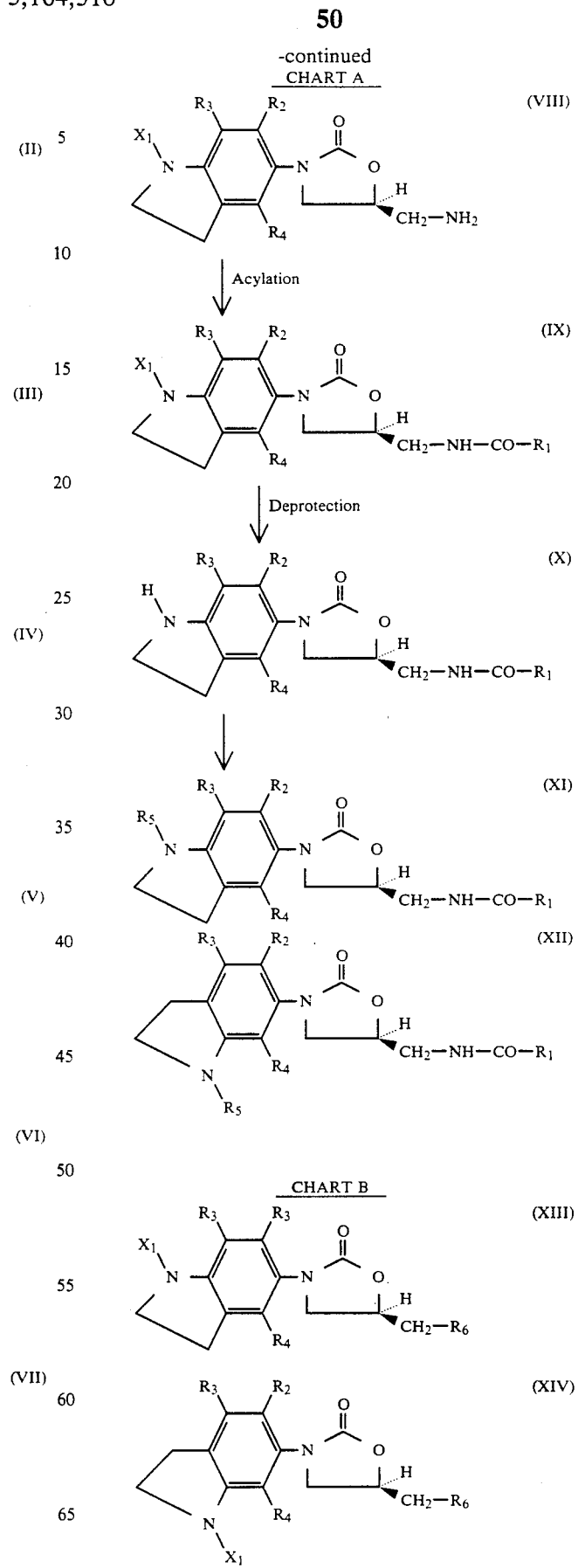

CHART C

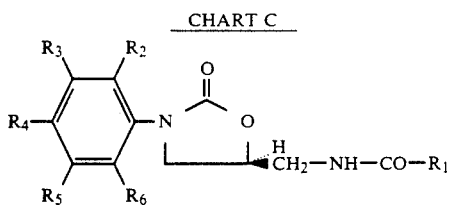
(XXI)

Fused cycloalkylphenyl-oxazolidinones (XXIA) where
one of $R_2$ and $R_4$ is —H and
$R_2$ or $R_3$ end is: $R_3$ or $R_4$ end is:
—$CH_2$—$CH_2$—$CH_2$— and
—$CH_2$—$CH_2$—$CH_2$—$CH_2$— which is represented by
—$(CH_2)_{n2}$— where $n_2$ is 3 or 4.

Fused alkanonephenyl-oxazolidinones (XXIB) where
one of $R_2$ and $R_4$ is —H and
$R_2$ or $R_3$ end is: $R_3$ or $R_4$ end is:
—$CH_2$—$CHR_{10}$—CO—,
—$CH_2$—$CH_2$—$CHR_{10}$—CO—,
—$CH_2$—$CHR_{10}$—CO—$CH_2$—,
—$CHR_{10}$—CO—$CH_2$—,
—$CHR_{10}$—CO—$CH_2$—$CH_2$—,
—$CH_2$—CO—$CHR_{10}$—,
—$CH_2$—$CH_2$—CO—$CHR_{10}$—,
—$CH_2$—CO—$CHR_{10}$—$CH_2$—,
—CO—$CHR_{10}$—$CH_2$— and
—CO—$CHR_{10}$—$CH_2$—$CH_2$— which is represented by
—$(CH_2)_{n3}$—$(CR_{10\text{-}1}R_{10\text{-}2})_{n7}$—CO—$(CHR_{10\text{-}3}R_{10\text{-}4})_{n8}$—$(CH_2)_{n4}$— where $n_3$ and $n_4$ are 0–3, $n_7$ and $n_8$ are 0 or 1, $R_{10\text{-}1}$ and $R_{10\text{-}2}$ are the same or different and are —H, $C_1$-$C_3$ alkyl and where $R_{10\text{-}1}$ and $R_{10\text{-}2}$ taken together with the carbon atom to which they are attached form spirocyclopropyl, $R_{10\text{-}3}$ and $R_{10\text{-}4}$ are the same or different and are —H, $C_1$-$C_3$ alkyl and where $R_{10\text{-}3}$ and $R_{10\text{-}4}$ taken together with the carbon atom to which they are attached form spirocyclopropyl, with the provisos that (1) $n_7+n_8=0$ or 1, (2) $n_3+n_4+n_7+n_8=2$ or 3 and (3) when $n_4$ is 0, either (a) $n_8=1$ or (b) $n_7=1$ and one of $R_{10\text{-}1}$ or $R_{10\text{-}2}$ is not —H;

Fused hydroxycycloalkylphenyl-oxazolidinones (XXIC)
where one of $R_2$ and $R_4$ is —H and
$R_2$ or $R_3$ end is: $R_3$ or $R_4$ end is:
—CHOH—$CH_2$—$CH_2$ —,
—$CH_2$—CHOH—$CH_2$—,
—$CH_2$—$CH_2$—CHOH—,
—CHOH—$CH_2$—$CH_2$—$CH_2$—,
—$CH_2$—CHOH—$CH_2$—$CH_2$—,
—$CH_2$—$CH_2$—CHOH—$CH_2$— and
—$CH_2$—$CH_2$—$CH_2$—CHOH— which is represented by
—$(CH_2)_{n3}$—CHOH—$(CH_2)_{n4}$— where $n_3$ and $n_4$ are 0–3 with the proviso that $n_3+n_4=2$ or 3.

Fused cycloalkenylphenyl-oxazolidinones (XXID)
where one of $R_2$ and $R_4$ is —H and
$R_2$ or $R_3$ end is: $R_3$ or $R_4$ end is:
—CH=CH—$CH_2$—,
—$CH_2$—CH=CH—,
—CH=CH—$CH_2$—$CH_2$—,
—$CH_2$—CH=CH—$CH_2$— and
—$CH_2$—$CH_2$—CH=CH— which is reprented by
—$(CH_2)_{n5}$—CH=CH—$(CH_2)_{n6}$— where $n_5$ and $n_6$ are 0–2 with the proviso that $n_5+n_6=1$ or 2.

Fused oximinocycloalkylphenyl-oxazolidinones (XXIE)
where one of $R_2$ and $R_4$ is —H and
$R_2$ or $R_3$ end is: $R_3$ or $R_4$ end is:
—C(=N—$OR_7$)—$CHR_{10}$—$CH_2$—,
—$CHR_{10}$—C(=N—$OR_7$)—$CH_2$—,
—$CH_2$—C(=N—$OR_7$)—$CHR_{10}$—,
—$CH_2$—$CHR_{10}$—C(=N—$OR_7$)—,
—C(=N—$OR_7$)—$CHR_{10}$—$CH_2$—$CH_213$,
—$CHR_{10}$—C(=N—$OR_7$)—$CH_2$—$CH_213$,
—$CH_2$—C(=N—$OR_7$)—$CHR_{10}$—$CH_2$—,
—$CH_2$—$CH_2$—$CHR_{10}$—C(=N—$OR_7$)— which is represented by —$(CH_2)_{n3}$—$(CHR_{10})_{n7}$—C(=N—$OR_7$)—$(CHR_{10})_{n8}$—$(CH_2)_{n4}$— where $n_3$, $n_4$, $n_7$ and $n_8$ are as defined above, with the provisos that (1) $n_7+n_8=0$ or 1, (2) $n_3+n_4+n_7+n_8=2$ or 3 and (3) when $n_3$ is 0, either (a) $n_7=1$ or (b) $n_8 \geq 1$ and one of $R_{10\text{-}1}$ or $R_{10\text{-}2}$ is not —H;

Fused iminocycloalkylphenyl-oxazolidinones (XXIF)
where one of $R_2$ and $R_4$ is —H and
$R_2$ or $R_3$ end is: $R_3$ or $R_4$ end is:
—C(=N—$R_8$)—$CH_2$—$CH_2$—,
—$CH_2$—C(=N—$R_8$)—$CH_2$—,
—$CH_2$—$CH_2$—C(=N—$R_8$)—,
—C(=N—$R_8$)—$CH_2$—$CH_2$—$CH_2$—,
—$CH_2$—C(=N—$R_8$)—$CH_2$—$CH_2$—,
—$CH_2$—$CH_213$ C(=N—$R_8$)—$CH_2$—,
—$CH_2$—$CH_2$—$CH_2$—C(=N—$R_8$)— which is represented by —$(CH_2)_{n3}$—C(=N—$R_8$)—$(CH_2)_{n4}$— where $n_3$ and $n_4$ are as defined above.

Fused aminocycloalkylphenyl-oxazolidinones (XXIG)
where one of $R_2$ and $R_4$ is —H and
$R_2$ or $R_3$ end is: $R_3$ or $R_4$ end is:
—C($NR_{11}R_{12}$)—$CH_2$—$CH_2$—,
—$CH_2$—C($NR_{11}R_{12}$)—$CH_213$,
—$CH_2$—$CH_2$—C($NR_{11}R_{12}$)—,
—C($NR_{11}R_{12}$)—$CH_2$—$CH_2$—$CH_2$—,
—$CH_2$—C($NR_{11}R_{12}$)—$CH_2$—$CH_2$—,
—$CH_2$—$CH_213$ C($NR_{11}R_{12}$)—$CH_2$—,
—$CH_2$—$CH_2$—$CH_2$—C($NR_{11}R_{12}$)— which is represented by —$(CH_2)_{n3}$—CH($NR_{11}R_{12}$)—$(CH_2)_{n4}$— where $n_3$ and $n_4$ are as defined above.

Fused enaminocycloalkylphenyl-oxazolidinones (XXIH) where
one of $R_2$ and $R_4$ is —H and
$R_2$ or $R_3$ end is: $R_3$ or $R_4$ end is:
—C($NR_{13}R_{14}$)=CH—$CH_2$—
—CH=C($NR_{13}R_{14}$)—$CH_2$—
—$CH_2$—C($NR_{13}R_{14}$)=CH—
—$CH_2$—CH=C($NR_{13}R_{14}$)—
—C($NR_{13}R_{14}$)=CH—$CH_2$—$CH_2$—
—CH=C($NR_{13}R_{14}$)—$CH_2$—$CH_2$—
—$CH_2$—C($NR_{13}R_{14}$)=CH—$CH_2$—
—$CH_2$—CH=C($NR_{13}R_{14}$)—$CH_2$—
—$CH_2$—$CH_2$—C($NR_{13}R_{14}$)=CH—
—$CH_2$—$CH_2$—CH=C($NR_{13}R_{14}$)— which is represented by —$(CH_2)_{n3}$—CH=C($NR_{13}R_{14}$)—$(CH_2)_{n4}$— where $n_3$ and $n_4$ are as defined above.

CHART D
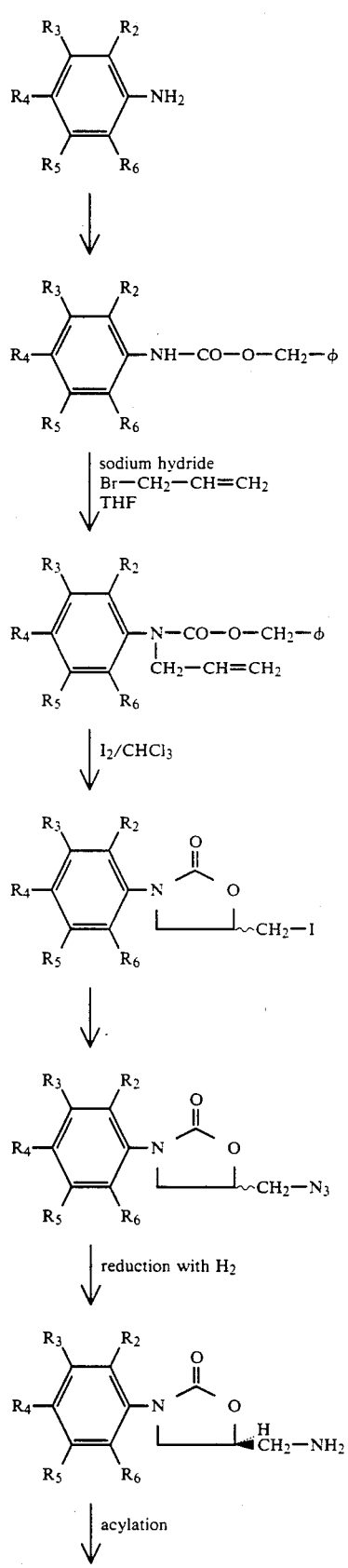
CHART D (continued)
CHART E
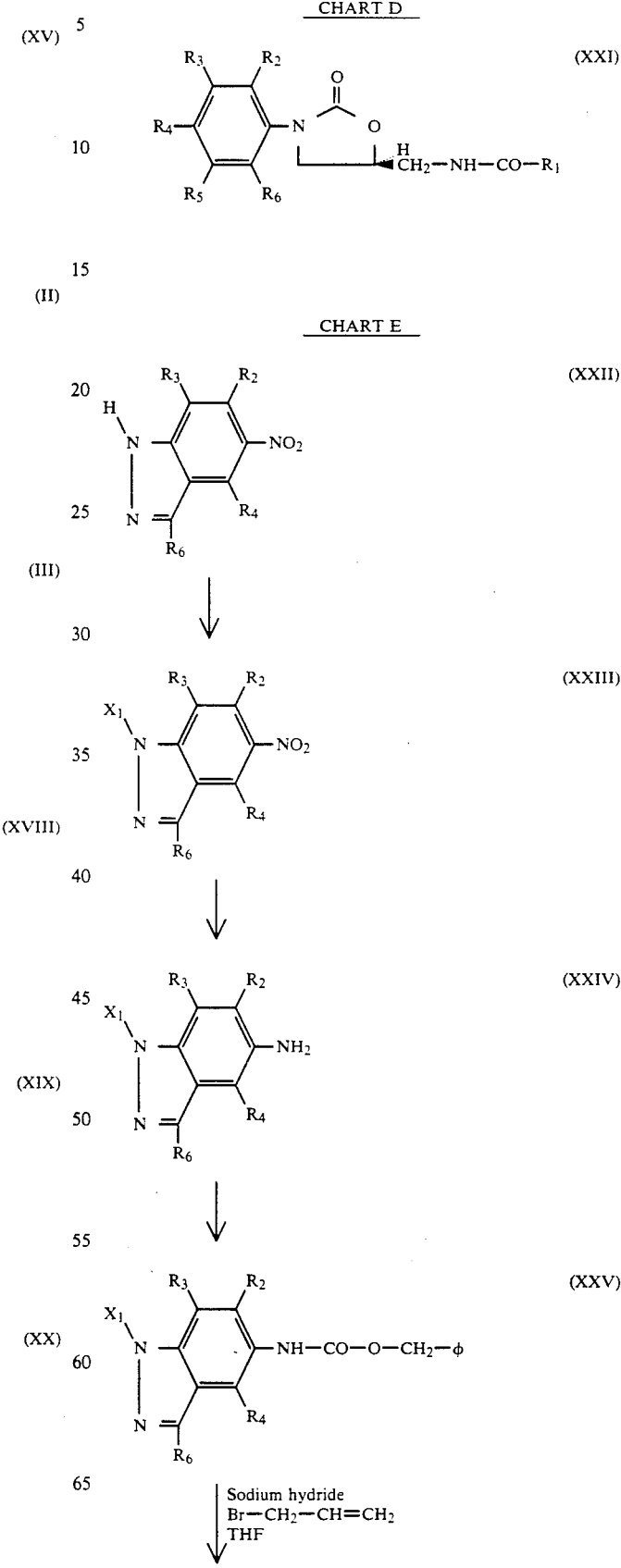

-continued
CHART E
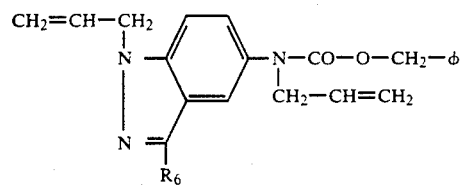
(XXVI')
↓ I₂/CHCl₃
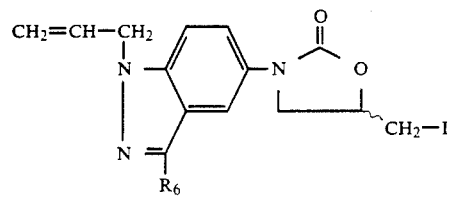
(XXVII')
↓ I₂/CHCl₃
↓ NaN₃
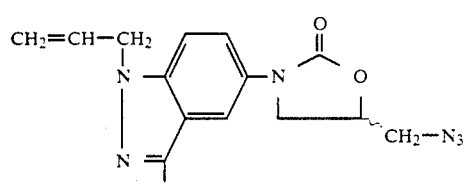
(XXVIII')
↓ Reduction with H₂
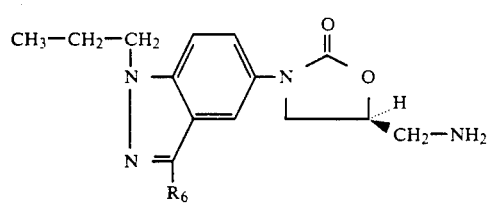
(XXIX')
↓ Acylation
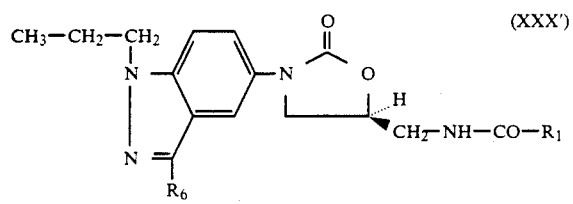
(XXX')
(XXV)
↓ Sodium hydride
  Br—CH₂—CH=CH₂
  THF
-continued
CHART E
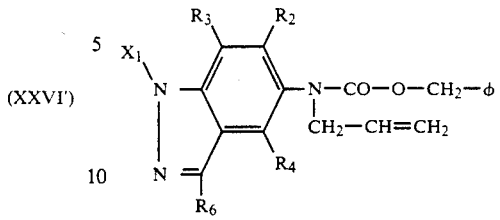
(XXVI)
↓ I₂/CHCl₃
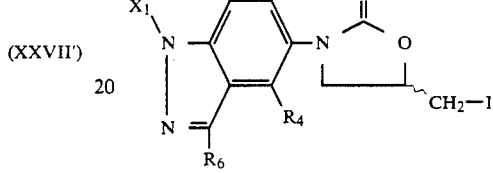
(XXVII)
↓ NaN₃
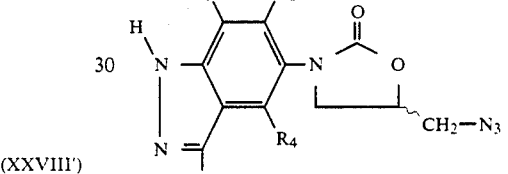
(XXVIII)
↓ Reduction with H₂
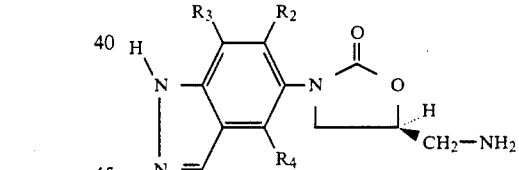
(XXIX)
↓ Acylation
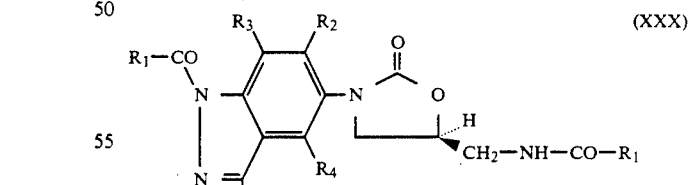
(XXX)
+
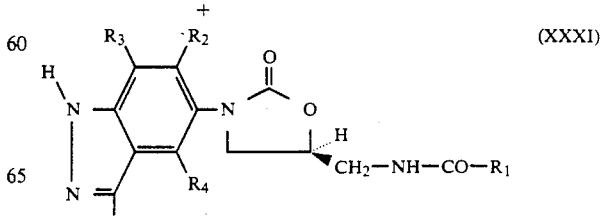
(XXXI)

-continued
CHART E
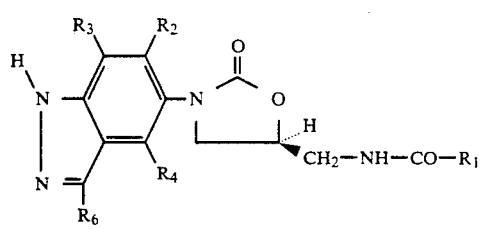
(XXXI)
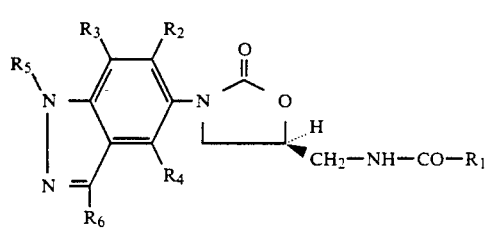
(XXXII)
CHART F
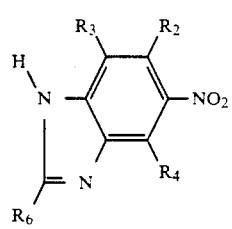
(XXXIII)
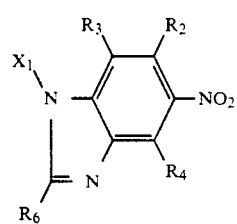
(XXIV)
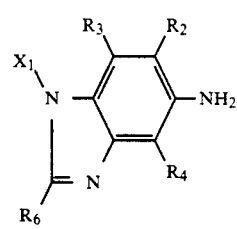
(XXXV)
-continued
CHART F
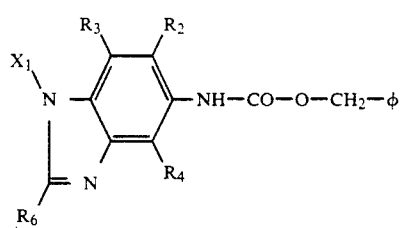
(XXXVI)
| Sodium hydride
| Br—CH₂—CH=CH₂
↓ THF
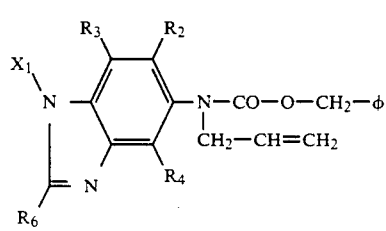
(XXXVII)
↓ I₂/CHCl₃
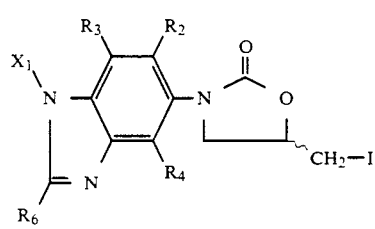
(XXXVIII)
↓ NaN₃
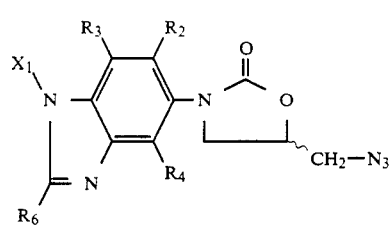
(XXXIX)
↓ Reduction with H₂
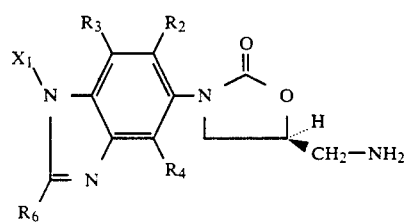
↓ Acylation

-continued
CHART F
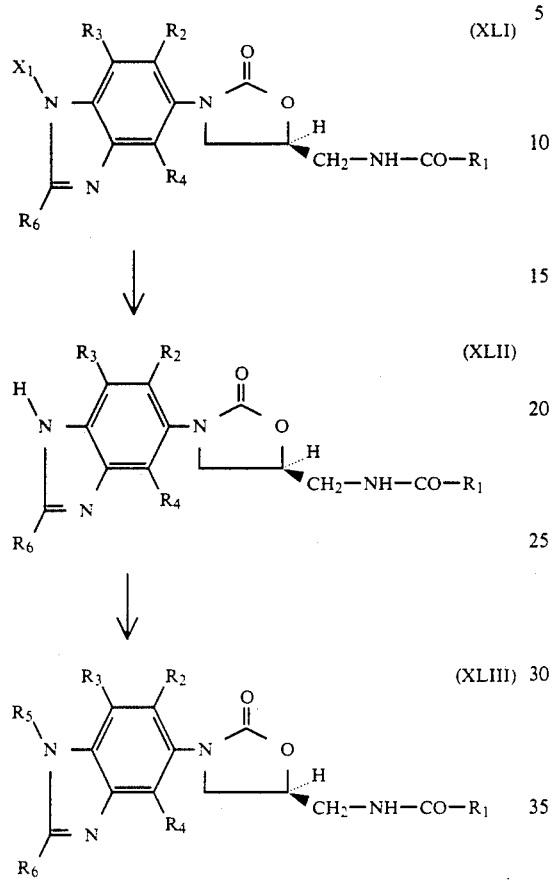
CHART G
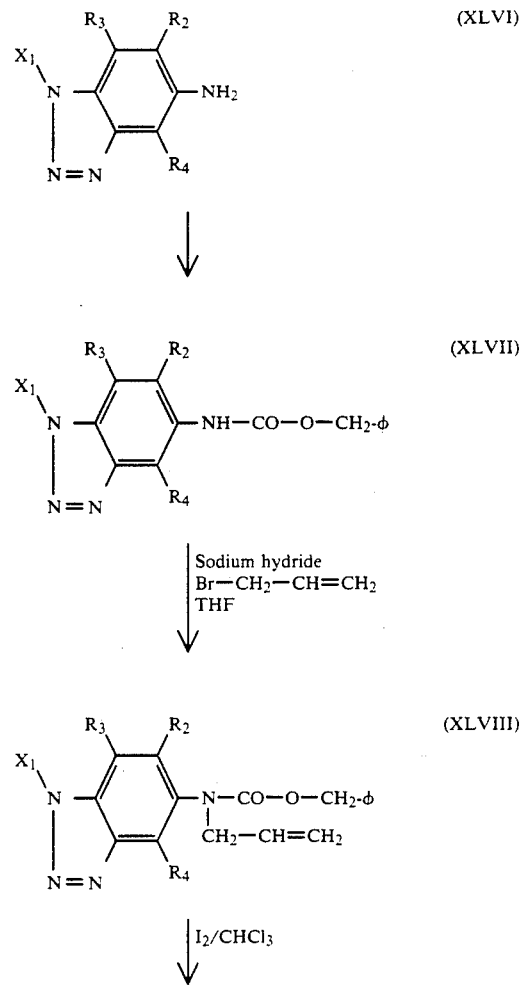
-continued
CHART G
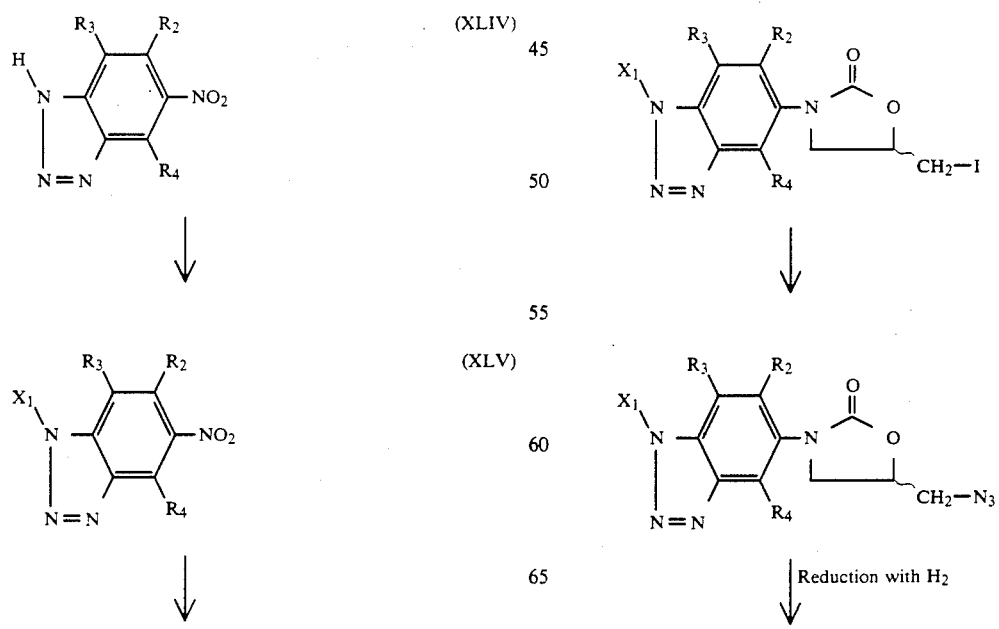

61
-continued
CHART G

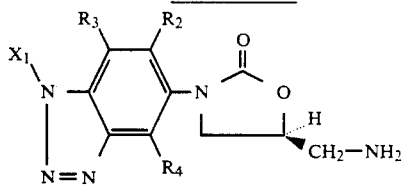
(LI)

↓ Acylation

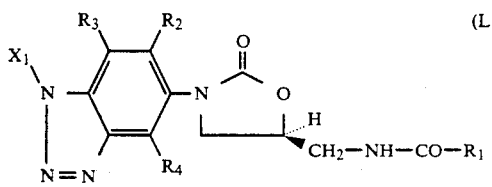
(LII)

↓ Deprotection

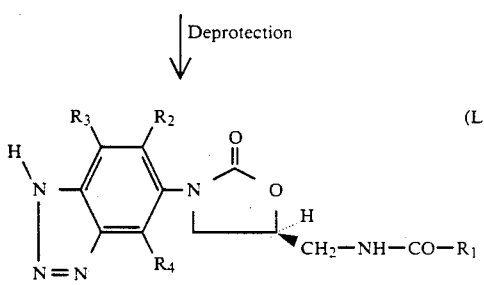
(LIII)

↓

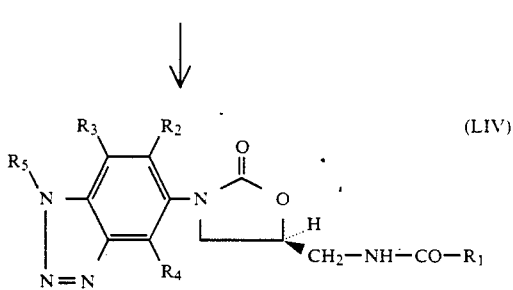
(LIV)

CHART H
3-(nitrogen substituted)phenyl-5β-(amidomethyl)oxazolidin-2-ones (LV)

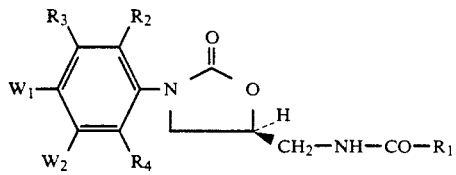
(LV)

includes:
indazolyloxazolidin-2-ones (XXXII)

where W$_1$ end is       W$_2$ end is
         —NR$_5$—N=CR$_6$— benzimidazolyloxazolidin-2-ones (XLIII)

where W$_1$ end is       W$_2$ end is
         —NR$_5$—CR$_6$=N— benzotriazolyloxazolidin-2-ones (LIV)

where W$_1$ end is       W$_2$ end is
         —NR$_5$—N=N—

62
-continued
CHART H

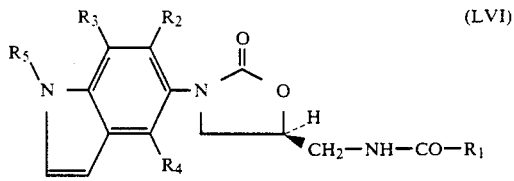
(LVI)

I claim:
1. A 5'-indolinyloxazolidin-2-one of formula (XI)

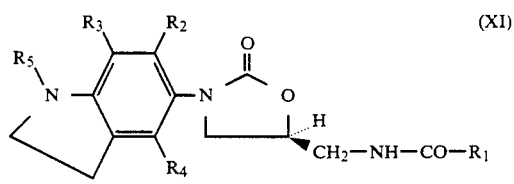
(XI)

where
(I) R$_1$ is —H,
C$_1$-C$_4$ alkyl,
—CHCl$_2$, —CCl$_3$,
cyclopropyl,
—O—R$_{1-6}$ where R$_{1-6}$ is C$_1$-C$_4$ alkyl,
—CH$_2$—OH,
—CH$_2$—OR$_{1-8}$ where R$_{1-8}$ is C$_1$-C$_4$ alkyl or
    —CO—R$_{1-9}$ where R$_{1-9}$ is C$_1$-C$_4$ alkyl or —φ;
(II) two of R$_2$, R$_3$ and R$_4$ and —H and the other of R$_2$,
    R$_3$ and R$_4$ is —H,
—F, —Cl, Br, —I,
C$_1$-C$_3$ alkyl,
—CO—O—R$_{2-1}$ where R$_{2-1}$ is C$_1$-C$_2$ alkyl or —φ,
—O—R$_{2-1}$ where R$_{2-1}$ is as defined above,
—COOH,
—COO$^-$,
—C≡N,
—NO$_2$,
—NR$_{2-4}$R$_{2-5}$ where R$_{2-4}$ and R$_{2-5}$ are the same or different and are C$_1$-C$_3$ alkyl,
where
(III) R$_5$ is
—CHO,
—CO—R$_{5-1}$ where R$_{5-1}$ is
    (A) C$_1$-C$_6$ alkyl optionally substituted with 1
        —O—CH$_3$, —φ, —COOH, —NH$_2$, —SO$_3$H or
        1-3 —Cl,
    (B) C$_3$-C$_7$ cycloalkyl,
    (C) 2-thiophene or 2-thiophenemethyl,
    (D) —φ optionally substituted with 1-3
        —F, —Cl, Br, —I,
C$_1$-C$_3$ alkyl,
—OH,
—CO—O—R$_{5-2}$ where R$_{5-2}$ is C$_1$-C$_4$ alkyl,
—O—R$_{5-2}$ where R$_{5-2}$ is as defined above,
—COOH,
—CO—N(—CH$_2$—CH$_2$—)$_2$O
—CO—NR$_{5-3}$R$_{5-4}$ where R$_{5-3}$ and R$_{5-4}$ are the same or different and are C$_1$-C$_3$ alkyl
—C≡N,
—CHOH—CH$_3$,
—CO—CH$_3$,
—SO—CH$_3$,
—SO—φ,
—S—CH$_3$, —$SO_2$—$CH_3$,
—$SO_3H$,
—$SO_2$—$NH_2$,
—$NR_{5-5}R_{5-6}$ where $R_{5-5}$ and $R_{5-6}$ are the same or different and are —H and $C_1$-$C_3$ alkyl,
—NH—CO—$R_{5-7}$ where $R_{5-7}$ is $C_1$-$C_4$ alkyl or —φ,
—CO—$CH_2$—CN,
—CO—$CH_2$—OH,
—CO—$CH_2$—O—φ where —φ is optionally substituted with 1-3 —O—$CH_3$, 1—$NO_2$ and 1 —$NH_2$,
—CO—$CH_2$—O—$R_{5-10}$ where $R_{5-10}$ is $C_1$-$C_4$ alkyl optionally substituted with —φ,
—φ optionally substituted with 1-3 —O—$CH_3$,
—CO—$R_{5-11}$ where $R_{5-11}$ is $C_1$-$C_6$ alkyl, —φ optionally substituted with 1-4 —F, 1-3 —Cl, 1 —$OCH_3$, —$NO_2$, —CO—$CH_3$, —$SO_2$—$CH_3$ and —$SO_2$—OH,
—CO—CH(NH—CO—$R_{5-12}$)—$R_{5-13}$ where $R_{5-13}$ is —H or —$CH_3$ and $R_{5-12}$ is $C_1$-$C_4$ alkyl, —φ optionally substituted with 1 or 2 —$OCH_3$, —Cl, —F, and —$N(CH_3)_2$,
—CO—$CHNH_2$—$R_{5-14}$ where $R_{5-14}$ is —$CH(CH_3)_2$, —$CH_2$— $CH(CH_3)_2$, —$CHCH_3$—$CH_2$—$CH_3$, —$CH_2$—OH, —CH(OH)—$CH_3$, —$CH_2$—φ, —$CH_2$—φ— OH, —$CH_2$—SH, —$CH_2$—$CH_2$—S'$CH_3$, and —$CH_2$—COOH,
—$SO_2$—$CH_3$,
—$SO_2$—φ,
—$SO_3H$,
and $R_6$ is —H and $C_1$-$C_3$ alkyl and pharmaceutically acceptable salts thereof.

2. A 5'-indolinyloxazolidin-2-one (XI) according to claim 1 where $R_1$ is selected from the group consisting of —H, $C_1$-$C_4$ alkyl, cyclopropyl, —$OCH_3$ and —$CHCl_2$ and where $R_5$ is selected from the group consisting of —CHO, —CO—$R_{5-1}$ where $R_{5-1}$ is —$CH_3$, —$C_2H_5$, —$CH(CH_3)_2$, —$CHCl_2$, —$CH_2$—OH, —$CH_2$—O—$CH_3$, 2-thiophene and cyclopentyl.

3. A 5'-indolinyloxazolidin-2-one (XI) according to claim 1 which is
3-(5'-1-acetylindolinyl)-5β-(acetamidomethyl)oxazolidin-2-one,
3-(5'-1-isobutyrlindolinyl]-5β-(acetamidomethyl)oxazolidin-2-one,
3-(5'-1-propanoylindolinyl)-5β-(acetamidomethyl)oxazolidin-2-one,
3-(5'-1-cyclopentylcarbonylindolinyl)-5β-(acetamidomethyl)oxazolidin-2-one,
3-(5'-1-formylindolinyl)5β-(acetamidomethyl)oxazolidin-2-one,
3-(5'-1-chloroacetylindolinyl)-5β-(acetamidomethyl)oxazolidin-2-one,
3-(5'-1-dichloroacetylindolinyl)-5β-(acetamidomethyl)oxazolidin-2-one,
3-(5'-1-phenylacetylindolinyl)-5β-(acetamidomethyl)oxazolidin-2-one,
3-(5'-1-(O-acetyl(hydroxyacetyl)indolinyl))-5β-(acetamidomethyl)oxazolidin-2-one,
3-[5'-1-(2-thienylcarbonyl)indolinyl]-5β-(acetamidomethyl)oxazolidin-2-one,
3-(5'-1-benzolindolinyl)-5β-(acetamidomethyl)oxazolidin-2-one,
3-(5'-1-methylsulfonylindolinyl)-5β-(acetamidomethyl)oxazolidin-2-one,
3-(5'-1-hydroxyacetylindolinyl)-5β-(acetamidomethyl)oxazolidin-2-one,
3-(5'-1-benzyloxyacetylindolinyl)-5β-(acetamidomethyl)oxazolidin-2-one,
3-(5'-1-p-chlorobenzoylindolinyl)-5β-(acetamidomethyl)oxazolidin-2-one,
3-(5'-1-methoxyacetylindolinyl)-5β-(acetamidomethyl)oxazolidin-2-one and
3-(5'-1-hexanoylindolinyl)-5β-(acetamidomethyl)oxazolidin-2-one.

4. A compound selected from the group consisting of a 5'-indolinyloxazolidin-2-one of formula (XIII)

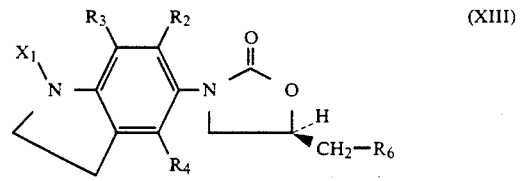

where
(I) $X_1$ is —CO—$CH_3$, —CO—O—$C(CH_3)_3$, —CO—O—$CH_2$—φ and —CO—O—$(CH_2)_2$—$Si(CH_3)_3$,
(II) two of $R_2$, $R_3$ and $R_4$ are —H and the other of $R_2$, $R_3$ and $R_4$ is
—H,
—F, —Cl, Br, —I,
$C_1$-$C_4$ alkyl,
—CO—O—$R_{2-1}$ where $R_{2-1}$ is $C_1$-$C_2$ alkyl or —φ,
—O—$R_{2-1}$ where $R_{2-1}$ is as defined above,
—COOH,
—$COO^-$,
$C \equiv N$,
—$NO_2$,
—$NR_{2-4}R_{2-5}$ where $R_{2-4}$ and $R_{2-5}$ are the same or different and are $C_1$-$C_3$ alkyl,
(III) $R_6$ is —I, —$N_3$ and —$NH_2$ and salts thereof.

5. A 5'-indolinyloxazolidin-2-one of formula (XIII) according to claim 4 where $X_1$ is t-butyloxycarbonyl.

6. A 5'-indolinyloxazolidin-2-one of formula (XIII) according to claim 4 where the oxazolidinone is selected from the group consisting of
(±)-3-(5'-1-acetylindolinyl)-5-(iodomethyl)oxazolidin-2-one,
(±)-3-(5'-1-acetylindolinyl)-5-(azidomethyl)oxazolidin-2-one and
3-(5'1-acetylindolinyl)-5β-(amiomethyl)oxazolidin-2-one.

7. 3-(5'-1-Allylindolinyl)-5β-(acetamidomethyl)oxazolidin-2-one.

* * * * *